(12) United States Patent
Dubinett et al.

(10) Patent No.: US 11,236,139 B2
(45) Date of Patent: Feb. 1, 2022

(54) COMBINATION IMMUNOTHERAPY

(71) Applicants: The Regents of the University of California, Oakland, CA (US); United States Government represented by the Department of Veterans Affairs, Washington, DC (US)

(72) Inventors: Steven M. Dubinett, Los Angeles, CA (US); Sherven Sharma, Culver City, CA (US); Jay M. Lee, Los Angeles, CA (US)

(73) Assignees: THE REGENTS OF THE UNIVERSITY OF CALIFORNIA, Oakland, CA (US); UNITED STATES GOVERNMENT REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 71 days.

(21) Appl. No.: 15/524,740

(22) PCT Filed: Nov. 5, 2015

(86) PCT No.: PCT/US2015/059297
§ 371 (c)(1),
(2) Date: May 5, 2017

(87) PCT Pub. No.: WO2016/073759
PCT Pub. Date: May 12, 2016

(65) Prior Publication Data
US 2018/0194825 A1    Jul. 12, 2018

Related U.S. Application Data

(60) Provisional application No. 62/075,532, filed on Nov. 5, 2014.

(51) Int. Cl.
| *A61K 35/15* | (2015.01) |
| *A61K 39/00* | (2006.01) |
| *C07K 14/52* | (2006.01) |
| *A61K 38/19* | (2006.01) |
| *A61K 9/00* | (2006.01) |
| *A61K 39/395* | (2006.01) |
| *A61K 48/00* | (2006.01) |
| *A61P 35/00* | (2006.01) |
| *A61K 45/06* | (2006.01) |
| *C07K 16/28* | (2006.01) |
| *C07K 16/24* | (2006.01) |
| *C12N 7/00* | (2006.01) |

(52) U.S. Cl.
CPC .......... *C07K 14/521* (2013.01); *A61K 9/0019* (2013.01); *A61K 38/195* (2013.01); *A61K 39/0011* (2013.01); *A61K 39/3955* (2013.01); *A61K 39/39558* (2013.01); *A61K 45/06* (2013.01); *A61K 48/00* (2013.01); *A61P 35/00* (2018.01); *C07K 16/24* (2013.01); *C07K 16/249* (2013.01); *C07K 16/2818* (2013.01); *C12N 7/00* (2013.01); *A61K 2039/5154* (2013.01); *A61K 2039/5256* (2013.01); *A61K 2039/54* (2013.01); *A61K 2039/545* (2013.01); *C07K 2317/76* (2013.01); *C12N 2710/10041* (2013.01); *C12N 2710/10043* (2013.01); *C12N 2710/10071* (2013.01)

(58) Field of Classification Search
CPC .......................... A61K 35/15; A61K 2039/505
See application file for complete search history.

(56) References Cited

U.S. PATENT DOCUMENTS

| 6,808,710 | B1 | 10/2004 | Wood et al. |
| 7,563,869 | B2 | 7/2009 | Honjo et al. |
| 7,595,048 | B2 | 9/2009 | Honjo et al. |
| 7,943,743 | B2 | 5/2011 | Korman et al. |
| 8,008,449 | B2 | 8/2011 | Korman et al. |
| 8,088,905 | B2 | 1/2012 | Collins et al. |
| 8,168,179 | B2 | 5/2012 | Honjo et al. |
| 8,217,149 | B2 | 7/2012 | Irving et al. |
| 8,246,955 | B2 | 8/2012 | Honjo et al. |

(Continued)

FOREIGN PATENT DOCUMENTS

| WO | WO 2007/113648 | 10/2007 |
| WO | WO 2009/117566 A1 | 9/2009 |

(Continued)

OTHER PUBLICATIONS

Li et al. (Immunol Lett. Nov. 15, 2007; 113 (2): 90-8).*

(Continued)

*Primary Examiner* — Stephen L Rawlings
(74) *Attorney, Agent, or Firm* — Mark S. Cohen; Pearl Cohen Zedek Latzer Baratz LLP

(57) ABSTRACT

The invention is based on the disclosure provided herein that secondary lymphoid organ chemokine (SLC) inhibits the growth of syngeneic tumors in vivo. Thus, the invention provides a method of treating cancer in a mammal subject by administering a therapeutically effective amount of an SLC to the mammal in combination with a checkpoint inhibitor, including monoclonal antibodies and small molecule inhibitors. Exemplary checkpoint molecules include CTLA-4, a CTLA-4 receptor, PD-1, PD-L1, PD1-L2, 4-1BB, OX40, LAG-3, TIM-3 or a combination thereof. SLCs useful in the methods of the invention include SLC polypeptides, variants and fragments and related nucleic acids.

9 Claims, 11 Drawing Sheets

Specification includes a Sequence Listing.

(56) References Cited

U.S. PATENT DOCUMENTS

| | | |
|---|---|---|
| 8,287,856 B2 | 10/2012 | Li et al. |
| 8,354,509 B2 | 1/2013 | Carven et al. |
| 8,552,154 B2 | 10/2013 | Freeman et al. |
| 8,617,546 B2 | 12/2013 | Kang et al. |
| 8,735,553 B1 | 5/2014 | Li et al. |
| 8,741,295 B2 | 6/2014 | Olive |
| 8,779,105 B2 | 7/2014 | Korman et al. |
| 8,927,697 B2 | 1/2015 | Davis et al. |
| 2003/0175801 A1 | 9/2003 | Dubinett et al. |
| 2020/0206271 A1* | 7/2020 | Lu .................. A61K 38/215 |

FOREIGN PATENT DOCUMENTS

| | | |
|---|---|---|
| WO | WO 2016/073759 | 5/2016 |
| WO | WO 2017/042394 | 3/2017 |
| WO | WO 2017/151524 | 9/2017 |
| WO | WO 2019/217898 A1 | 11/2019 |

OTHER PUBLICATIONS

McDermitt et al. (Cancer Med. Oct. 2013; 2 (5): 662-73).*
McDermott et al. (Cancer Med. Oct. 2013; 2 (5): 662-73).*
Nagira et al. (J. Biol. Chem. Aug. 1, 1997; 272 (31): 19518-240).*
Pecher et al. (Anticancer Res. Jul.-Aug. 2001; 21 (4A): 2591-6).*
Guo et al. (Gene Ther. Jun. 2002; 9 (12): 793-803).*
Miller et al. (Hum. Gene Ther. Jan. 1, 2000; 11 (91): 53-65).*
Chan et al. (Blood. Jun. 1, 1999; 93 (11): 3610-6).*
Denkert et al. (J. Clin. Oncol. Jan. 1, 2010; 28 (1): 105-13).*
Keir et al. (Annu. Rev. Immunol. 2008; 26: 677-704).*
Shin et al. (Curr. Opin. Immunol. Apr. 2015; 33: 23-35).*
Kirk et al. (Cancer Res. Dec. 15, 2001; 61 (24): 8794-802).*
Sharma et al. (J. Immunol. May 1, 2000; 164 (9): 4558-63).*
Stancovski et al. (Proceedings of the National Academy of Science USA. 1991; 88: 8691-8695).*
Jiang et al. (J. Biol. Chem. Feb. 11, 2005; 280 (6): 4656-4662).*
Riemer et al. (Mol. Immunol. 2005; 42: 1121-1124).*
Nielsen et al. (Cell. Immunol. Jun. 2005; 235 (2): 109-16).*
Lin et al. (Cancers (Basel). Jun. 2014; 6 (2): 1098-1110; published on-line May 7, 2014; pp. 1-13).*
Patnaik et al. (J. Clin. Oncol. 2012; 30 (15 Suppl.): 2512).*
Garon et al. (Ann. Oncol. Jan. 2014.; 25 (Supplements): v1-v41).*
Morgensztern (J. Thorac. Dis. Sep. 2019.; 11 (Suppl. 15): S1963-S1965).*
Robert et al. (Lancet. Sep. 20, 2014; 384 (9948): 1109-17).*
Patnaik et al. (Clin. Cancer Res. Oct. 1, 2015; 21 (19): 4286-93).*
Turnquist et al. (Int. J. Oncol. Mar. 2007; 30 (3): 631-9).*
Li et al. (Clin. Immunol. Nov. 2009; 133 (2): 184-97).*
Tirapu et al. (Curr. Gene Ther. Feb. 2002; 2 (1): 79-89).*
Kar et al., "Novel CCL21-Vault Nanocapsule Intratumoral Delivery Inhibits Lung Cancer Growth", PLoS ONE, vol. 6, No. 5, May 3, 2011, e18758, 8 pages.
Sharma, S. et al., "CCL21 Chemokine Therapy for Lung Cancer", Int. Trends Immun., Jan. 1, 2013, 1(1): 10-15.
Yang et al., "Intratumoral Administration of Dendritic Cells Overexpressing CCL21 Generates Systemic Antitumor Responses and Confers Tumor Immunity", Clinical Cancer Research, vol. 10, 2891-2901, Apr. 15, 2004.
Hong et al., "The Lymphoid Chemokine CCL21 Enhances the Cytotoxic T Lymphocyte-Inducing Functions of Dendritic Cells", Scandinavian Journal of Immunology, vol. 79, No. 3, Mar. 1, 2014, pp. 173-180.
Baratelli et al., "Pre-clinical characterization of GMP grade CCL21-gene modified dendritic cells for application in a phase I trial in Non-Small Cell Lung Cancer", Journal of Translational Medicine, 6:38, Jul. 22, 2008, 18 pages.
Yang et al., "Intrapulmonary Administration of CCL21 Gene-Modified Dendritic Cells Reduces Tumor Burden in Spontaneous Murine Bronchoalveolar Cell Carcinoma", Cancer Res 2006, 66:6, Mar. 15, 2006, pp. 3205-3213.

McDermott et al., "PD-1 as a potential target in cancer therapy", Cancer Medicine 2013, 2(5): 662-673, Jul. 21, 2013.
Pardoll, "The blockade of immune checkpoints in cancer immunotherapy", Nature Reviews, Cancer, vol. 12, No. 4, Apr. 1, 2012, pp. 252-264.
Sharma, P. et al., "The future of immune checkpoint therapy", Science, vol. 348, No. 6230, Apr. 3, 2015, pp. 56-61.
Extended European Search Report, dated May 30, 2018, from corresponding European Patent Application No. 15856689.3.
"MK-3475 Effective Against Melanoma", Cancer Discovery, Aug. 2014; 4:863-864; published online first Jun. 26, 2014.
Brahmer et al., "Immune Checkpoint Inhibitors: Making Immunotherapy a Reality for the Treatment of Lung Cancer", Cancer Immunology Research, Aug. 2013, 1(2): 85-91; published online first Jul. 22, 2013.
Sakthivel et al., "Therapeutic Intervention in Cancer and Chronic Viral Infections: Antibody Mediated Manipulation of PD-1/PD-L1 Interaction", Reviews on Recent Clinical Trials, 2012, 7(11): 10-23.
Office Action, dated Oct. 1, 2019, from corresponding Japanese Patent Application No. 2017-525120.
Office Action, dated Mar. 26, 2020, from corresponding European Patent Application No. 15856689.3.
Bobanga et al., "Chemokines as Cancer Vaccine Adjuvants", Vaccines 2013, 1, 444-462.
He et al., "Blocking Programmed Death-1 Ligand-PD-1 Interactions by Local Gene Therapy Results in Enhancement of Antitumor Effect of Secondary Lymphoid Tissue Chemokine", The Journal of Immunology, 173(8): 4919-4928 (Oct. 6, 2004).
Gandhi et al., "Pembrolizumab plus Chemotherapy in Metastatic Non-Small-Cell Lung Cancer", The New England Journal of Medicine, May 2018, 378(22): 2078-2092.
Hellmann et al., "Nivolumab plus Ipilimumab in Lung Cancer with a High Tumor Mutational Burden", The New England Journal of Medicine, May 2018, 378(22): 2093-2104.
Cyster, "Chemokines and the Homing of Dendritic Cells to the T Cell Areas of Lymphoid Organs", J. Exp. Med., Feb. 1, 1999, 189(3): 447-450.
Ogata et al., "Chemotactic Response Toward Chemokines and Its Regulation by Transforming Growth Factor-$\beta$1 of Murine Bone Marrow Hematopoietic Progenitor Cell-Derived Different Subset of Dendritic Cells", Blood, May 15, 1999, 93(10): 3225-3232.
Willimann et al., "The chemokine SLC is expressed in T cell areas of lymph nodes and mucosal lymphoid tissues and attracts activated T cells via CCR7", Eur. J. Immunol., 1998, 28: 2025-2034.
Jenh et al., "Cutting Edge: Species Specificity of the CC Chemokine 6Ckine Signaling Through the CXC Chemokine Receptor CXCR3: Human 6Ckine Is Not a Ligand for the Human or Mouse CXCR3 Receptors", The Journal of Immunology, 1999, 162: 3765-3769.
Kellermann et al., "The CC Chemokine Receptor-7 Ligands 6Ckine and Macrophage Inflammatory Protein-3$\beta$ Are Potent Chemoattractants for In Vitro- and In Vivo-Derived Dendritic Cells", The Journal of Immunology, 1999, 162: 3859-3864.
Sallusto et al., "Rapid and coordinated switch in chemokine receptor expression during dendritic cell maturation", Eur. J. Immunol., 1998, 28: 2760-2769.
Sozzani et al., "Cutting Edge: Differential Regulation of Chemokine Receptors During Dendritic Cell Maturation: A Model for Their Trafficking Properties", The Journal of Immunology, 1998, 161:1083-1086.
Dieu et al., "Selective Recruitment of Immature and Mature Dendritic Cells by Distinct Chemokines Expressed in Different Anatomic Sites", J. Exp. Med., Jul. 20, 1998, 188(2): 373-386.
Tang et al., "Biomarkers for early diagnosis, prognosis, prediction, and recurrence monitoring of non-small cell lung cancer", OncoTargets and Therapy, 2017, 10: 4527-4534.
Siegel et al., "Cancer Statistics 2015", CA: A Cancer Journal for Clinicians, Jan./Feb. 2015, 65(1): 5-29.
Reck et al., "Pembrolizumab versus Chemotherapy for PD-L1-Positive Non-Small-Cell Lung Cancer", The New England Journal of Medicine, Nov. 10, 2016, 375(19): 1823-1833.
Shaw et al., "Clinical Features and Outcome of Patients With Non-Small-Cell Lung Cancer Who Harbor EML4-ALK", Journal of Clinical Oncology, Sep. 10, 2009, 27(26): 4247-4253.

(56) References Cited

OTHER PUBLICATIONS

Lynch et al., "Activating Mutations in the Epidermal Growth Factor Receptor Underlying Responsiveness of Non-Small-Cell Lung Cancer to Gefitinib", The New England Journal of Medicine, May 20, 2004, 350(21): 2129-2139.

Paez et al., "EGFR Mutations in Lung Cancer: Correlation with Clinical Response to Gefitinib Therapy", Science, Jun. 4, 2004, 304(5676): 1497-1500.

Pao et al., "EGF receptor gene mutations are common in lung cancers from "never smokers" and are associated with sensitivity of tumors to gefitinib and erlotinib", Proc Natl Acad Sci, Sep. 7, 2004, 101(36): 13306-13311.

Garon et al., "Pembrolizumab for the Treatment off Non-Small-Cell Lung Cancer", The New England Journal of Medicine, May 21, 2015, 372(21): 2018-2028.

Scagliotti et al., "Phase III study comparing cisplatin plus gemcitabine with cisplatin plus pemetrexed in chemotherapy-naïve patients with advanced-stage non-small-cell lung cancer", J Clin Oncol, Jul. 20, 2008, 26: 3543-3551.

Brahmer et al., "Nivolumab versus Docetaxel in Advanced Squamous-Cell Non-Small-Cell Lung Cancer", The New England Journal of Medicine, Jul. 9, 2015, 373(2):123-135.

Borghaei et al., "Nivolumab versus Docetaxel in Advanced Nonsquamous Non-Small-Cell Lung Cancer", The New England Journal of Medicine, Oct. 22, 2015, 373(17):1627-1639.

Carbone et al., "First-Line Nivolumab in Stage IV or Recurrent Non-Small-Cell Lung Cancer", The New England Journal of Medicine, Jun. 22, 2017, 376(25):2415-2426.

Lee et al., "Phase I Trial of Intratumoral Injection of CCL21 Gene-Modified Dendritic Cells in Lung Cancer Elicits Tumor-Specific Immune Response and CD8+ T-cell Infiltration", Clin Cancer Res, May 3, 2017, 23(16): 4556-4568.

Novello et al., "Metastatic non-small-cell lung cancer: ESMO Clinical Practice Guidelines for diagnosis, treatment and follow-up", Annals of Oncology, Sep. 2016, vol. 27, Supplement 5, v1-v27.

Gettinger et al., "Overall Survival and Long-Term Safety of Nivolumab (Anti-Programmed Death 1 Antibody, BMS-936558, ONO-4538) in Patients With Previously Treated Advanced Non-Small-Cell Lung Cancer", Journal of Clinical Oncology, Apr. 20, 2015, 33(18): 2004-2012.

Anagnostou et al., "Cancer Immunotherapy: A Future Paradigm Shift in the Treatment of Non-Small Cell Lung Cancer", Clinical Cancer Research, Mar. 1, 2015, 21(5): 976-984.

Robert et al., "Distinct immunological mechanisms of CTLA-4 and PD1 blockade revealed by analyzing TCR usage in blood lymphocytes", OncoImmunology, 3:6, e29244 (Jun. 2014).

Dubinett et al., "Tumor Antigens in Thoracic Malignancy", Am. J. Respir. Cell Mol. Biol., vol. 22, pp. 524-527 (May 2000).

Restifo et al., "Identification of Human Cancers Deficient in Antigen Processing", The Journal of Experimental Medicine, vol. 177, pp. 265-272 (Feb. 1, 1993).

Dubinett et al., "Chemokines: Can Effector Cells be Re-directed to the Site of Tumor?", Cancer J., 2010, 16(4): 325-335.

Okazaki et al., "PD-1 immunoreceptor inhibits B cell receptor-mediated signaling by recruiting src homology 2-domain-containing tyrosine phosphatase 2 to phosphotyrosine", Proc. Natl. Acad. Sci., Nov. 20, 2001, 98(24): 13866-13871.

Sheppard et al., "PD-1 inhibits T-cell receptor induced phosphorylation of the ZAP70/CD3ζ signalosome and downstream signaling to PKCθ", FEBS Letters 574, Sep. 10, 2004, pp. 37-41.

Steinman, "Decisions About Dendritic Cells: Past, Present, and Future", Annu. Rev. Immunol., 2012, 30:1-22.

Roberts et al., "Critical Role for CD103+/CD141+ Dendritic Cells Bearing CCR7 for Tumor Antigen Trafficking and Priming of T Cell Immunity in Melanoma", Cancer Cell, 30: 324-336, Aug. 8, 2016.

Spranger et al., "Tumor-Residing Batf3 Dendritic Cells Are Required for Effector T Cell Trafficking and Adoptive T Cell Therapy", Cancer Cell, 31: 711-723, May 8, 2017.

Sabado et al., "Dendritic cell-based immunotherapy", Cell Research, 2017, 27:74-95.

Vicari et al., "Antitumor Effects of the Mouse Chemokine 6Ckine/SLC Through Angiostatic and Immunological Mechanisms", J. Immunol., Aug. 15, 2000, 165:1992-2000.

Politi et al., "Lung Cancer in the Era of Precision Medicine", Clin Cancer Res., 21 (10): 2213-2220, May 15, 2015.

Sharma et al., "Primary, Adaptive, and Acquired Resistance to Cancer Immunotherapy", Cell, 168:707-723, Feb. 9, 2017.

Zou et al., "PD-L1 (B7-H1) and PD-1 pathway blockade for cancer therapy: Mechanisms, response biomarkers, and combinations", Science Translational Medicine, vol. 8 Issue 328, 328rv4, 16 pages, Mar. 2, 2016.

Parra et al., "Validation of multiplex immunofluorescence panels using multispectral microscopy for immune-profiling of formalin-fixed and paraffin-embedded human tumor tissues", Scientific Reports, 7: 13380, 11 pages, Oct. 17, 2017.

Trinchieri, "Interleukin-12: A Cytokine Produced by Antigen-Presenting Cells With Immunoregulatory Functions in the Generation of T-Helper Cells Type 1 and Cytotoxic Lymphocytes", Blood, 84(12): 4008-4027, Dec. 15, 1994.

Breton et al., "Human dendritic cells (DCs) are derived from distinct circulating precursors that are precommitted to become CD1c+ or CD141+ DCs", J. Exp. Med. 213(13): 2861-2870, Dec. 12, 2016.

Guillaums et al., "Unsupervised High-Dimensional Analysis Aligns Dendritic Cells across Tissues and Species", Immunity 45, 669-684, Sep. 20, 2016.

Alcantara-Hernandez et al., "High-Dimensional Phenotypic Mapping of Human Dendritic Cells Reveals Interindividual Variation and Tissue Specialization", Immunity 47, 1037-1050, e1-e6, Dec. 19, 2017.

Galon et al., "The Adaptive Immunological Microenvironment in Colorectal Cancer: A Novel Perspective", Cancer Research, 67(5): 1883-1886, Mar. 1, 2007.

Accession No. AB002409.1, "*Homo sapiens* CCL21 mRNA for CC chemokine ligand 21, complete cds", Nucleotide—NCBI, GenBank: AB002409.1, retrieved from Internet May 27, 2021, https://www.ncbi.nlm.nih.gov/nuccore/AB002409.

Accession No. BAA21817.1, "CC chemokine ligand 21 [*Homo sapiens*]", Protein—NCBI, GenBank: BAA21817.1, retrieved from Internet May 27, 2021, https://www.ncbi.nlm.nih.gov/protein/BAA21817.

Accession No. NP_035465.2, "C—C motif chemokine 21b isoform 1 precursor [Mus musculus]". Protein—NCBI, GenPept, NCBI Reference Sequence: NP_035465.2, retrieved from Internet May 27, 2021, https://www.ncbi.nlm.nih.gov/protein/NP_035465.2.

Accession No. NM_011335.3, "Mus musculus chemokine (C—C motif) ligand 21B (leucine) (Ccl21b), transcript variant 1, mRNA", Nucleotide—NCBI, GenBank, NCBI Reference Sequence: NM_011335.3, retrieved from Internet May 27, 2021, https://www.ncbi.nlm.nih.gov/nuccore/NM_011335.

Kazandjian et al., "Characterization of outcomes in patients with metastatic non-small cell lung cancer treated with programmed cell death protein 1 inhibitors past RECIST version 1.1—defined disease progression in clinical trials", Seminars in Oncology 44 (2017) 3-7.

Kadam et al., "PD-1 Immune Checkpoint Blockade Promotes Therapeutic Cancer Vaccine to Eradicate Lung Cancer", Vaccines, Jun. 18, 2020; 8, 317, 12 pages, http://dx.doi.org/10.3390/vaccines8020317.

Reck et al., "Five-Year Outcomes With Pembrolizumab Versus Chemotherapy for Metastatic Non-Small-Cell Lung Cancer With PD-L1 Tumor Proportion Score ≥ 50%", Journal of Clinical Oncology, published at ascopubs.org/journal/jco on Apr. 19, 2021: DOI https://doi.org/10.1200/JCO.21.00174, 15 pages.

Waterhouse et al., "Real-world outcomes of immunotherapy-based regimens in first-line advanced non-small cell lung cancer", Lung Cancer, Apr. 2021, 156: 41-49.

Borghaei et al., "Five-Year Outcomes From the Randomized, Phase III Trials CheckMate 017 and 057: Nivolumab Versus Docetaxel in Previously Treated Non-Small-Cell Lung Cancer", J. Clin. Oncol., Jan. 15, 2021, 39(7): 723-733.

Jemal et al., "Cancer Statistics, 2003", CA Cancer J. Clin., Jan./Feb. 2003; 53(1): 5-26.

Moeini et al., "Synergistic effect of programmed cell death protein 1 blockade and secondary lymphoid tissue chemokine in the induc-

(56) References Cited

OTHER PUBLICATIONS tion of anti-tumor immunity by a therapeutic cancer vaccine", Arch Virol (2017), 162:333-346, published online Oct. 3, 2016, DOI 10.1007/s00705-016-3091-5.
Moeini et al., "Erratum to: Synergistic effect of programmed cell death protein 1 blockade and secondary lymphoid tissue chemokine in the induction of anti-tumor immunity by a therapeutic cancer vaccine", Arch Virol (2017), 162:347, published online Nov. 24, 2016, DOI 10.1007/s00705-016-3160-9.
Anderson, "Tim-3: An Emerging Target in the Cancer Immunotherapy Landscape", Cancer Immunology Research, May 2014, 2(5): 393-398.
Postow et al., "Immune Checkpoint Blockade in Cancer Therapy", J. Clin. Oncol., Jun. 10, 2015, 33(17): 1974-1982.
Perrot et al., "Dendritic Cells Infiltrating Human Non-Small Cell Lung Cancer Are Blocked at Immature Stage", The Journal of Immunology, 2007; 178: 2763-2769.
Gray et al., "A phase I/randomized phase II study of GM.CD40L vaccine in combination with CCL21 in patients with advanced lung adenocarcinoma", Cancer Immunology, Immunotherapy, Sep. 2018, 67:1853-1862.
Tembhre et al., "Alteration in regulatory T cells and programmed cell death 1-expressing regulatory T cells in active generalized vitiligo and their clinical correlation", Br J Dermatol., Apr. 2015; 172(4):940-50, abstract.
Shields et al., "Induction of lymphoidlike stroma and immune escape by tumors that express the chemokine CCL21", Science, May 7, 2010; 328(5979):749-52, abstract.
Tang et al., "Immunotherapy and tumor microenvironment", Cancer Lett., Jan. 1, 2016; 370(1): 85-90.
Sasikumar et al., "Small-Molecule Immune Checkpoint Inhibitors Targeting PD-1/PD-L1 and Other Emerging Checkpoint Pathways", BioDrugs, Oct. 2018, 32(5): 481-497.
Qin et al., "Enhancement of antitumour immunity by a novel chemotactic antigen DNA vaccine encoding chemokines and multiepitopes of prostate-tumour-associated antigens", Immunology, 2006, 117: 419-430.
Qin et al., "Specific antitumor immune response induced by a novel DNA vaccine composed of multiple CTL and T helper cell epitopes of prostate cancer associated antigens", Immunol. Lett., Jun. 15, 2005; 99(1): 85-93, abstract.
Lee et al., "PD-L1 expression correlates with immune response in a Phase I trial of CCL21 gene modified dendritic cell therapy in lung cancer", Journal for ImmunoTherapy of Cancer 2014, 2(Suppl 3):O20.
Yoshida et al., "EBI1-ligand chemokine (ELC) attracts a broad spectrum of lymphocytes: activated T cells strongly up-regulate CCR7 and efficiently migrate toward ELC", International Immunology, 1998, 10(7): 901-910.
Zou et al., "Inhibitory B7-family molecules in the tumour microenvironment", Nature Reviews, Immunology, Jun. 2008, vol. 8, pp. 467-477.
Carmi et al., "Allogeneic IgG combined with dendritic cell stimuli induce antitumour T-cell immunity", Nature, May 7, 2015, vol. 521, pp. 99-104.
McBride et al., "Genetic Modification of a Murine Fibrosarcoma to Produce Interleukin 7 Stimulates Host Cell Infiltration and Tumor Immunity", Cancer Research, Jul. 1992, 52: 3931-3937.
Hagenbaugh et al., "Altered Immune Responses in Interleukin 10 Transgenic Mice", The Journal of Experimental Medicine, Jun. 16, 1997, 185(12): 2101-2110.
Segal et al., "Preliminary data from a multi-arm expansion study of MEDI4736, an anti-PD-L1 antibody", Journal of Clinical Oncology, 2014, vol. 32, Issue 15 suppl., abstract.
Tanabe et al., "Identification of a new mouse beta-chemokine, thymus-derived chemotactic agent 4, with activity on T lymphocytes and mesangial cells", J. Immunol., 1997; 159: 5671-5679.
Dubinett et al., "Down-Regulation of Murine Fibrosarcoma Transforming Growth Factor-β1 Expression by Interleukin 7", Journal of the National Cancer Institute, Apr. 19, 1995, 87(8): 593-597.

Herbst et al., "A study of MPDL3280A, an engineered PD-L1 antibody in patients with locally advanced or metastatic tumors", Journal of Clinical Oncology, 2013, vol. 31, Issue 15 suppl., abstract.
Nagarsheth et al., "Chemokines in the cancer microenvironment and their relevance in cancer immunotherapy", Nature Reviews, Immunology, Sep. 2017, vol. 17, pp. 559-572.
Sharma et al., "Secondary Lymphoid Organ Chemokine Reduces Pulmonary Tumor Burden in Spontaneous Murine Bronchoalveolar Cell Carcinoma", Cancer Research, Sep. 2001, 61: 6406-6412.
Sharma et al., "SLC/CCL21-mediated anti-tumor responses require IFNγ, MIG/CXCL9 and IP-10/CXCL10", Molecular Cancer, Apr. 2003, 2:22, 6 pages.
Herbst et al., "Pembrolizumab versus docetaxel for previously treated, PD-L1-positive, advanced non-small-cell lung cancer (KEYNOTE-010): a randomised controlled trial", The Lancet, Apr. 9, 2016, 387: 1540-1550.
Sharma et al., "T Cell-Derived IL-10 Promotes Lung Cancer Growth by Suppressing Both T Cell and APC Function", J. Immunol., 1999, 163: 5020-5028.
Sharma et al., "Tumor Cyclooxygenase-2/Prostaglandin $E_2$-Dependent Promotion of FOXP3 Expression and $CD4^+CD25^+$ T Regulatory Cell Activities in Lung Cancer", Cancer Research, Jun. 15, 2005, 65(12): 5211-5220.
Dubinett et al., "Adoptive Immunotherapy of Murine Pulmonary Metastases with Interleukin 2 and Interferon-gamma", Am. J. Respir. Cell Mol. Biol., 1989, vol. 1, pp. 361-369.
Dubinett et al., "Cytokine Administration Alters the Distribution of Activated Lymphocytes to the Lung", Pathobiology, 1991, 59:372-377.
Dubinett et al., "Intratumoral interleukin-2 immunotherapy: activation of tumor-infiltrating and splenic lymphocytes in vivo", Cancer Immunol. Immunother., 1993, 36: 156-162.
Hillinger et al., "EBV-Induced Molecule 1 Ligand Chemokine (ELC/CCL19) Promotes IFN-γ-Dependent Antitumor Responses in a Lung Cancer Model", The Journal of Immunology, 2003, 171: 6457-6465.
Macatonia et al., "Dendritic cells produce IL-12 and direct the development of Th1 cells from naive $CD4^+$ T cells", The Journal of Immunology, 1995, 154:5071-5079.
Herbst et al., "Predictive correlates of response to the anti-PD-L1 antibody MPDL3280A in cancer patients", Nature, Nov. 27, 2014, vol. 515, pp. 563-567.
Chiarle et al., "The anaplastic lymphoma kinase in the pathogenesis of cancer", Nature Reviews, Cancer, Jan. 2008, vol. 8, p. 11-23.
Tumeh et al., "PD-1 blockade induces responses by inhibiting adaptive immune resistance", Nature, Nov. 27, 2014, vol. 515, pp. 568-571.
Powles et al., "Inhibition of PD-L1 by MPDL3280A and clinical activity in pts with metastatic urothelial bladder cancer (UBC)", Journal of Clinical Oncology, 2014, vol. 32, Issue 15 suppl., abstract.
Hu et al., "Induction of Potent Antitumor Immunity by Intratumoral Injection of Interleukin 23-Transduced Dendritic Cells", Cancer Research, Sep. 1, 2006, 66(17): 8887-8896.
Rizvi et al., "Mutational landscape determines sensitivity to PD-1 blockade in non-small cell lung cancer", Science, Apr. 3, 2015, 348(6230): 124-128.
Srivastava et al., "Myeloid suppressor cells and immune modulation in lung cancer", Immunotherapy, Mar. 2012, 4(3): 291-304.
Spiegel et al., "Non-Small Cell Lung Cancer Clinical Trials Requiring Biopsies With Biomarker-Specific Results for Enrollment Provide Unique Challenges", Cancer, Dec. 15, 2017, 123:4800-4807.
Huang et al., "Non-Small Cell Lung Cancer Cyclooxygenase-2-dependent Regulation of Cytokine Balance in Lymphocytes and Macrophages: Up-Regulation of Interleukin 10 and Down-Regulation of Interleukin 12 Production", Cancer Research, Mar. 15, 1998, 58: 1208-1216.
Dauer et al., "Mature Dendritic Cells Derived from Human Monocytes Within 48 Hours: A Novel Strategy for Dendritic Cell Differentiation from Blood Precursors", The Journal of Immunology, 2003, 170: 4069-4076.

(56) References Cited

OTHER PUBLICATIONS

Hellmann et al., "Nivolumab plus ipilimumab as first-line treatment for advanced non-small-cell lung cancer (CheckMate 012): results of an open-label, phase 1, multicohort study", Lancet Oncol., Jan. 2017, 18:31-41.
Zhu et al., "IL-10 Mediates Sigma Receptor-Dependent Suppression of Antitumor Immunity", The Journal of Immunology, Apr. 2003, 170: 3585-3591.
Horn et al., "Nivolumab Versus Docetaxel in Previously Treated Patients With Advanced Non-Small-Cell Lung Cancer: Two-Year Outcomes From Two Randomized, Open-Label, Phase III Trials (CheckMate 017 and CheckMate 057)", Journal of Clinical Oncology, Dec. 10, 2017, 35(35): 3924-3933.
Torre et al., "Lung Cancer Statistics", Advances in Experimental Medicine and Biology 893, 2016, DOI 10.1007/978-3-319-24223-1_1.
Riedl et al., "Overexpression of CCL-21/Secondary Lymphoid Tissue Chemokine in Human Dendritic Cells Augments Chemotactic Activities for Lymphocytes and Antigen Presenting Cells", Molecular Cancer, Nov. 2, 2003, 2:35, 13 pages.
Arthur et al., "A comparison of gene transfer methods in human dendritic cells", Cancer Gene Therapy, Jan.-Feb. 1997; 4(1):17-25, abstract.
Kim et al., "IL-10 production in cutaneous basal and squamous cell carcinomas. A mechanism for evading the local T cell immune response", J. Immunol., 1995; 155: 2240-2247.
Koivunen et al., "EML4-ALK Fusion Gene and Efficacy of an ALK Kinase Inhibitor in Lung Cancer", Clinical Cancer Research, Jul. 1, 2008; 14(3): 4275-4283.
Brahmer et al., "Clinical activity and biomarkers of MEDI4736, an anti-PD-L1 antibody, in patients with NSCLC", American Society of Clinical Oncology Meeting, 2014, J. Clin. Oncol., 32-5s, supplemental abstract 8021.
Hromas et al., "Isolation and characterization of Exodus-2, a novel C—C chemokine with a unique 37-amino acid carboxyl-terminal extension", J. Immunol., 1997; 159: 2554-2558.
Yoshino et al., "HER2/neu-derived Peptides Are Shared Antigens among Human Non-Small Cell Lung Cancer and Ovarian Cancer", Cancer Research, Jul. 1, 1994; 54: 3387-3390.
Hedrick et al., "Identification and characterization of a novel beta chemokine containing six conserved cysteines", J. Immunol., 1997; 159: 1589-1593.
Heery et al., "Phase I open-label, multiple ascending dose trial of MSB0010718C, an anti-PD-L1 monoclonal antibody, in advanced solid malignancies", Journal of Clinical Oncology, 2014, vol. 32, Issue 15 suppl., abstract.
Guenova et al., "IL-4-mediated fine tuning of IL-12p70 production by human DC", Eur. J. Immunol., Nov. 2008, 38: 3138-3149.
Rittmeyer et al., "Atezolizumab versus docetaxel in patients with previously treated non-small-cell lung cancer (OAK): a phase 3, open-label, multicentre randomised controlled trial", Lancet, Jan. 21, 2017; 389: 255-265.
Langer et al., "Carboplatin and pemetrexed with or without pembrolizumab for advanced, non-squamous non-small-cell lung cancer: a randomised, phase 2 cohort of the open-label KEYNOTE-021 study", Lancet Oncol., Nov. 2016; 17: 1497-1508.
Koya et al., "BRAF Inhibitor Vemurafenib Improves the Antitumor Activity of Adoptive Cell Immunotherapy", Cancer Research, Aug. 15, 2012; 72(16): 3928-3937.
Cerundolo et al., "Dendritic cells: a journey from laboratory to clinic", Nature Immunology, Jan. 2004, 5(1): 7-10.
Garg et al., "Trial watch: Dendritic cell-based anticancer immunotherapy", OncoImmunology, Jun. 2017, 6:7, e1328341, 17 pages, https://doi.org/10.1080/2162402X.2017.1328341.
Constantino et al., "Dendritic cell-based immunotherapy: a basic review and recent advances", Immunol. Res., Aug. 2017, 65: 798-810.
Banchereau et al., "Dendritic cells and the control of immunity", Nature, Mar. 19, 1998; 392: 245-252.
Butterfield et al., "New approaches to the development of adenoviral dendritic cell vaccines in melanoma", Curr. Opin. Investig. Drugs, Dec. 2010; 11(12): 1399-1408.
Riley, "PD-1 signaling in primary T cells", Immunological Reviews, May 2009, 229: 114-125.
Gallo et al., "Adenovirus as vehicle for anticancer genetic immunotherapy", Gene Therapy, Oct. 2005, 12, Suppl 1, S84-S91.
Baratelli et al., "$PGE_2$ contributes to TGF-β induced T regulatory cell function in human non-small cell lung cancer", Am. J. Transl. Res., Jun. 2010; 2(4): 356-367.
Newman et al., "Robust enumeration of cell subsets from tissue expression profiles", Nat. Methods, May 2015; 12(5): 453-457.
Mehrara et al., "Quantitative analysis of tumor growth rate and changes in tumor marker level: Specific growth rate versus doubling time", Acta Oncologica, 48(4): 591-597.

* cited by examiner

FIG. 3A
FIG. 3B
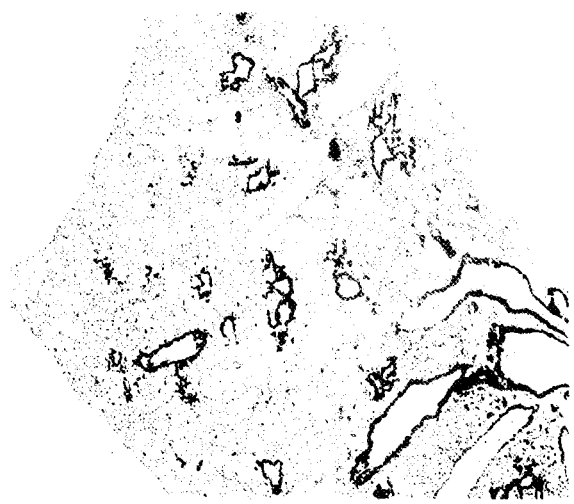
FIG. 3C
FIG. 3D
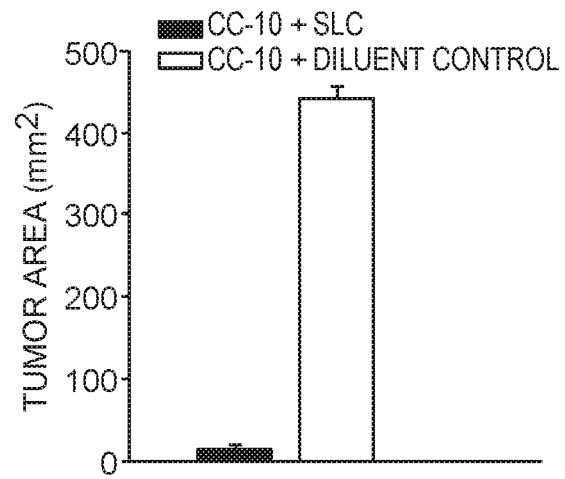
FIG. 3E

FIG. 4B

| Treatment | # of mice with complete tumor eradication after therapy |
|---|---|
| L1C2 control + no treatment | 0/8 |
| L1C2 + intratumoral $10^8$ pfu Ad-CV | 0/8 |
| L1C2 + intratumoral $10^8$ pfu Ad-SLC | 5/8 |

FIG. 5A
Table 1A

| Groups | PGE2 | VEGF | IFN-γ | GM-CSF | IL-10 | IL-12 | TGF-β | MIG | IP-10 |
|---|---|---|---|---|---|---|---|---|---|
| 3LL + diluent | 28,510 ± 400 | 757 ± 26 | 104 ± 15 | <5 | 244 ± 6 | 24 ± 6 | 5,820 ± 578 | 1,000 ± 200 | 15,100 ± 1,100 |
| 3LL + SLC | 8,737 ± 210* | 222 ± 34* | 549 ± 16* | 56 ± 11 | 42 ± 13* | 42 ± 1* | 2,473 ± 26* | 6,600 ± 100* | 39,400 ± 2,300* |

*$p<0.01$ compared with diluent-treated tumor-bearing mice. $n = 6$ mice/group.

FIG. 5B
Table 1B

| Group | PGE-2 | VEGF | IL-10 | IFN-γ | GM-CSF | IL-12 | MIG | IP-10 | TGF-β |
|---|---|---|---|---|---|---|---|---|---|
| Lung | | | | | | | | | |
| CC-10 + diluent | 12419 ± 384 | 980 ± 38 | 213 ± 11 | 26 ± 5 | 74 ± 5 | 110 ± 8 | 47.8 ± 5 | 108 ± 6 | 281 ± 0 |
| CC-10 + SLC | 11945 ± 208 | 222 ± 53$^a$ | 239 ± 20 | 4174 ± 26$^a$ | 611 ± 11$^a$ | 235 ± 15$^a$ | 98.4 ± 4 | 187 ± 2$^a$ | 154 ± 15$^a$ |
| FVB control | 6023 ± 40 | 222 ± 53 | 129 ± 8 | 122 ± 28 | 73 ± 3 | 167 ± 7 | 72.3 ± 6 | 57 ± 5 | 118 ± 9 |
| Splenocytes | | | | | | | | | |
| FVB control mice | 72 ± 2 | 107 ± 36 | 85 ± 0 | 101 ± 24 | 44 ± 1 | 66 ± 8 | 89 | 96 ± 5 | 20 ± 2 |
| Diluent-treated CC-10 | 643 ± 51 | 267 ± 14 | 87 ± 11 | 106 ± 3 | 45 ± 3 | 67 ± 6 | 42 | 63 ± 3 | <15 |
| SLC-treated CC-10 | 44 ± 10$^a$ | 13 ± 1$^a$ | 84 ± 11 | 107 ± 9 | 110 ± 4$^a$ | 137 ± 5$^a$ | 142$^a$ | 216 ± 5$^a$ | 17 ± 5 |
| Lymph node | | | | | | | | | |
| FVB control mice | 148 ± 3 | 204 ± 18 | 78 ± 6 | 98 ± 23 | 65 ± 2 | 195 ± 5 | 70 | <15 | 102 ± 4 |
| Diluent-treated CC-10 | 94 ± 3 | 142 ± 12 | 81 ± 4 | 89 ± 9 | 42 ± 2 | 95 ± 10 | 46 | 43 ± 3 | 139 ± 6 |
| SLC-treated CC-10 | 113 ± 4 | 221 ± 32 | 86 ± 20 | 192 ± 8$^a$ | 44 ± 3 | 233 ± 6$^a$ | 106$^a$ | 100 ± 2$^a$ | 89 ± 7$^a$ |

$^a P<0.01$ compared to diluent-treated CC-10 tumor-bearing mice.

FIG. 6A
TABLE 2A

| Groups | CD4 | | | | CD8 | | | | | |
|---|---|---|---|---|---|---|---|---|---|---|
| | IFN-γ | | GM-CSF | | IFN-γ | | GM-CSF | | CD11c + DEC205 | |
| | % | MCF | % | MCF | % | MCF | % | MCF | % | MCF |
| Tumor | | | | | | | | | | |
| 3LL | 3.6 | 193 | 4.8 | 31 | 1.9 | 389 | 1.7 | 44 | 4 | 103 |
| 3LL + SLC | 7.4* | 187 | 5.3 | 52* | 3.2* | 306 | 2.7* | 47 | 13* | 108 |
| LN | | | | | | | | | | |
| 3LL | 0.9 | 86 | 0.8 | 50 | 0.9 | 131 | 0.5 | 78 | 32 | 79 |
| 3LL + SLC | 1.7* | 340* | 1.2* | 181* | 1.7* | 181 | 1.3* | 107* | 40* | 118* |

*; $p<0.01$ (n = 6 mice/group)

FIG. 6B
TABLE 2B

| Groups | CD4+ | | | | CD8+ | | | | CD11c+DEC205 | |
|---|---|---|---|---|---|---|---|---|---|---|
| | IFN-γ | | GMF-CSF | | IFN-γ | | GM-CSF | | | |
| | % | MCF | % | MCF | % | MCF | % | MCF | % | MCF(DEC205) |
| Tumor | | | | | | | | | | |
| CC-10 + diluent | 2 | 124 | 2.4 | 38 | 2 | 307 | 1.5 | 53 | 3.2 | 121 |
| CC-10 + SLC | 5$^a$ | 187 | 5.2$^a$ | 89 | 5.3$^a$ | 311 | 3.7 | 89 | 11.7$^a$ | 132 |
| Lymph node | | | | | | | | | | |
| CC-10 + diluent | 3.2 | 154 | 3.3 | 80 | 1 | 200 | 1.3 | 52 | 5.3 | 54.4 |
| CC-10 + SLC | 6.8$^a$ | 173 | 5.7$^a$ | 102 | 6.8$^a$ | 244.9$^a$ | 3$^a$ | 55 | 12.7$^a$ | 79 |
| Spleen | | | | | | | | | | |
| CC-10 + diluent | 3.9 | 163 | 1.5 | 60 | 1.1 | 311 | 0.7 | 88 | 5.9 | 82 |
| CC-10 + SLC | 4.7 | 206$^a$ | 1.6 | 168$^a$ | 3.8$^a$ | 352 | 2.1$^a$ | 54 | 11.4$^a$ | 101 |

$^a$ $P<0.01$, $n$ = six mice/group. For DC staining, MCF (mean channel fluorescence) is noted for DEC205. Experiments were repeated twice.

FIG. 7A
TABLE 3A

| Group | IFN-γ | GM-CSF | IL-10 | IL-12 |
|---|---|---|---|---|
| Splenocytes | | | | |
| Mice without tumor, constitutive | 220±30 | 0 | 0 | 78±1 |
| Stimulated with 3LL | 85±19 | 37±2 | 0 | 16±3 |
| Diluent-treated, constitutive | 117±41 | 0 | 18±1 | 60±12 |
| Stimulated with 3LL | 97±13 | 23±9* | 1566±93 | 51±1 |
| SLC-treated, constitutive | 113±21 | 0 | 16±1 | 111±1 |
| Stimulated with 3LL | 2731±99* | 71±2* | 181±14* | 206±7* |
| Lymph node | | | | |
| Mice without tumor, constitutive | 248±1 | 16±1 | 0 | 60±1 |
| Stimulated with 3LL | 87±12 | 34±7 | 0 | 48±1 |
| Diluent-treated, constitutive | 166±16 | 16±1 | 297±10 | 25±1 |
| Stimulated with 3LL | 96±17 | 52±8 | 816±25 | 84±6 |
| SLC-treated, constitutive | 256±10 | 19±1 | 0 | 25±1 |
| Stimulated with 3LL | 1242±270* | 49±6 | 133±17* | 108±3* |

*$p<0.01$ compared with diluent-treated mice and SLC constitutive levles: $n^4$=6 mice/group.

FIG. 7B
TABLE 3B

| Group | IFN-γ | GM-CSF | IL-10 |
|---|---|---|---|
| No tumor | | | |
| Mice without tumor, constitutive | 634 ± 45 | 55 ± 7 | 32 ± 4 |
| Stimulated with CC-10 cells | 685 ± 39 | 87 ± 5 | 147 ± 8 |
| Diluent-treated | | | |
| Diluent-treated, constitutive | 400 ± 38 | 104 ± 11 | 78 ± 2 |
| Stimulated with CC-10 cells | 379 ± 28 | 132 ± 5 | 1000 ± 69 |
| SLC-treated | | | |
| SLC-treated, constitutive | 617 ± 42 | 185 ± 3 | 49 ± 2 |
| Stimulated with CC-10 cells | $2265 \pm 107^{\alpha}$ | $287 \pm 10^{\alpha}$ | $200 \pm 7\alpha$ |

COMBINATION IMMUNOTHERAPY

RELATED APPLICATIONS

This application claims the priority benefit of U.S. Provisional Patent Application No. 62/075,532, filed Nov. 5, 2014, the contents of which are incorporated herein by reference.

GOVERNMENT SUPPORT

This work was supported by the U.S. Department of Veterans Affairs, and the Federal Government has certain rights in the invention.

FIELD OF THE INVENTION

The present invention relates to methods of using secondary lymphoid organ chemokine to modulate mammalian physiological processes including those associated with pathological conditions such as cancer.

BACKGROUND OF THE INVENTION

Understanding the immune mechanisms that influence oncogenesis, cancer regression, recurrence and metastasis is a crucial aspect of the development of new immunotherapies. In this context, artisans understand that a fundamental aspect of an immune response is the ability of an organism's immune cells to distinguish between self and non-self antigens. Consequently, clinically relevant models which seek to dissect immune mechanisms in cancer must take into account the fact that tumor cells share a genetic background with cells of the host immune system (i.e. are syngeneic). Unfortunately, many animal models of cancer which introduce cancer cell lines into an animal are confounded by immune responses that are influenced by differences between the genetic background of the host animal and the cancer cell lines that are being evaluated. Specifically, in cancer models in which host animals and cancer cell lines do not share an essentially identical genetic background, there are a variety of problems including those associated with "non-self" immune responses by the host's immune system that are akin to those seen in the rejection of transplanted organs between individuals. The non-self immune responses that can result from the host immune system's recognition of non-self antigens on autogeneic cancer cells (a phenomena which understandably does not occur in cancers), create an immune response to cancer cells that does not occur in human cancers. Therefore, there is an ongoing need for cancer models which faithfully mimic the development and progression of cancer so that clinically relevant analyses of immune mechanisms can be performed.

Effective immune responses to tumor cells require both APCs and lymphocyte effectors (see, e.g. Huang et al., Science, 264: 961-965, 1994). Because tumor cells often have limited expression of MHC antigens and lack costimulatory molecules, they are ineffective APCs (see, e.g. Restifo et al., J. Exp. Med., 177: 265-272, 1993). In addition, tumor cells secrete immunosuppressive mediators that contribute to evasion of host immune surveillance (see, e.g. Huang et al., Cancer Res., 58: 1208-1216, 1998; Sharma et al., J. Immunol., 163: 5020-5028, 1999; and Uzzo et al., J. Clin. Investig., 104: 769-776, 1999). To circumvent this problem, investigators are using ex vivo generated DCs to stimulate antitumor immune responses in vivo. In experimental murine models, DCs pulsed with tumor-associated antigenic peptides (Nair et al., Eur. J. Immunol., 27: 589-597, 1997) or transfected with tumor RNA have been shown to induce antigen-specific antitumor responses in vivo (Boczkowski et al., J. Exp. Med., 184:465-472, 1996). Similarly, fusion of DCs with tumor cells or intratumoral injection of cytokine-modified DCs has also been shown to enhance antitumor immunity (Gong et al., Nat. Med., 3: 558-561, 1997; Celluzzi et al., J. Immunol., 160: 3081-3085, 1998; Miller et al., Hum. Gene Ther., 11:53-65, 2000). Consequently, it has been suggested that effective anticancer immunity may be achieved by recruiting professional host APCs for tumor antigen presentation to promote specific T-cell activation (Soto et al., Annu. Rev. Immunol., 15: 675-705, 1997). Thus, chemokines that attract both DCs and lymphocyte effectors to lymph nodes and tumor sites could serve as potent agents in cancer immunotherapy.

Chemokines, a group of homologous, yet functionally divergent proteins, directly mediate leukocyte migration and activation and playa role in regulating angiogenesis (Baggiolini et al., Rev. Immunol., 15: 675-705, 1997). Chemokines also function in maintaining immune homeostasis and secondary lymphoid organ architecture (Jung et al., Curr. Opin. Immunol., 11: 319-325, 1999). Several chemokines are known to have antitumor activity. Tumor rejection has been noted in various murine tumor models in which tumor cells have been modified with chemokines including MIP1α, RANTES, lymphotactin, TCA3, JE/MCP-1/MCAF, MIP3α, MIP3β, and IP-10 (Luster et al., J. Exp. Med., 178: 1057-1065, 1993; Bottazzi et al., J. Immunol., 148: 1280-1285, 1992; Kellermann et al., J. Immunol., 162: 3859-3864, 1999; Sallusto et al., Eur. J. Immunol., 28: 2760-2769, 1998; Sozzani et al., J. Immunol., 161: 1083-1086, 1998; Dieu et al., J. Exp. Med., 188: 373-386, 1998; Campell et al., J. Cell Biol., 141: 1053-1059, 1998; Saeki et al., J. Immunol., 162: 2472-2475, 1999; Nagira et al., Eur. J. Immunol., 28: 1516-1523, 1998).

Secondary lymphoid tissue chemokine (SLC, also referred to as Exodus 2 or 6Ckine) is a high endothelial-derived CC chemokine normally expressed in high endothelial venules and in T-cell zones of spleen and lymph node, that strongly attracts naive T cells and DCs (Cyster et al., J. Exp. Med., 189: 447-450, 1999.24; Ogata et al., Blood, 93: 3225-3232, 1999; Chan et al., Blood, 93: 3610-3616, 1999; Hedrick et al., J. Immunol., 159: 1589-1593, 1997; Hromas et al., J. Immunol., 159: 2554-2558, 1997; Nagira et al., J. Biol. Chem., 272: 19518-19524, 1997; Tanabe et al., J. Immunol., 159: 5671-5679, 1997; Willimann et al., Eur. J. Immunol., 28: 2025-2034, 1998). SLC mediates its effects through two specific G protein-coupled seven-transmembrane domain chemokine receptors, CCR7 and CXCR3 (Yoshida et al., J. Biol. Chem. 273:7118; Jenh et al., J. Immunol. 162:3765). Whereas CCR7 is expressed on naive T cells and mature DC, CXCR3 is expressed preferentially on Th1 cytokine-producing lymphocytes with memory phenotype (Yoshida et al., J. Biol. Chem. 273:7118; Jenh et al., J. Immunol. 162:3765).

The capacity of SLC to chemoattract DCs (Kellermann et al., J. Immunol., 162: 3859-3864, 1999) is a property shared with other chemokines (Sallusto et al., Eur. J. Immunol., 28: 2760-2769, 1998; Sozzani et al., J. Immunol., 161: 1083-1086, 1998; Dieu et al., J. Exp. Med., 188: 373-386, 1998). However, SLC may be distinctly advantageous because of its capacity to elicit a Type 1 cytokine response invivo (Sharma et al., J. Immunol., 164: 4558-4563, 2000). DCs are uniquely potent APCs involved in the initiation of immune responses (Banchereau et al., Nature (Lond.), 392: 245-252, 1998). Serving as immune system sentinels, DCs are responsible for Ag acquisition in the periphery and subsequent transport to T-cell areas in lymphoid organs where they prime specific immune responses. SLC recruits both naive lymphocytes and antigen stimulated DCs into T-cell zones of secondary lymphoid organs, colocalizing these early immune response constituents and culminating in cognate T-cell activation (Cyster et al., J. Exp. Med., 189: 447-450, 1999.24).

There is a need in the art for cancer models that faithfully mimic immune mechanisms in cancer in order to examine, for example how host cytokine profiles are modulated by SLC as well as the capacity of SLC to orchestrate effective cell-mediated immune responses to syngeneic cancer cells. In addition, there is a need for new assays of immune function as well as immunotherapeutic modalities based on such clinically relevant models. The disclosure provided herein meets these needs.

SUMMARY OF THE INVENTION

The invention disclosed herein provides animal models which faithfully mimic immune mechanisms in cancer by utilizing host animals and cancer cells that have an essentially identical genetic background. These models are used to demonstrate the capacity of SLC to orchestrate effective cell-mediated immune responses to syngeneic cancer cells. In addition, these models can be used to evaluate host cytokine profiles that are associated with SLC modulated immune responses to syngeneic cancer cells.

As disclosed herein, the antitumor efficiency of secondary lymphoid organ chemokine was evaluated in a number of syngeneic models including transgenic mice that spontaneously develop tumors. In these transgenic mice, bilateral multifocal pulmonary adenocarcinomas develop in an organ-specific manner. As compared with allogeneic models known in the art, the spontaneous tumors that arise in this transgenic mouse model do not expresses non-self antigens and therefore resemble human cancers.

In the syngeneic models disclosed herein, injection of recombinant SLC intratumorally and/or in the axillary lymph node region led to a marked reduction in tumor burden with extensive lymphocytic and DC infiltration of the tumors and enhanced survival. SLC injection in these syngeneic murine models led to significant increases in CD4 and CD8 lymphocytes as well as DC at the tumor sites, lymph nodes, and spleen. The cellular infiltrates were accompanied by the enhanced elaboration of Type 1 cytokines and the antiangiogenic chemokines IFN-γ inducible protein 10, and monokine induced by IFN-γ (MIG). In contrast, lymph node and tumor site production of the immunosuppressive cytokine transforming growth factor 13 was decreased in response to SLC treatment. In vitro, after stimulation with irradiated autologous tumor, splenocytes from SLC-treated mice secreted significantly more IFN-γ and granulocyte macrophage colony-stimulating factor, but reduced levels of interleukin 10. Significant reduction in tumor burden in a model in which tumors develop in an organ-specific manner provides methods for the use of SLC in the regulation of tumor immunity and cancer immunotherapy.

The invention disclosed herein has a number of embodiments. A typical embodiment of the invention is a method of inhibiting the growth of a spontaneous cancer in a mammal by administering to the mammal an amount of secondary lymphoid tissue chemokine (SLC) polypeptide sufficient to inhibit the growth of the cancer cells. In preferred methods the SLC has the polypeptide sequence shown in SEQ ID NO: 1. In these methods SLC polypeptide is typically administered to a mammal sytemically, via intratumoral injection or via intra-lymph node injection. In yet another mode of administration, an expression vector having a polynucleotide encoding a SLC polypeptide is administered to the mammal and the SLC polypeptide is produced by a mammalian cell transduced with the SLC expression vector.

A related embodiment of the invention is a method of inhibiting the growth of syngeneic cancer cells (most preferably spontaneous cancer cells) in a mammal comprising administering secondary lymphoid tissue chemokine (SLC) to the mammal; wherein the SLC is administered to the mammal by transducing the cells of the mammal with a polynucleotide encoding the SLC shown in SEQ ID NO: 1 such that the transduced cells express the SLC polypeptide in an amount sufficient to inhibit the growth of the cancer cells. Preferably the vector is administered to a mammal systemically, via intratumoral injection or via intra-lymph node injection.

Another embodiment of the invention is a method of effecting or modulating cytokine expression (e.g. changing an existing cytokine profile) in a mammal or in a population of cells derived from a mammal by exposing the population of cells to an amount of secondary lymphoid tissue chemokine (SLC) polypeptide sufficient to inhibit the growth of syngeneic tumor cells. As disclosed herein, because the syngeneic models disclosed herein demonstrate how the addition of SLC coordinately modulates cytokine expression and inhibits the growth of the tumor cells, observations of these phenomena (modulation of cytokine expression and inhibition of tumor growth) can be used in cell based assays designed to assess the effects of potential immunostimulatory or immunoinhibitory test compounds.

Another embodiment of the invention is a method of effecting an increase in the expression of Interferon-γ (IFN-γ) polypeptide and a decrease in the expression of Transforming Growth Factor-β (TGF-β) polypeptide in a population of syngeneic mammalian cells including CD8 positive T cells, CD4 positive T cells, Antigen Presenting Cells and tumor cells by exposing the population of cells to an amount of secondary lymphoid tissue chemokine (SLC) polypeptide sufficient to inhibit the growth of the tumor cells. In preferred methods, the increase in the expression of Interferon-γ (IFN-γ) polypeptides is at least about two-fold and a decrease in the expression of Transforming Growth Factor-β (TGF-β) polypeptides is at least about two-fold as measured by an enzyme linked immunoadsorbent (ELISA) assay.

In various embodiments, the disclosure also provides a method of treating cancer or a solid tumor in a subject comprising, administering to the subject (i) a SLC polypeptide, (ii) a polynucleotide encoding the SLC polypeptide, (iii) a cell comprising the polynucleotide, or (iv) a combination thereof, and administering to the subject an immune checkpoint inhibitor whereupon the cancer or solid tumor is treated in the subject.

Also contemplated are methods of reducing tumor growth or tumor volume, methods of slowing or reducing tumor progression, or methods of preventing or ameliorating tumor recurrence in a subject comprising, administering to the subject (i) a SLC polypeptide, (ii) a polynucleotide encoding the SLC polypeptide, (iii) a cell comprising the polynucleotide, or (iv) a combination thereof, and administering to the subject an immune checkpoint inhibitor.

In various embodiments, the immune checkpoint inhibitor is selected from the group consisting of a CTLA-4 inhibitor, a CTLA-4 receptor inhibitor, a programmed cell death 1 (PD-1) inhibitor, a PD1-L1 inhibitor, a PD1-L2 inhibitor, a 4-1BB inhibitor, an OX40 inhibitor, a lymphocyte-activation gene 3 (LAG-3) inhibitor, a T-cell immunoglobulin and mucin domain 3 (TIM-3) inhibitor, or a combination thereof.

In various embodiments, the immune checkpoint inhibitor is an antibody, optionally, a monoclonal antibody, specific for one or more of CTLA-4, a CTLA-4 receptor, PD-1, PD1-L1, PD1-L2, 4-1BB, OX40, LAG-3, TIM-3, or a combination thereof.

In various embodiments, the immune checkpoint inhibitor is a small molecule inhibitor that inhibits the activity of one or more of CTLA-4, a CTLA-4 receptor, PD-1, PD1-L1, PD1-L2, 4-1BB, OX40, LAG-3, TIM-3, or a combination thereof.

In various embodiments, the immune checkpoint inhibitor is a CTLA-4 inhibitor, optionally, ipilimumab or tremilimumab.

In various embodiments, the immune checkpoint inhibitor is a PD1 inhibitor selected from a group consisting of: Nivolumab, Pembrolizumab, Pidilizumab, Lambrolizumab, BMS-936559, Atezolizumab, and AMP-224, AMP224, AUNP12, BGB108, MCLA134, MEDI0680, PDR001, REGN2810, SHR1210, STIA110X, STIA1110 and TSR042.

In various embodiments, the immune checkpoint inhibitor is a PD1-L1 inhibitor selected from a group consisting of: BMS-936559, MPDL3280A, MEDI-4736, MSB0010718C, ALN-PDL, BGBA317, KD033, KY1003, STIA100X, STIA1010, STIA1011, STIA1012 and STIA1014.

In various embodiments, the immune checkpoint inhibitor of 4-1BB is a monoclonal antibody that specifically binds to 4-1BB, including, but not limited to BMS-663513 and PF-05082566.

In various embodiments, the immune checkpoint inhibitor is an inhibitor of OX40. In exemplary aspects, the inhibitor of OX40 is a monoclonal antibody that specifically binds to OX40.

In various embodiments, the SLC polypeptide comprises an amino acid sequence of SEQ ID NO: 1 or SEQ ID NO: 2.

In various embodiments, the polynucleotide encoding the SLC polypeptide is inserted into a vector and the vector is administered to the subject. In various embodiments, the vector is an adenoviral vector. In various embodiments, the adenoviral vector is a replication-deficient adenoviral vector.

In various embodiments, the cell comprising the polynucleotide encoding the SLC polypeptide is an antigen presenting cell (APC). In various embodiments, the APC is a dendritic cell. In various embodiments, the dendritic cell is autologous to the subject.

In various embodiments, at least or about $1 \times 10^6$ cells comprising the polynucleotide encoding the SLC polypeptide are administered to the subject. In various embodiments, the cells produce at least or about 0.25 ng of CCL21 per $1 \times 10^6$ cells in a 24-hour period.

In various embodiments, the subject comprises a solid tumor and the cells are administered to the subject intratumorally. In various embodiments, the solid tumor is a non-small cell lung carcinoma (NSCLC) solid tumor.

In various embodiments, the (i) SLC polypeptide, (ii) polynucleotide encoding the SLC polypeptide, (iii) cell comprising the polynucleotide, or (iv) combination thereof, is administered to the subject prior to the immune checkpoint inhibitor. In various embodiments, the (i) SLC polypeptide, (ii) polynucleotide encoding the SLC polypeptide, (iii) cell comprising the polynucleotide, or (iv) combination thereof, is administered to the subject about 2 weeks prior to the immune checkpoint inhibitor.

In various embodiments, the (i) SLC polypeptide, (ii) polynucleotide encoding the SLC polypeptide, (iii) cell comprising the polynucleotide, or (iv) combination thereof, is administered to the subject more than once.

In various embodiments, the (i) SLC polypeptide, (ii) polynucleotide encoding the SLC polypeptide, (iii) cell comprising the polynucleotide, or (iv) combination thereof, is administered to the subject once a month.

In various embodiments, the immune checkpoint inhibitor is administered to the subject more than once. In various embodiments, the immune checkpoint inhibitor is administered to the subject once every 2 weeks.

Also contemplated is a kit comprising (i) a SLC polypeptide, (ii) a polynucleotide encoding the SLC polypeptide, (iii) a cell comprising the polynucleotide, or (iv) a combination thereof, and an immune checkpoint inhibitor.

In various embodiments, the kit provides an immune checkpoint inhibitor selected from the group consisting of a CTLA-4 inhibitor, a CTLA-4 receptor inhibitor, a PD-1 inhibitor, a PD1-L1 inhibitor, a PD1-L2 inhibitor, a 4-1BB inhibitor, an OX40 inhibitor, a LAG-3 inhibitor, a TIM-3 inhibitor, or a combination thereof.

In various embodiments, the immune checkpoint inhibitor is an antibody, optionally, a monoclonal antibody, specific for one or more of CTLA-4, a CTLA-4 receptor, PD-1, PD1-L1, PD1-L2, 4-1BB, OX40, LAG-3, TIM-3, or a combination thereof.

In various embodiments, the immune checkpoint inhibitor is a small molecule inhibitor that inhibits the activity of one or more of CTLA-4, a CTLA-4 receptor, PD-1, PD1-L1, PD1-L2, 4-1BB, OX40, LAG-3, TIM-3, or a combination thereof.

In various embodiments, the immune checkpoint inhibitor in the kit is a CTLA-4 inhibitor, optionally, ipilimumab or tremilimumab.

In various embodiments, the immune checkpoint inhibitor in the kit is a PD1 inhibitor selected from a group consisting of: Nivolumab, Pembrolizumab, Pidilizumab, Lambrolizumab, BMS-936559, Atezolizumab, and AMP-224, AMP224, AUNP12, BGB108, MCLA134, MEDI0680, PDR001, REGN2810, SHR1210, STIA110X, STIA1110 and TSR042.

In various embodiments, the immune checkpoint inhibitor is the kit a PD1-L1 inhibitor selected from a group consisting of: BMS-936559, MPDL3280A, MEDI-4736, MSB0010718C, ALN-PDL, BGBA317, KD033, KY1003, STIA100X, STIA1010, STIA1011, STIA1012 and STIA1014.

In various embodiments, the immune checkpoint inhibitor of 4-1BB is a monoclonal antibody that specifically binds to 4-1BB, including, but not limited to BMS-663513 and PF-05082566.

In various embodiments, the immune checkpoint inhibitor is an inhibitor of OX40. In various embodiments, the inhibitor of OX40 is a monoclonal antibody that specifically binds to OX40.

In various embodiments, the checkpoint inhibitor is a LAG-3 inhibitor. In various embodiments, the inhibitor of LAG-3 is a monoclonal antibody that specifically binds to LAG-3.

In various embodiments, the checkpoint inhibitor is a TIM-3 inhibitor. In various embodiments, the inhibitor of TIM-3 is a monoclonal antibody that specifically binds to TIM-3.

In various embodiments, the SLC polypeptide comprises an amino acid sequence of SEQ ID NO: 1 or SEQ ID NO: 2.

In various embodiments, the polynucleotide encoding the SLC polypeptide is inserted into a vector and the vector is administered to the subject. In various embodiments, the vector is an adenoviral vector. In various embodiments, the adenoviral vector is a replication-deficient adenoviral vector.

Also contemplated is use of SLC (e.g., a SLC polypeptide, a polynucleotide encoding the SLC polypeptide, a cell comprising the polynucleotide, or a combination thereof) and/or any of the foregoing antibodies or polypeptides described herein that modulate checkpoint protein signaling, e.g., a checkpoint inhibitor, such as a CTLA-4 inhibitor, a CTLA-4 receptor inhibitor, a programmed cell death 1 (PD-1) inhibitor, a PD1-L1 inhibitor, a PD1-L2 inhibitor, a 4-1BB inhibitor, an OX40 inhibitor, a lymphocyte-activation gene 3 (LAG-3) inhibitor, a T-cell immunoglobulin and mucin domain 3 (TIM-3) inhibitor, or a combination thereof, in preparation of a medicament for treatment of any of the disorders described herein. In various embodiments, the immune checkpoint inhibitor is an antibody, optionally, a monoclonal antibody, specific for one or more of CTLA-4, a CTLA-4 receptor, PD-1, PD1-L1, PD1-L2, 4-1BB, OX40, LAG-3, TIM-3, or a combination thereof.

Syringes, e.g., single use or pre-filled syringes, sterile sealed containers, e.g. vials, bottle, vessel, and/or kits or packages comprising any of the foregoing antibodies or polypeptides, optionally with suitable instructions for use, are also contemplated.

Any of the foregoing antibodies or polypeptides described herein may be concurrently administered with any chemotherapeutic agents known in the art or described herein, as adjunct therapy. Compositions comprising any of the foregoing antibodies or polypeptides of the invention together with a chemotherapeutic agent are also contemplated.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the invention. Similarly, where a method describes identifying polypeptide binding agents, such as antibodies, characterized by certain features, polypeptide binding agents characterized by those features are also contemplated by the invention. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE FIGURES

FIGS. 3A-3E. SLC mediates potent antitumor responses in a murine model of spontaneous lung cancer. The antitumor efficacy of SLC was evaluated in the spontaneous bronchogenic carcinoma model in transgenic mice in which the SV40 large T Ag is expressed under control of the murine Clara cell-specific promoter, CC-10 (Gabrilovich et al., Blood, 92: 4150-4166, 1998). Mice expressing the transgene develop diffuse bilateral bronchoalveolar carcinoma and have an average lifespan of 4 months. SLC (0.5 μg/injection) or the same concentration of murine serum albumin was injected in the axillary lymph node region of 4-week-old transgenic mice three times a week for 8 weeks. At 4 months when the control mice started to succumb because of progressive lung tumor growth, mice in all of the treatment groups were sacrificed, and their lungs were isolated and embedded in paraffin. H&E staining of paraffin-embedded lung tumor sections from control-treated mice evidenced large tumor masses throughout both lungs without detectable lymphocytic infiltration (3A and 3C). In contrast, the SLC therapy group evidenced extensive lymphocytic infiltration with marked reduction in tumor burden (3B and 3D). Arrows in 3D depict tumor (*1) and infiltrate (*2).(3A and 3B, ×32; 3C and 3D, ×320) 3E, reduced tumor burden in SLC-treated mice. Tumor burden was quantified within the lung by microscopy of H&E-stained paraffin-embedded sections with a calibrated graticule (a 1-cm$^2$ grid subdivided into 100 1-mm$^2$ squares). A grid square with tumor occupying >50% of its area was scored as positive, and the total number of positive squares was determined. Ten separate fields from four histological sections of the lungs were examined under high-power (×20 objective). There was reduced tumor burden in SLC-treated CC-10 mice compared with the diluent-treated control group. Median survival was 18±2 weeks for control-treated mice. In contrast, mice treated with SLC had a median survival of 34±3 weeks. (P<0.001; n=10 mice/group).

FIGS. 4A-4B. Intratumoral administration of Ad-SLC reduces lung cancer growth in vivo. Mice were inoculated with 100,000 L1C2 tumor cells and after 5 days treated intratumorally once a week for three weeks with either $10^8$ pfu of Ad-CV or Ad-SLC. At this MOI, of Ad-SLC, L1C2 tumor cells transduced in vitro secreted 10 ng/ml/$10^6$ cells/24 hr of SLC. The reduction in tumor volume over time is shown in graphic form in FIG. 4A and the number of mice with complete tumor eradication after therapy is shown in table form in FIG. 4B.

FIGS. 5A and 5B show Tables 1A and 1B respectively. Table 1A shows Intratumoral SLC administration promotes Th1 cytokine and antiangiogenic chemokine release and a decline in immunosuppressive mediators. Cytokine profiles in tumors were determined in mice treated intratumorally with SLC and compared with those in diluent-treated control mice bearing tumors. Non-necrotic tumors were harvested, cut into small pieces, and passed through a sieve. Tumors were evaluated for the presence of IL-10, IL-12, GM-CSF, IFN-γ, TGF-β, VEGF, MIG, and IP-10 by ELISA and for $PGE_2$ by EIA in the supernatants after overnight culture. Cytokine, $PGE_2$, and VEGF determinations from the tumors were corrected for total protein by Bradford assay. Results are expressed as picograms per milligram total protein/24 h. Compared with tumor nodules from diluent-treated tumor-bearing controls, mice treated intratumorally with SLC had significant reductions of $PGE_2$, VEGF, IL-10, and TGF-β but an increase in IFN-γ, GM-CSF, IL-12, MIG, and IP-10. Experiments were repeated twice. Table 1B shows how SLC treatment of CC-10 Tag mice promotes Type 1 cytokine and antiangiogenic chemokine release and a decline in the immunosuppressive and angiogenic cytokines TGF-β and VEGF. Following axillary lymph node region injection of SLC, pulmonary, lymph node, and spleen cytokine profiles in CC-10 Tag mice were determined and compared with those in diluent-treated tumor bearing control mice and nontumor bearing syngeneic controls. Lungs were harvested, cut into small pieces, passed through a sieve, and cultured for 24 h. Splenocytes and lymph node-derived lymphocytes ($5 \times 10^6$ cells/ml) were cultured for 24 h. After culture, supernatants were harvested, cytokines quantified by ELISA, and PGE-2 determined by EIA. All determinations from lung were corrected for total protein by Bradford assay, and results are expressed in pg/milligram total protein/24 h. Cytokine and PGE-2 determinations from the spleen and lymph nodes are expressed in pg/ml. Compared with lungs from diluent-treated CC-10 tumor-bearing mice, CC-10 mice treated with SLC had significant reductions in VEGF and TGF-β but a significant increase in IFN-γ, IP-10, IL-12, MIG, and GM-CSF. Compared with diluent-treated CC-10 Tag mice, splenocytes from SLC-treated CC-10 mice had reduced levels of IFN-γ, IP-10, MIG, and IL-12 but decreased TGF-β levels as compared with diluent-treated CC-10 mice. Values given reflect mean±SE for six mice/group.

FIGS. 6A and 6B show Tables 2A and 2B respectively. Table 2A shows that SLC increases the frequency of CD4 and CD8 lymphocyte subsets secreting IFN-γ and GM-CSF and CD11c+DEC205-expressing DC. Single-cell suspensions of tumor nodules and lymph nodes from SLC and diluent-treated tumor-bearing mice were prepared. Intracytoplasmic staining for GM-CSF and IFN-γ and cell surface staining for CD4 and CD8 T lymphocytes were evaluated by flow cytometry. DC that stained positively for cell surface markers CD11c and DEC205 in lymph node and tumor nodule single-cell suspensions were also evaluated. Cells were identified as lymphocytes or DC by gating based on the forward and side scatter profiles: 15,000 gated events were collected and analyzed using Cell Quest software. Within the gated T lymphocyte population, intratumoral injection of SLC led to an increase in the frequency of CD4 and CD8 cells secreting GM-CSF and IFN-γ in the tumor nodules and lymph nodes compared with those of diluent-treated tumor-bearing control mice. Within the gated DC population, there was a significant increase in the frequency of DC in the SLC-treated tumor-bearing mice compared with the diluent-treated control tumor-bearing mice. For DC staining, MCF is for DEC205. MCF, mean channel fluorescence. Experiments were repeated twice. Table 2B shows that SLC treatment of CC-10 Tag mice leads to enhanced dendritic and T cell infiltrations of tumor sites, lymph nodes and spleen. Single-cell suspensions of tumor nodules, lymph nodes, and spleens from SLC and diluent-treated tumor-bearing mice were prepared. Intracytoplasmic staining for GM-CSF and IFN-γ and cell surface staining for CD4 and CD8 T lymphocytes were evaluated by flow cytometry. DCs that stained positive for cell surface markers CD11c and DEC205 in lymph node, tumor nodule, and spleen single-cell suspensions were also evaluated. Cells were identified as lymphocytes or DCs by gating based on the forward and side scatter profiles; 15,000 gated events were collected and analyzed using Cell Quest software. Within the gated T-lymphocyte population from mice treated with SLC, there was an increase in the frequency of CD4+ and CD8+ cells secreting GM-CSF and IFN-γ in the tumor sites, lymph nodes, and spleens compared with those of diluent-treated tumor-bearing control mice. Within the gated DC population, there was a significant increase in the frequency of DCs in the SLC-treated tumor-bearing mice compared with the diluent-treated control tumor-bearing mice.

FIGS. 7A and 7B show Tables 3A and 3B respectively. FIG. 3A shows the specific systemic induction of type 1 cytokines and down-regulation of IL-10 after SLC treatment. Splenic or lymph node-derived lymphocytes ($5 \times 10^6$ cells/ml) were cultured with irradiated 3LL ($10^5$ cells/ml) tumors at a ratio of 50:1 in a total volume of 5 ml. After overnight culture, supernatants were harvested, and GM-CSF, IFN-γ, IL-12, and IL10 were determined by ELISA. After stimulation with irradiated tumor cells, splenocytes and lymph node-derived cells from SLC-treated mice secreted significantly enhanced levels of IFN-γ, GM-CSF, and IL-12 but reduced levels of IL-10 compared with diluent-treated bearing mice. Results are expressed as picograms per milliliter. Experiments were repeated twice. Table 3B shows the systemic induction of type 1 cytokines and downregulation of IL-10 after SLC treatment. Splenic lymphocytes ($5 \times 10^6$ cells/ml) were cultured with irradiated CC-10 ($10^5$ cells/ml) tumors at a ratio of 50:1 in a total volume of 5 ml. After overnight culture, supernatants were harvested and GM-CSF, IFN-γ, and IL-10 were determined by ELISA. After stimulation with irradiated tumor cells, splenocytes secreted significantly more IFN-γ and GM-SCF but reduced levels of IL-10 from SLC-treated mice compared to diluent-treated tumor-bearing mice. Results are expressed in pg/ml ("$P<0.01$ compared with diluent-treated mice as well as SLC-treated constitutive levels). Values given reflect mean±SE for five mice/group.

DETAILED DESCRIPTION OF THE INVENTION

Figure 1:
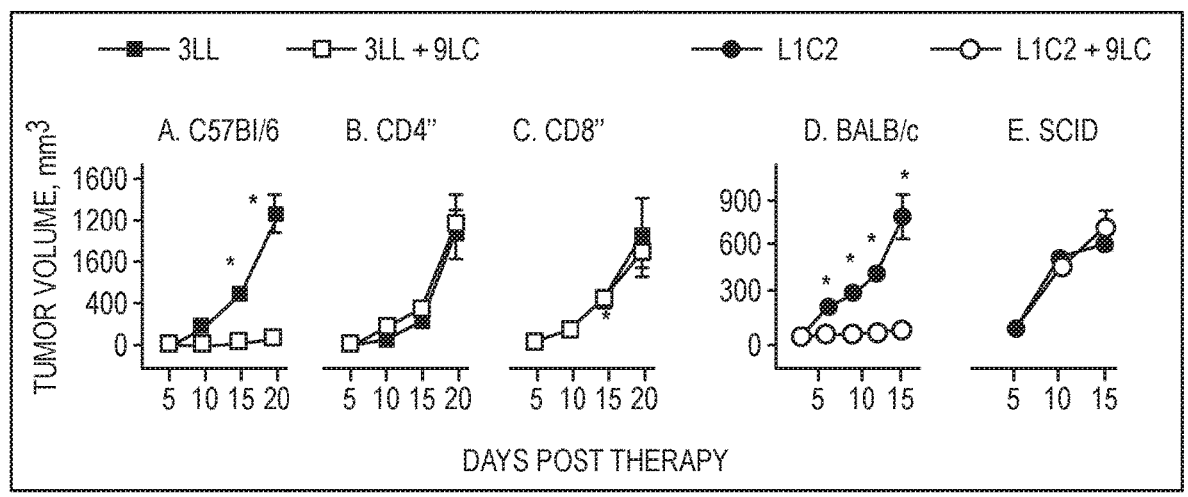
FIG. 1. SLC mediates antitumor responses in immune competent mice: requirement for CD4 and CD8 lymphocyte subsets. 3LL (H-2d) or L1C2 (H-2b) cells ($10^5$) were inoculated s.c. into the right supra scapular area in C57BL/6 and BALB/c mice. Five days after tumor establishment, 0.5 μg of murine recombinant SLC per injection or PBS diluent (1×) was administered three times per week intratumorally. Equivalent amounts of murine serum albumin was used as an irrelevant protein for control injections, and it did not alter the tumor volumes. Tumor volume was monitored three times per week (n=10-12 mice/group). Intratumoral SLC administration led to significant reduction in tumor volumes compared with untreated tumor-bearing mice (p<0.01). In the SLC treatment group, 40% of mice showed complete tumor eradication (A and D). SLC-mediated antitumor responses are lymphocyte dependent as evidenced by the fact that this therapy did not alter tumor growth in SCID mice (FIG. 1E). Studies performed in CD4 and CD8 knockout mice also showed a requirement for both CD4 and CD8 effector subsets for SLC-mediated tumor regression (FIG. 1, B and C).

The present disclosure provides methods for treating tumors, reducing tumor volume and reducing the progression of cancer in a subject comprising administering CCL21 (SLC) in combpination with checkpoint inhibitors to regulate the immune system involved in tumor progression.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in see Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Abbreviations used herein include: APC, antigen-presenting cell; SLC, secondary lymphoid organ chemokine; DC, dendritic cell; IP-10, IFN-γ inducible protein 10; TGF-β, transforming growth factor 13; GM-CSF, granulocyte macrophage colony-stimulating factor; IL, interleukin; FBS, fetal bovine serum; mAb, monoclonal antibody; VEGF, vascular endothelial growth factor; EIA, enzyme immunoassay; SV40 TAg, simian virus 40 large T antigen; Ag, antigen; PGE2, prostaglandin E2; PE, phycoerythrin; LN, lymph node.

A. Brief Characterization of Features of the Invention

The invention is based on the discoveries disclosed herein that Secondary Lymphoid-Tissue Chemokine (SLC) modulates cytokine profiles in an immune response to syngeneic tumor cells and can inhibit the growth of these cells. The disclosure provided herein demonstrates the antitumor efficiency of SLC in a clinically relevant mouse model where the mice spontaneously develop tumors. For example, injection of recombinant SLC (e.g. in the axillary lymph node region) leads to a marked reduction in this syngeneic tumor burden with extensive lymphocytic and DC infiltration of the tumors and enhanced survival. SLC injection led to significant increases in CD4 and CD8 lymphocytes as well as DC at the tumor sites, lymph nodes, and spleen.

As discussed below, the cellular infiltrates observed at the site of the syngeneic tumors were accompanied by the enhanced elaboration of Type 1 cytokines and the antiangiogenic chemokines IFN-γ inducible protein 10, and monokine induced by IFN-γ (MIG). In contrast, lymph node and tumor site production of the immunosuppressive cytokine transforming growth factor 13 was decreased in response to SLC treatment. In vitro, after stimulation with irradiated autologous tumor, splenocytes from SLC-treated mice secreted significantly more IFN-γ and granulocyte macrophage colony-stimulating factor, but reduced levels of interleukin 10. Significant reduction in tumor burden in a model in which tumors develop in an organ-specific manner provides a strong rationale for additional evaluation of SLC in regulation of tumor immunity and its use in lung cancer immunotherapy.

In view of the disclosure provided herein and because DCs are potent APCs that function as principle activators of T cells, the capacity of SLC to facilitate the colocalization of both DC and T cells is shown to reverse tumor-mediated immune suppression and orchestrate effective cell mediated immune responses in a syngeneic context. In addition to its immunotherapeutic potential, SLC has been found to have potent angiostatic effects (Soto et al., Annu. Rev. Immunol., 15: 675-705, 1997), thus adding additional support for its use in cancer therapy.

Using transplantable murine lung cancer models, we show that the antitumor efficacy of SLC is T cell-dependent. In these transplant models, the antitumor efficacy of SLC was determined using transplantable tumors propagated at s.c. sites. In the transplantable models, recombinant SLC administered intratumorally led to complete tumor eradication in 40% of the treated mice. The SLC-mediated antitumor response was dependent on both CD4 and CD8 lymphocyte subsets and was accompanied by DC infiltration of the tumor. In recent studies that directly support the antiangiogenic capacity of this chemokine, Arenberg et al. (Arenberg et al., Cancer Immunol. Immunother., 49:587-592, 2000) have reported that SLC inhibits human lung cancer growth and angiogenesis in a SCID mouse model.

The spontaneous tumor model discussed herein demonstrates the antitumor properties of SLC in a clinically relevant model of cancer in which adenocarcinomas develop in an organ-specific manner. Specifically, in this model, transgenic mice expressing SV40 large TAg transgene under the control of the murine Clara cell-specific promoter, CC-10, develop diffuse bilateral bronchoalveolar carcinoma and have an average lifespan of 4 months (Magdaleno et al., Cell Growth Differ., 8: 145-155, 1997). The antitumor activity of SLC is determined in the spontaneous model for lung cancer by injecting recombinant SLC into the axillary lymph node region of the transgenic mice. The rationale for injecting SLC in the lymph node region was to colocalize DC to T-cell areas in the lymph nodes where they can prime specific antitumor immune responses. In many clinical situations access to lymph node sites for injection may also be more readily achievable than intratumoral administration. These results show that this approach is effective in generating systemic antitumor responses. SLC injected in the axillary lymph node regions of the CC-10 TAg mice evidenced potent antitumor responses with reduced tumor burden and a survival benefit as compared with CC-10 TAg mice receiving diluent control injections. The reduced tumor burden in SLC-treated mice was accompanied by extensive lymphocytic as well as DC infiltrates of the tumor sites, lymph nodes, and spleens.

The cytokine production from tumor sites, lymph nodes, and spleens of the CC-10 TAg mice was also altered as a result of SLC therapy. The following cytokines were measured: VEGF, IL-10, PGE-2, TGF-β, IFN-γ, GMCSF, IL-12, MIG, and IP-10 (Table 1B). The production of these cytokines was evaluated for the following reasons: the tumor site has been documented to be an abundant source of PGE-2, VEGF, IL-10, and TGF-β, and the presence of these molecules at the tumor site has been shown to suppress immune responses (Huang et al., Cancer Res., 58: 1208-1216, 1998; Gabrilovich et al., Nat. Med., 2: 1096-1103, 1996; Bellone et al., Am. J. Pathol., 155: 537-547, 1999). VEGF, PGE-2, and TGF-β have also been documented previously to promote angiogenesis (Fajardo et al., Lab. Investig., 74: 600-608, 1996; Ferrara, N. Breast Cancer Res. Treat., 36: 127-137, 1995; Tsujii et al., Cell, 93: 705-716, 1998). Antibodies to VEGF, TGF-β, PGE-2, and IL-10 have the capacity to suppress tumor growth in in vivo model systems. VEGF has also been shown to interfere with DC maturation (Gabrilovich et al., Nat. Med., 2: 1096-1103, 1996). Both IL-10 and TGF-β are immune inhibitory cytokines that may potently suppress Ag presentation and antagonize CTL generation and macrophage activation (Sharma et al., J. Immunol., 163: 5020-5028, 1999; Bellone et al., Am. J. Pathol., 155: 537-547, 1999). Although at higher pharmacological concentrations IL-10 may cause tumor reduction, physiological concentrations of this cytokine suppress antitumor responses (Sharma et al., J. Immunol., 163: 5020-5028, 1999; Sun et al., Int. J. Cancer, 80: 624-629, 1999; Halak et al., Cancer Res., 59: 911-917, 1999; Stolina et al., J. Immunol., 164: 361-370, 2000). Before SLC treatment in the transgenic tumor bearing mice, the levels of the immunosuppressive proteins VEGF, PGE-2, and TGF-β were elevated when compared with the levels in normal control mice. There was no such increase with IL-10. Similarly there were not significant alterations in IL-4 and IL-5 after SLC therapy. SLC-treated CC-10 TAg mice showed significant reductions in VEGF and TGF-β. The decrease in immunosuppressive cytokines was not limited to the lung but was evident systemically. SLC treatment of CC-10 TAg transgenic mice led to a decrease in TGF-β in lymph node-derived cells and reduced levels of PGE-2 and VEGF from splenocytes. Thus, benefits of a SLC-mediated decrease in these cytokines include promotion of antigen presentation and CTL generation (Sharma et al., J. Immunol., 163: 5020-5028, 1999; Bellone et al., Am. J. Pathol., 155: 537-547, 1999), as well as a limitation of angiogenesis (Fajardo et al., Lab. Investig., 74: 600-608, 1996; Ferrara, N. Breast Cancer Res. Treat., 36: 127-137, 1995; Tsujii et al., Cell, 93: 705-716, 1998).

It is well documented that successful immunotherapy shifts tumor specific T-cell responses from a type 2 to a type 1 cytokine profile (Hu et al., J. Immunol., 161: 3033-3041, 1998). Responses depend on IL-12 and IFN-γ to mediate a range of biological effects, which facilitate anticancer immunity. IL-12, a cytokine produced by macrophages (Trinchieri et al., 70: 83-243, 1998) and DC (Johnson et al., J. Exp. Med., 186:1799-1802, 1997), plays a key role in the induction of cellular immune responses (Ma et al., Chem. Immunol., 68: 1, 1997). IL-12 has been found to mediate potent antitumor effects that are the result of several actions involving the induction of CTL, Type 1-mediated immune responses, and natural killer activation (Trinchieri et al., 70: 83-243, 1998), as well as the impairment of tumor vascularization (Voest et al., J. Natl. Cancer Inst., 87: 581-586, 1995). IP-10 and MIG are CXC chemokines that chemoattract activated T cells expressing the CXCR3 chemokine receptor (Loetscher et al., J. Exp. Med., 184:963-969, 1996). Both IP-10 and MIG are known to have potent antitumor and antiangiogenic properties (Luster et al., J. Exp. Med., 178: 1057-1065, 1993; Brunda et al., J. Exp. Med., 178: 1223-1230, 1993; Arenberg et al., J. Exp. Med./84: 981-992, 1996; Sgadari et al., Blood, 89: 2635-2643, 1997). The lungs of SLC treated CC-10 TAg mice revealed significant increases in IFN-γ, IL-12, IP-10, MIG, and GM-CSF. MIG and IP-10 are potent angiostatic factors that are induced by IFN-γ (Arenberg et al., J. Exp. Med., 184: 981-992, 1996; Strieter et al., Biochem. Biophys. Res. Commun., 210: 51-57, 1995; Tannenbaum et al., J. Immunol., 161: 927-932, 1998) and may be responsible in part for the tumor reduction in CC-10 TAg mice after SLC administration. Because SLC is documented to have direct antiangiogenic effects (Soto et al., Annu. Rev. Immunol., 15: 675-705, 1997; Arenberg et al., Am. J. Resp. Crit. Care Med., 159:A746, 1999), the tumor reductions observed in this model maybe attributable to T cell-dependent immunity as well as participation by T cells secreting IFN-γ in inhibiting angiogenesis (Tannenbaum et al., J. Immunol., 161: 927-932, 1998). Hence, an increase in IFN-γ at the tumor site of SLC-treated mice would explain the relative increases in IP-10 and MIG. Both MIG and IP-10 are chemotactic for stimulated CXCR3-expressing T lymphocytes that could additionally amplify IFN-γ at the tumor site (Farber et al., J. Leukoc. Biol., 61: 246-257, 1997). Flow cytometric determinations revealed that both CD4 and CD8 cells were responsible for the increased secretion of GM-CSF and IFN-γ in SLC-treated mice. An increase in GM-CSF in SLC-treated mice could enhance DC maturation and antigen presentation (Banchereau et al., Nature (Lond.), 392: 245-252, 1998). Additional studies are necessary to precisely define the host cytokines that are critical to the SLC-mediated antitumor response.

The increase in the Type 1 cytokines was not limited to the lung but was evident systemically. SLC treatment of CC-10 TAg transgenic mice led to systemic increases in Type I cytokines and antiangiogenic chemokines. Hence, splenocytes from SLC-treated CC-10 TAg mice had an increase in GM-CSF, IL-12, MIG, and IP-10 as compared with diluent-treated CC-10 TAg mice. Similarly, lymph node-derived cells from SLC-treated mice secreted significantly enhanced levels of IFN-γ, IP-10, MIG, and IL-12. Recent studies suggest that the evaluation of type 1 responses at the LN sites may provide insights into antitumor responses in patients receiving immune therapy (Chu et al., Eur. J. Nuc. Med., 26: s50-53, 1999). The increase in GM-CSF and IFN-γ in the spleen and lymph nodes of SLC-treated mice could in part be explained by an increase in the frequency of CD4 and CD8 cells secreting these cytokines. The increase in Type 1 cytokines was in part attributable to an increase in specificity against the autologous tumor; when cocultured with irradiated CC-10 TAg tumor cells, splenocytes from SLC-treated CC-10 TAg mice secreted significantly increased amounts of GM-CSF and IFN-γ but reduced levels of IL-10. Cell surface staining of CC-10 cells followed by flow cytometry did not show detectable levels of MHC class II molecules. Although the tumor did not show MHC class II expression, CD4+ type 1 cytokine production may have occurred because splenic APC were present in the assay. Although in vitro tumor-stimulated splenic T cells from SLC-treated mice showed reduced expression of IL-10, SLC therapy did not lead to a decrease of IL-10 levels in vivo. The in situ microenvironment may provide other important factors from cellular constituents in addition to T cells that determines the overall levels of IL-10.

Taken together, the disclosure provided herein demonstrates how the administration of SLC, for example SLC injected in the axillary lymph node region in a clinically relevant spontaneous lung cancer model leads to the generation of systemic antitumor responses. Without being bound by a specific theory, the antitumor properties of SLC may be attributable to its chemotactic capacity in colocalization of DCs and T cells, as well as the induction of key cytokines such as IFN-γ, IP-10, MIG, and IL-12. Using the models disclosed herein, additional studies can delineate the importance of each of these cytokines in SLC-mediated antitumor responses. The potent antitumor properties demonstrated in this model of spontaneous bronchoalveolar carcinoma provide a strong rationale for additional evaluation of SLC regulation of tumor immunity and its use in immunotherapy for cancers such as cancers of the lung.

As described in detail below, the invention described herein has a number of embodiments. Typical embodiments include methods of modulating syngeneic physiological processes in mammals, for example effecting an increase in the expression of soluble cytokines such as Interferon-γ (IFN-γ) polypeptides and a decrease in the expression of soluble cytokines such as Transforming Growth Factor-β (TGF-β) polypeptides in a population of syngeneic mammalian cells including CD8 positive T cells, CD4 positive T cells, Antigen Presenting Cells and tumor cells by exposing the population of cells to an amount of secondary lymphoid tissue chemokine (SLC) polypeptide sufficient to inhibit the growth of the tumor cells. A closely related embodiment is a method of treating cancer or hyperproliferative cell growth in a mammal by administering a therapeutically effective amount of an SLC to the mammal.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but are not limited to, carcinoma, lymphoma, blastoma, sarcoma, and leukemia. More particular examples of such cancers include adenocarcinoma, breast cancer, ovarian cancer, colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer.

One of the focal issues in designing active cancer immunotherapy is that cancer cells are derived from normal host cells. Thus, the antigenic profile of cancer cells closely mimics that of normal cells. In addition, tumor antigens are not truly foreign and tumor antigens fit more with a self/altered self paradigm, compared to a non-self paradigm for antigens recognized in infectious diseases and organ transplants (see, e.g. Lewis et al., Semin Cancer Biol 6(6): 321-327 (1995)). In this context, an important aspect of the present invention is the characterization of the effects of SLC in an animal model where the cancer cells are spontaneous and the immune cells which respond to the cancer cells are therefore syngeneic. In this context, syngeneic is known in the art to refer to an extremely close genetic similarity or identity especially with respect to antigens or immunological reactions. Syngeneic systems include for example, models in which organs and cells (e.g. cancer cells and their non-cancerous counterparts) come from the same individual, and/or models in which the organs and cells come from different individual animals that are of the same inbred strain. Syngeneic models are particularly useful for studying oncogenesis and chemotherapeutic molecules. A specific example of a syngeneic model is the CC-10 TAg transgenic mouse model of spontaneous bronchoalveolar carcinoma described herein. In this context, artisans in the field of immunology are aware that, during mammalian development the immune system is tolerized to self antigens (e.g. those encoded by genes in the animal's germline DNA). As T-Ag is present in the germline of the transgenic animal, the transgenic animal's immune system is tolerized to this protein during maturation of the immune system.

In contrast to syngeneic, the term allogeneic is used to connote a genetic dissimilarity between tissues or cells that is sufficient to effect some type of immunological mechanism or response to the different antigens present on the respective tissues or cells. A specific example of an allogeneic model is one in which cancer cells from one strain of mice are transplanted into a different strain of mice. Allogeneic models are particularly useful for studying transplantation immunity and for the evaluation of molecules that can suppress the immune response to non-self antigens present on the transplanted tissues.

In order to provide clinically relevant paradigms for studying various pathologies which involve the immune system, animal models designed to assess immune responses must be predicated on an understanding of the immune system responds to foreign (non-self) tissues. In this context, those skilled in the field of transplantation immunity understand that an animal's immune response to allogeneic tissues is very different from an animal's immune response to syngeneic tissues (that is if a response will even occur). This is illustrated, for example, by the need for immunosuppressive agents in allogeneic organ transplants (immunosuppressive agents are needed to inhibit a response to non-self antigens present on the transplanted tissues). Therefore clinically relevant models cannot mix different immunophenotypes without considering and characterizing the profound implications that this has on immune response. Because the tumor cells are syngeneic in the CC-10 TAg transgenic mouse model of spontaneous bronchoalveolar carcinoma described herein, this model specifically avoids the problems associated with a confounding immune responses that result from the mixing different immunophenotypes.

As is known in the art, cytokines are crucial mediators of immune response. In this context, different cytokines, different concentrations of cytokines and/or different combinations of cytokines are used to generate a specific immune response in a specific context. In this regard, it is known in the art that different immune responses involve different cytokine profiles. Therefore, the inherent differences an immune response to non-self tissues as compared to an immune response to self tissues result in part from inherent differences in the cytokine profiles involved in each response.

Clinically relevant paradigms for the general examination of an immune response must also take a number of other factors into account. For example it is known in the art that certain murine strains demonstrate a high variability in their immune response to identical agents. See, for example, Dreau et al., Physiolo Behav 2000 70(5): 513-520 which teaches that the murine strains C57BL6, BALB/c and BDF (1) demonstrate high variability in their immune response to 2-deoxy-D-glucose induced stress. In addition, it is known that genetic polymorphisms among common mouse strains can significantly influence early cytokine production in stimulated naïve CD4 T cells (see, e.g. Lo et al., Int Rev Immunol 1995, 13(2):147-160). Therefore, clinically relevant models of immune responsiveness should not mix tissues and cells from murine strains which are known to demonstrate high variability in their immune response without considering and characterizing the profound implications that this has on an immune response generated by model which mixes tissues and cells from different murine strains. Because there is no mixing of tissues and cells from different murine strains in the CC-10 TAg transgenic mouse model of spontaneous bronchoalveolar carcinoma described herein, this model specifically avoids the problems associated with a confounding immune responses that result from the mixing different immunophenotypes.

Clinically relevant paradigms for the specific evaluation of an immune response to cancer cells must also take a number of factors into account. For example many tumor cell lines have been selected to have certain characteristics such as enhanced invasive and metastatic behavior (see, e.g. Poste et al., Cancer Res. 42(7): 2770-2778 (1982)). As is known in the art, the selection for such characteristics can alter the factors such as the immunogenicity of such cell lines which, in turn, can confound models of immune responses that utilize such lines (see, e.g. De Baetselier et al., Nature 1980 13; 288(5787): 179-181). As is also known in the art, the growth of cell lines in tissue culture selects for an outgrowth of clones having characteristics associated with the greatest fitness in the culture medium, characteristics which are not necessarily consistent with tumor cell growth in vivo. Because the CC-10 TAg transgenic mouse model described herein produces spontaneous cancer cells (as compared to cell lines), this model specifically avoids the problems associated with the use of cell lines which have been subjected to specific (and non-specific) selective pressures during their period in tissue culture.

In addition to the above-mentioned problems with tumor cells, there are related problems associated with the use of cell lines in such models that relate to the ability of many cultured tumor lines to produce cytokines such as those that facilitate tumor growth. Specifically, it is known in the art that certain tumor cell lines express cytokines that are not produced by their non-cancerous counterparts or which are produced in quantities in normal tissues (see, e.g. Stackpole et al., In Vitro Cell Dev Biol Anim 1995, 31(3):244-251 and which discusses the autocrine growth of B16 melanoma clones and Shimizu et al., Cancer Res 1996, 56(14):3366-3370 which discusses the autocrine growth of colon carcinoma colon 26 clones). In contexts where one is evaluating an immune response or measuring a cytokine profile in an immune response, the use of cell lines in cancer model can be confounded by the presence of cytokines produced by the cell line (which can change the cytokine profile in these cells' environment). Therefore, in methods which seek to evaluate and/or modulate a cytokine profile, for example in clinically relevant models of immune responsiveness, artisans should not utilize cytokine generating cell lines into mice without considering and characterizing the profound implications that the presence of cell line produced cytokines has on an immune response generated by model.

As noted above, skilled artisans understand that the immune system responds to non-self tissues (e.g. allogeneic transplants) differently than it does to self tissues (e.g. a syngeneic transplant). As the ability to distinguish between self and non-self is a fundamental aspect of immunity, those skilled in the art understand that an immune reaction observed in response to a foreign tissue is not predictive of an immune response to a self tissue (that is if an immune response will even occur). This is illustrated, for example, by the need for individuals who have received allogeneic organ transplants to take immunosuppressive drugs. Consequently, any clinically relevant model of immune response must take this fundamental aspect of immunity into account, particularly ones designed to assess an immune response to cancer, a pathology which is characterized by the aberrant growth of self tissues. As the transgenic mouse model that is used herein does not expose the animal's immune system to non-self antigens, does not mix cells and tissue from strains of mice that have been observed to have different immunological characteristics and is instead directed to evaluating an immune response to spontaneous tumors, the data provided by this model is clinically relevant in the context of human cancers.

A "neutralizing antibody" is an antibody molecule which is able to eliminate or significantly reduce a biological function of a target antigen to which it binds. Accordingly, a "neutralizing" anti-target antibody is capable of eliminating or significantly reducing a biological function, such as enzyme activity, ligand binding, or intracellular signaling.

An antibody that "specifically binds" is "target specific", is "specific for" target or is "immunoreactive" with the target antigen refers to an antibody or antibody substance that binds the target antigen with greater affinity than with similar antigens. In one aspect of the disclosure, the target-binding polypeptides, or fragments, variants, or derivatives thereof, will bind with a greater affinity to human target as compared to its binding affinity to target of other, i.e., non-human, species, but binding polypeptides that recognize and bind orthologs of the target are within the scope provided.

For example, an antibody or fragment thereof "specific for" its cognate antigen indicates that the variable regions of the antibodies recognize and bind the polypeptide of interest with a detectable preference (i.e., able to distinguish the polypeptide of interest from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody for use in the methods of the present disclosure are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6.

The term "therapeutically effective amount" is used herein to indicate the amount of target-specific composition of the disclosure that is effective to ameliorate or lessen symptoms or signs of disease to be treated.

The terms "treat", "treated", "treating" and "treatment", as used with respect to methods herein refer to eliminating, reducing, suppressing or ameliorating, either temporarily or permanently, either partially or completely, a clinical symptom, manifestation or progression of an event, disease or condition. Such treating need not be absolute to be useful.

B. Typical Methodologies for Practicing Embodiments of the Invention

A number of the methods disclosed herein are related to general methods known in the art that can be used to study the effects of SLC in the context of immunological responses to non-self (i.e. allogeneic) tissues such as genetically non-identical cancer cells transplanted into host animals.

The methods disclosed herein may be employed in protocols for treating pathological conditions in mammals such as cancer or immune-related diseases. In typical methods, SLC polypeptide is administered to a mammal, alone or in combination with still other therapeutic agents or techniques. Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like. For example, a wide variety of diagnostic factors that are known in the art to be associated with cancer may be utilized such as the expression of genes associated with malignancy (including PSA, PSCA, PSM and human glandular kallikrein expression) as well as gross cytological observations (see e.g. Bocking et al., Anal Quant Cytol. 6(2):74-88 (1984); Eptsein, Hum Pathol. 1995 February; 26(2):223-9 (1995); Thorson et al., Mod Pathol. 1998 June; 11(6):543-51; Baisden et al., Am J Surg Pathol. 23(8):918-24 91999)).

The methods of the invention are useful in the treatment of hyperproliferative disorders and cancers, and are particularly useful in the treatment of solid tumors. Types of solid tumors that may be treated according to the methods of the invention include, but are not limited to lung cancer, melanoma, breast cancer, tumors of the head and neck, ovarian cancer, endometrial cancer, urinary tract cancers, stomach cancer, testicular cancer, prostate cancer, bladder cancer, pancreatic cancer, leukemia, lymphoma, bone cancer, liver cancer, colon cancer, rectal cancer, metastases of the above, and metastases of unknown primary origin. For example, in preferred embodiments of the invention, SLC is administered to modulate cytokine profiles and/or inhibit the growth of spontaneous tumor cells of the adenocarcinoma lineage (as is demonstrated herein in the transgenic mouse model). As is known in the art, tumor cells of the adenocarcinoma lineage can occur spontaneously in a number of different organ systems (see, e.g., Yagi et al., Gan No Rinsho 1984 30(11):1392-1397).

Polypeptides useful in the methods of the invention encompass both naturally occurring proteins as well as variations and modified forms thereof. As noted above, "SLC polypeptide or protein" is meant a Secondary Lymphoid-Tissue Chemokine. SLC includes naturally occurring mammalian SLCs, and variants and fragments thereof, as defined below. Preferably the SLC is of human or mouse origin (see, e.g. SEQ ID NOS: 1 and 2 in Table 4 respectively). Most preferably the SLC is human SLC. Human SLC has been cloned and sequenced (see, e.g. Nagira et al. (1997) J Biol Chem 272:19518; the contents of which are incorporated by reference). Consequently the cDNA and amino acid sequences of human SLC are known in the art (see, e.g. Accession Nos. BAA21817 and AB002409). Mouse SLC has also been cloned and sequenced (see, e.g. Accession Nos. NP_035465 and NM_011335). Hromas el al. (1997) J. Immunol 1.59:2554; Hedrick et al. (1997) J. Immunol 159:1589; and Tanabe el al. (1997) J. Immunol 1.59:5671; the contents of which are incorporated herein by reference.

SLC polypeptides for use in the methods disclosed herein can be SLC variants, SLC fragments, analogues, and derivatives. By "analogues" is intended analogues of either SLC or an SLC fragment that comprise a native SLC sequence and structure, having one or more amino acid substitutions, insertions, or deletions. Peptides having one; or more peptoids (peptide mimics) are also encompassed by the term analogues (WO 91/04282). By "derivatives" is intended any suitable modification of SLC, SLC fragments, or their respective analogues, such as glycosylation, phosphorylation, or other addition of foreign moieties (e.g. Pegylation as described below), so long as the desired activity is retained. Methods for masking SLC fragments, analogues, and derivatives are available in the art.

In an illustrative SLC derivative, a polyol, for example, can be conjugated to an SLC molecule at one or more amino acid residues, including lysine residues, as disclosed in WO 93/00109. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to an SLC protein or variant is termed "pegylation." However, those skilled in the art recognize that other polyols, such as, for example, poly(propylene glycol) and polyethylene-polypropylene glycol copolymers, can be employed using the techniques for conjugation described herein for PEG. The degree of pegylation of an SLC variant of the present invention can be adjusted to provide a desirably increased in vivo half-life (hereinafter "half-life"), compared to the corresponding non-pegylated protein.

A variety of methods for pegylating proteins have been described. See, e.g., U.S. Pat. No. 4,179,337 (issued to Davis et al.), disclosing the conjugation of a number of hormones and enzymes to PEG and polypropylene glycol to produce physiologically active non-immunogenic compositions. Generally, a PEG having at least one terminal hydroxy group is reacted with a coupling agent to form an activated PEG having a terminal reactive group. This reactive group can then react with the α- and ε-amines of proteins to form a covalent bond. Conveniently, the other end of the PEG molecule can be "blocked" with a non-reactive chemical group, such as a methoxy group, to reduce the formation of PEG-crosslinked complexes of protein molecules.

As used herein, the SLC gene and SLC protein includes the murine and human SLC genes and proteins specifically described herein, as well as biologically active structurally and/or functionally similar variants or analog of the foregoing. SLC peptide analogs generally share at least about 50%, 60%, 70%, 80%, 90% or more amino acid homology (using BLAST criteria). For example, % identity values may be generated by WU-BLAST-2 (Altschul et al., 1996, Methods in Enzymology 266:460-480). SLC nucleotide analogs preferably share 50%, 60%, 70%, 80%, 90% or more nucleic acid homology (using BLAST criteria). In some embodiments, however, lower homology is preferred so as to select preferred residues in view of species-specific codon preferences and/or optimal peptide epitopes tailored to a particular target population, as is appreciated by those skilled in the art. Fusion proteins that combine parts of different SLC proteins or fragments thereof, as well as fusion proteins of a SLC protein and a heterologous polypeptide are also included. Such SLC proteins are collectively referred to as the SLC-related proteins, the proteins of the invention, or SLC.

The term "variant" refers to a molecule that exhibits a variation from a described type or norm, such as a protein that has one or more different amino acid residues in the corresponding position(s) of a specifically described protein. An analog is an example of a variant protein. As used herein, the SLC-related gene and SLC-related protein includes the SLC genes and proteins specifically described herein, as well as structurally and/or functionally similar variants or analog of the foregoing. SLC peptide analogs generally share at least about 50%, 60%, 70%, 80%, 90% or more amino acid homology (using BLAST criteria). SLC nucleotide analogs preferably share 50%, 60%, 70%, 80%, 90% or more nucleic acid homology (using BLAST criteria). In some embodiments, however, lower homology is preferred so as to select preferred residues in view of species-specific codon preferences and/or optimal peptide epitopes tailored to a particular target population, as is appreciated by those skilled in the art.

Embodiments of the invention disclosed herein include a wide variety of art-accepted variants or analogs of SLC proteins such as polypeptides having amino acid insertions, deletions and substitutions. SLC variants can be made using methods known in the art such as site-directed mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the SLC variant DNA. Resulting mutants can be tested for biological activity. Sites critical for binding can be; determined by structural analysis such as crystallization, photoaffinity labeling, or nuclear magnetic resonance. See, deVos et al. (1992) Science 255:306 and Smith et al. (1992) J. Mol. Biol. 224:899.

As is known in the art, conservative amino acid substitutions can frequently be made in a protein without altering the functional activity of the protein. Proteins of the invention can comprise conservative substitutions. Such changes typically include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins,* (W.H. Freeman & Co., N.Y.); Chothia, J. Mol. Biol., 150:1 (1976)). If alanine substitution does not yield adequate amounts of variant, an isosteric amino acid can be used.

Variant SLC proteins and SLC polypeptide fragments useful in the methods of the present invention must possess SLC biological activity. Specifically, they must possess the desired biological activity of the native protein, that is, the dendritic cell chemoattractant activity, angiostatic activity or anti-tumor activity as described herein. For the purposes of the invention, a "SLC variant" will exhibit at least 30% of a dendritic cell-chemoattractant activity, tumor inhibitory activity or angiostatic activity of the SLC. More typically, variants exhibit more than 60% of at least one of these activities; even more typically, variants exhibit more than 80% of at least one of these activities. As disclosed herein, the biological activity of a SLC protein may also be assessed by examining the ability of the SLC to modulate cytokine expression in vivo such as effecting an increase in the expression of Interferon-γ (IFN-γ) polypeptides and a decrease in the expression of Transforming Growth Factor-β (TGF-β) polypeptides in a population of syngeneic mammalian cells including CD8 positive T cells, CD4 positive T cells, Antigen Presenting Cells and tumor cells. Alternatively the biological activity of a SLC protein may also be assessed by exposing the population of cells to an amount of secondary lymphoid tissue chemokine (SLC) polypeptide and examining the ability that this molecule has to inhibit the growth of syngeneic tumor cells.

The SLC may be administered directly by introducing a SLC polypeptide, SLC variant or SLC fragment into or onto the subject. Alternatively, the SLC may be produced in situ following the administration of a polynucleotide encoding a SLC polypeptide, SLC variant or SLC fragment may be introduced into the subject.

The SLC agents of the invention comprise native SLC polypeptides, native SLC nucleic acid sequences, polypeptide and nucleic acid variants, antibodies, monoclonal antibodies, and other components that are capable of blocking the immune response through manipulation of SLC expression, activity and receptor binding. Such components include, for example, proteins or small molecules that interfere with or enhance SLC promoter activity; proteins or small molecules that attract transcription regulators; polynucleotides, proteins or small molecules that stabilize or degrade SLC mRNA; proteins or small molecules that interfere with receptor binding; and the like.

It is recognized that the invention is not bound by any particular method. Having recognized that SLC is chemotactic to mature dendritic cells, and T cells, any means of suppressing or enhancing SLC activity, for example, by interfering with receptor binding, interfering with SLC promoter activity, interfering with gene expression, mRNA stability, or protein stability, etc. can be used to modulate the primary immune response and are encompassed by the invention. The amino acid and DNA sequence of SLC are known in the art. See, for example, Pachynski et al. (1998) J. Immunol. 161:952; Yoshida el al. (1998) J. Biol. Chem. 273:7118, Nagira el al. (1998) Eur. J. Immunol. 28:1516-1523; Nagira el al. (1997) J Biol. Chem. 2:19518. All of which are herein incorporated by reference.

Polynucleotides for use in the methods disclosed herein may be naturally occurring, such as allelic variants, homologs, orthologs, or may be constructed by recombinant DNA methods or by chemical synthesis. Alternatively, the variant polypeptides may be non-naturally occurring and made by techniques known in the art, including mutagenesis. Polynucleotide variants may contain nucleotide substitutions, deletions, inversions and insertions.

As shown in Example 8, SLC encoding nucleic acid molecules can be inserted into vectors and used as gene therapy vectors. In addition to the illustrative adenoviral vectors disclosed herein, a wide range of other host-vector systems suitable for the expression of SLC proteins or fragments thereof are available, see for example, Sambrook et al., 1989, Current Protocols in Molecular Biology, 1995, supra. Gene therapy vectors can be delivered to a subject by, for example, intravenous injection, local administration (U.S. Pat. No. 5,328,470), implantation or by stereotactic injection (see e.g., Chen et al., PNAS 91:3054-3057 (1994)). Vectors for expression in mammalian hosts are disclosed in Wu et al. (1991) J. Biol. Chem. 266:14338; Wu and Wu (1988) J. Biol. Chem. 263:14621; and Zenke et al. (1990) Proc. Nat'l. Acad Sci. USA 87:3655. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

Preferred for use in the present invention are adenovirus vectors, and particularly tetracycline-controlled adenovirus vectors. These vectors may be employed to deliver and express a wide variety of genes, including, but not limited to cytokine genes such as those of the interferon gene family and the interleukin gene family.

A preferred method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct in host cells with complementary packaging functions and (b) to ultimately express a heterologous gene of interest that has been cloned therein.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences (Grunhaus and Horwitz, 1992). In contrast to retrovirus, the adenoviral infection of host cells does not result in chromosomal integration because wild-type adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In a current system, recombinant adenovirus is generated from homologous recombination between a shuttle vector and a master plasmid which contains the backbone of the adenovirus genome. Due to the possible recombination between the backbone of the adenovirus genome, and the cellular DNA of the helper cells which contain the missing portion of the viral genome, wild-type adenovirus may be generated from this process. Therefore, it is critical to isolate a single clone of virus from an individual plaque and examine its genomic structure.

Generation and propagation of most adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome (Jones and Shenk, 1978), the current adenovirus vectors, with the help of 293 cells, carry foreign DNA in either the E1, the E3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of most adenovirus vectors is at least 7.5 kb, or about 15% of the total length of the vector. More than 80% of the adenovirus viral genome remains in the vector backbone.

Gene transfer in vivo using recombinant E1-deficient adenoviruses results in early and late viral gene expression that may elicit a host immune response, thereby limiting the duration of transgene expression and the use of adenoviruses for gene therapy. In order to circumvent these potential problems, the prokaryotic Cre-loxP recombination system has been adapted to generate recombinant adenoviruses with extended deletions in the viral genome in order to minimize expression of immunogenic and/or cytotoxic viral proteins.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stifling at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for I to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

In some cases, adenovirus mediated gene delivery to multiple cell types has been found to be much less efficient compared to epithelial derived cells. A new adenovirus, AdPK, has been constructed to overcome this inefficiency (Wickham et al., 1996), AdPK contains a heparin-binding domain that targets the virus to heparin-containing cellular receptors, which are broadly expressed in many cell types. Therefore, AdPK delivers genes to multiple cell types at higher efficiencies than unmodified adenovirus, thus improving gene transfer efficiency and expanding the tissues amenable to efficient adenovirus mediated gene therapy.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the foreign gene expression cassette at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect (Brough et al., 1996).

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No severe side effects have been reported in studies of vaccination with wild-type adenovirus (Couch et al., 1963; Top et al., 1971), demonstrating their safety and therapeutic potential as in viva gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1991; Rich et al., 1993). Studies in administering recombinant adenovirus to different tissues include trachea instillation (Rosenfeld et al., 1991; 1992), muscle injection (Ragot et al., 1993), peripheral intravenous injections (Herz and Gerard, 1993) and stereotactic inoculation into the brain (Le Gal La Salle et al., 1993). Recombinant adenovirus and adeno-associated virus (see below) can both infect and transduce non-dividing human primary cells.

Adeno-associated virus (AAV) is also an attractive system for use in construction of vectors for delivery of and expression of genes as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Yoder et al., 1994; Zhou et al., 1994a; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991), rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzvczka, 1992).

Typically, recombinant AAV (rAAV) virus is made by cotransfecting a plasmid containing the gene of interest flanked by the two AAV terminal repeats (McLaughlin et al., 1988: Samulski et al., 1989; each incorporated herein by reference) and an expression plasmid containing the wild type AAV coding sequences without the terminal repeats, for example pIM4S (McCarty et al., 1991; incorporated herein by reference). The cells are also infected or transfected with adenovirus or plasmids carrying the adenovirus genes required for AAV helper function, rAAV virus stocks made in such fashion are contaminated with adenovirus which must be inactivated by heat shock or physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

In particular aspects of the present invention, delivery of selected genes to target cells through the use of retrovirus infection will be desired. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988: Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

In some cases, the restricted host-cell range and low titer of retroviral vectors can limit their use for stable gene transfer in eukaryotic cells. To overcome these potential difficulties, a murine leukemia virus-derived vector has been developed in which the retroviral envelope glycoprotein has been completely replaced by the G glycoprotein of vesicular stomatitis virus (Burns et al., 1993). These vectors can be concentrated to extremely high titers (109 colony forming units/ml), and can infect cells that are ordinarily resistant to infection with vectors containing the retroviral envelope protein. These vectors may facilitate gene therapy model studies and other gene transfer studies that require direct delivery of vectors in vivo.

Other viral vectors may be employed for construction of expression vectors in the present invention. Vectors derived from viruses such as vaccinia virus (Ridgeway, 1988; Baichwal and Sugden, 1986; Coupar et al., 1988), sindbis virus and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

The methods of the present invention may be combined with any other methods generally employed in the treatment of the particular disease or disorder that the patient exhibits. For example, in connection with the treatment of solid tumors, the methods of the present invention may be used in combination with classical approaches, such as surgery, radiotherapy and the like. So long as a particular therapeutic approach is not known to be detrimental in itself, or counteracts the effectiveness of the SLC therapy, its combination with the present invention is contemplated. When one or more agents are used in combination with SLC therapy, there is no requirement for the combined results to be additive of the effects observed when each treatment is conducted separately, although this is evidently desirable, and there is no particular requirement for the combined treatment to exhibit synergistic effects, although this is certainly possible and advantageous.

In terms of surgery, any surgical intervention may be practiced in combination with the present invention. In connection with radiotherapy, any mechanism for inducing DNA damage locally within tumor cells is contemplated, such as y-irradiation, X-rays, UV-irradiation, microwaves and even electronic emissions and the like. The directed delivery of radioisotopes to tumor cells is also contemplated, and this may be used in connection with a targeting antibody or other targeting means. Cytokine therapy also has proven to be an effective partner for combined therapeutic regimens. Various cytokines may be employed in such combined approaches. Examples of cytokines include IL-1a, IL-113, IL-2, IL-3, IL-4, IL-5, IL-6, IL-7, IL-8, IL-9, IL-10, IL-11, IL-12, IL-13, TGF-β, GM-CSF, M-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Below is an exemplary, but in no way limiting, table of cytokine genes contemplated for use in certain embodiments of the present invention.

TABLE A

| Cytokine | Reference |
| --- | --- |
| human IL-1α | March et al., Nature, 315:641, 1985 |
| murine IL-1α | Lomedico et al., Nature, 312:458, 1984 |
| human IL-1β | March et al., Nature, 315:641, 1985; Auron et al., Proc. Natl. Acad. Sci. USA, 81:7907, 1984 |
| Murine IL-1β | Gray, J. Immunol., 137L3644m 1986l Tekfirdm Nucl. Acids Res., 14:9955, 1986 |
| human IL-1ra | Eisenberg et al., Nature, 343:341, 1990 |
| human IL-2 | Taniguchi et al., Nature, 302:305, 1983; Maeda et al., Biochem. Biophys, Res. Commun., 115:1040, 1983 |
| human IL-2 | Taniguchi et al., Nature, 302:305, 1983 |
| human IL-3 | Yang et al., Cell, 47:3, 1986 |

TABLE A-continued

| Cytokine | Reference |
|---|---|
| murine IL-3 | Yokota et al., Proc. Natl. Acad. Sci. USA, 81:1070, 1984; Fung et al., Nature, 307:233, 1984; Miyatake et al., Proc. Natl. Acad. Sci. USA, 82:316, 1985 |
| human IL-4 | Yokota et al., Proc. Natl. Acad. Sci. USA, 83:5894, 1986 |
| murine IL-4 | Norma et al., Nature, 319:640, 1986; Lee et al., Proc. Natl. Acad. Sci. USA, 83:2061,1986 |
| human IL-5 | Azuma et al., Nucl. Acids Res., 14:9149, 1986 |
| murine IL-5 | Kinashi et al., Nature, 324:70, 1986; Mizuta et al., Growth Factors, 1:51, 1988 |
| human IL-6 | Hirona et al., Nature, 324:73, 1986 |
| murine IL-6 | Van Snick et al., Eur. J. Immunol., 18:193, 1988 |
| human IL-7 | Goodwin et al., Proc. Natl. Acad. Sci. USA, 86:302, 1989 |
| murine IL-7 | Namen et al., Nature, 333:571, 1988 |
| human IL-8 | Schmid et al., J. Immunol., 139:250, 1987; Matsushima et al., J. Exp. Med., 167:1883, 1988; Lindley et al., Proc. Natl Acad. Sci. USA, 85:9199, 1988 |
| human IL-9 | Renauld et al., J. Immunol., 144:4235, 1990 |
| murine IL-9 | Renauld et al., J. Immunol., 144:4235, 1990 |
| human Angiogenin | Kurachi et al., Biochemistry, 24:5494, 1985 |
| human GROα | Richmond et al., EMBO J., 7:2025, 1988 |
| murine MIP-1α | Davatelis et al., J. Exp. Med., 167:1939, 1988 |
| murine MIP-1β | Sherry et al., J. Exp. Med., 167:2251, 1988 |
| human MIF | Weiser et al., Proc. Natl. Acad. Sci. USA, 86:7522, 1989 |
| human G-CSF | Nagata et al., Nature, 319:415, 1986; Souza et al., Science, 232:61, 1986 |
| human GM-CSF | Cantrell et al., Proc. Natl. Acad. Sci. USA, 82:6250, 1985; Lee et al., Proc. Natl. Acad. Sci. USA, 82:4360, 1985; Wong et al., Science, 228:810, 1985 |
| murine GM-CSF | Gough et al., EMBO J., 4:645, 1985 |
| human M-CSF | Wong, Science, 235:1504, 1987; Kawasaki, Science, 230:291, 1985; Ladner, EMBO J., 6:2693, 1987 |
| human EGF | Smith et al., Nucl. Acids Res., 10:4467, 1982; Bell et al., Nucl. Acids Res., 14:8427, 1986 |
| human TGF-α | Derynck et al., Cell, 38:287, 1984 |
| human FGF acidic | Jaye et al., Science, 233:541, 1986; Gimenez-Gallego et al., Biochem. Biophys. Res. Commun., 138:611, 1986; Harper et al. Biochem., 25: 4097, 1986 |
| human β-ECGF | Jaye et al., Science, 233:541, 1986 |
| human FGF basic | Abraham et al., EMBO J., 5:2523, 1986; Sommer et al., Biochem. Biophys. Res. Comm., 144:543, 1987 |
| murine IFN-β | Higashi et al., J. Biol. Chem., 258:9522, 1983; Kuga, Nucl. Acids Res., 17:3291, 1989 |
| human IFN-γ | Gray et al., Nature, 295:503, 1982; Devos et al., Nucl. Acids Res., 10:2487, 1982; Rinderknecht, J. Biol. Chem. 259:6790, 1984 |
| human IGF-I | Jansen et al., Nature, 306:609, 1983; Rotwein et al., J. Biol. Chem., 261:4828, 1986 |
| human IGF-II | Bell et al., Nature, 310:775, 1984 |
| human β-NGF chain | Ullrich et al., Nature, 303:821, 1983 |
| human PDGF A chain | Betsholtz et al., Nature, 320:695, 1986 |
| human PDGF B chain | Johnsson et al., EMBO J., 3:921, 1984; Collins et al., Nature, 316:748, 1985 |
| human TGF-β1 | Derynck et al., Nature, 316:701, 1985 |
| human TNF-α | Pennica et al., Nature, 312:724, 1984; Fransen et al., Nucl. Acids Res., 13:4417, 1985 |
| human TNF-β | Gray et al., Nature, 312:721, 1984 |
| murine TNF-β | Gray et al., Nucl. Acids Res., 15:3937, 1987 |

Compositions of the present invention can have an effective amount of an engineered virus or cell for therapeutic administration in combination with an effective amount of a checkpoint inhibitor as described herein and/or a compound (second agent) that is a chemotherapeutic agent as exemplified below. Such compositions will generally be dissolved or dispersed in a pharmaceutically acceptable carrier or aqueous medium. A wide variety of chemotherapeutic agents may be used in combination with the therapeutic genes of the present invention. These can be, for example, agents that directly cross-link DNA, agents that intercalate into DNA, and agents that lead to chromosomal and mitotic aberrations by affecting nucleic acid synthesis.

A variety of chemotherapeutic agents are intended to be of use in the combined treatment methods disclosed herein. Chemotherapeutic agents contemplated as exemplary include, e.g., etoposide (VP-16), ADRIAMYCIN, 5 fluorouracil (5FU), camptothecin, actinomycin-D, mitomycin C, cisplatin (CDDP) and even hydrogen peroxide.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/in$^2$ for 5 days every three weeks for a total of three courses. Cisplatin is not absorbed orally and must therefore be delivered via injection intravenously, subcutaneously, intratumorally or intraperitoneally.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Further useful agents include compounds that interfere with DNA replication, mitosis and chromosomal segregation. Such chemotherapeutic compounds include ADRIAMYCIN, also known as doxorubicin, etoposide, verapamil, podophyllotoxin, and the like. Widely used in a clinical setting for the treatment of neoplasms, these compounds are administered through bolus injections intravenously at doses ranging from 25-75 mg/in2 at 21 day intervals for ADRIAMYCIN, to 35-50 mg/in2 for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Plant alkaloids such as TAXOL are also contemplated for use in certain aspects of the present invention. TAXOL is an experimental antimitotic agent, isolated from the bark of the ash tree, *Taxus brevifolia*. It binds to tubulin (at a site distinct from that used by the *vinca* alkaloids) and promotes the assembly of microtubules. TAXOL is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Exemplary chemotherapeutic agents that are useful in connection with combined therapy are listed in Table B. Each of the agents listed therein are exemplary and by no means limiting. The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE B

Table 4
Chemotherapeutic Agents Useful In Neoplastic Disease

| Class | Type Of Agent | Nonproprietary Names (Other Names) | Disease |
| --- | --- | --- | --- |
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (Streptozotocin) | Malignant pancreatic insulinoma, malignant carcinoid |

TABLE B-continued

Table 4
Chemotherapeutic Agents Useful In Neoplastic Disease

| Class | Type Of Agent | Nonproprietary Names (Other Names) | Disease |
|---|---|---|---|
| | Triazines | Dacarbazine (DTIC; dimethyltrizenoimidazole-carboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorodeoxyuridine; FUdR) | |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide (VP16) Tertiposide | Testis, small-cell lung and other lung, breast, Hodgkin's disease, non-Hodgkin's lymphomas, acute granulocytic leukemia, Kaposi's sarcoma |
| | Antibiotics Antibiotics, continued | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, |

TABLE B-continued

Table 4
Chemotherapeutic Agents Useful In Neoplastic Disease

| Class | Type Of Agent | Nonproprietary Names (Other Names) | Disease |
|---|---|---|---|
| | | Bleomycin | genitourinary, thyroid, lung, stomach, neuroblastoma Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o.p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

Checkpoint Proteins

Cytotoxic T-lymphocyte antigen 4 (CTLA-4)(CD152) is a well-known costimulatroy molecule involved in the B7-1/B7-2 constimulatory pathway of T cell activation. CTLA-4 is expressed on the surface of helper T cells and transmits an inhibitory signal to T cells (See e.g., Krummel et al., J. Exp. Med. 182 (2): 459-65, 1995). Antibodies that bind CTLA-4 include ipilimumab and tremilimumab.

Programmed cell death protein 1 (PD-1), also known as cluster of differentiation 279 (CD279), is a cell surface co-inhibitory receptor expressed on activated T cells, B cells and macrophages, and is a component of immune checkpoint blockade (Shinohara et al., Genomics., 23(3):704, (1994); Francisco et al., Immunol Rev., 236: 219, (2010)). PD-1 limits the activity of T cells upon interaction with its two ligands PD-L1 (also known as B7-H1; CD274) and PD-L2 (B7-DC; CD273) (Postow et al., J Clin Oncol., 33: 9, (2015)). Interaction of PD-1 with PD-L1 and PD-L2, reduces T-cell proliferation, cytokine production, and cytotoxic activity (Freeman G J et al., J Exp Med., 192:1027-34, (2000); Brown J A et al., J Immunol., 170:1257-66, (2003)).

Two monoclonal antibodies have been approved by the U.S. Food and Drug Administration (FDA) for the inhibition of PD-1 immunotherapy. Pembrolizumab (KEYTRUDA®, Merck Sharp & Dohme Corp.) is approved for use in metastatic melanoma, and nivolumab (Opdivo®, Bristol-Myers Squibb) is approved for use in metastatic melanoma and metastatic squamous non-small cell lung cancer (NSCLC). Both of these antibodies bind to the PD-1 receptor and block its interaction with its ligands, PD-L1 and PD-L2.

Inhibitors of PD-L1 have also been shown to be effective at inhibiting solid tumors in bladder cancer, head and neck cancer, and gastrointestinal cancers (Herbst R S et al., J Clin Oncol., 31: 3000 (2013); Heery C R et al., J Clin Oncol., 32: 5s, 3064 (2014); Powles T et al., J Clin Oncol, 32: 5s, 5011 (2014); Segal N H et al., J Clin Oncol., 32: 5s, 3002 (2014)).

4-1BB (CD137) is a type 2 cell surface receptor in the TNF superfamily and is expressed on activated T Lymphocytes and on dendritic cells. 4-1BB acts as a costimulatory molecule that causes T cell proliferation.

Lymphocyte-activation gene 3 (LAG-3, CD223) is a cell surface molecule checkpoint inhibitor expressed on activated T cells, natural killer cells, B cells and plasmacytoid dendritic cells. LAG-3 negatively regulates cellular proliferation, activation, and homeostasis of T cells, in a similar fashion to CTLA-4 and PD-1 (Workman et al., Journal of Immunology 172:5450-5, 2004). LAG-3 monoclonal antibody BMS-986016 has been the subject of clinical trial testing.

TIM-3 is a receptor expressed on IFN-γ-producing CD4+T helper 1 (Th1) and CD8+T cytotoxic 1 (Tc1) T cells (Anderson A., Cancer Immunol Res 2; 393, 2014).

In exemplary embodiments, the SLC polypeptides, SLC variants, SLC fragments, SLC analogues, SLC derivatives, SLC polynucleotides encoding said polypeptides, variants, or fragments, and/or the SLC agents described herein, are used in combination with an immune checkpoint inhibitor. Cellular immunity begins when T cells recognize specific peptide fragments of intracellular proteins expressed on the subject of APCs which are bound to specific mixed histocompatibility complex (MHC) molecules. This interaction requires the presence of B7, a costimulatory molecule, which binds to CD28. A result of this activation is the upregulation of cytotoxic T-lymphocyte antigen 4 (CTLA-4). CTLA-4 binding to its receptor on T lymphocytes leads to negative regulation of T cell activation. Another co-inhibitory pathway uses the programmed cell death 1 receptor (PD-1), which is another inhibitory receptor present on activated T cells. When PD-1 binds to its ligand (PD-L1), the ability of the activated T cell to produce an effective immune response is down-modulated.

Accordingly, the invention provides methods comprising (a) administering to the subject (i) a SLC polypeptide, (ii) a polynucleotide encoding the SLC polypeptide, (iii) a cell comprising the polynucleotide, or (iv) a combination thereof, and (b) administering to the subject an immune checkpoint inhibitor. In exemplary aspects, the methods are methods of treating a cancer or a solid tumor in a subject.

Immune checkpoint inhibitors are known in the art (see, for example, Brahmer and Pardoll, Cancer Immunol Res 1; 85 (2013), and references cited therein), and any one or a combination of immune checkpoint inhibitors are useful for combined therapy with the SLC polypeptides, SLC variants, SLC fragments, SLC analogues, SLC derivatives, SLC polynucleotides encoding said polypeptides, variants, or fragments, and/or the SLC agents described herein.

In various embodiments, the immune checkpoint inhibitor is an antibody, optionally, a monoclonal antibody, specific for one or more of CTLA-4, a CTLA-4 receptor, PD-1, PD1-L1, PD1-L2, 4-1BB, OX40, LAG-3, TIM-3, or a combination thereof.

In exemplary aspects, the immune checkpoint inhibitor is an inhibitor of CTLA-4. In exemplary aspects, the immune checkpoint inhibitor is an inhibitor of CTLA-4 receptor. In exemplary aspects, the immune checkpoint inhibitor is an inhibitor of PD-1. In exemplary aspects, the immune checkpoint inhibitor is an inhibitor of any PD-1 ligand, including, PD1-L1 and PD1-L2. In exemplary aspects, the immune checkpoint inhibitor is a monoclonal antibody that specifically binds to CTLA-4 or the CTLA-4 receptor. In exemplary aspects, the monoclonal antibody that specifically binds to CTLA-4 is ipilimumab and tremilimumab. Methods of making monoclonal antibodies are known in the art. See, e.g., Antibodies: A Laboratory Manual, eds. Harlow and Lane, CSHL Press, Cold Spring Harbor, N.Y., 1988.

In exemplary aspects, the immune checkpoint inhibitor is a monoclonal antibody that specifically binds to PD-1, or any one of its ligands. In exemplary aspects, the immune checkpoint inhibitor is a monoclonal antibody that specifically binds to PD-L1. In exemplary aspects, the immune checkpoint inhibitor is a monoclonal antibody that specifically binds to PD1-L2.

In exemplary aspects, the monoclonal antibody that specifically binds to PD-1 is Nivolumab (BMS936558; Bristol Meyers Squibb), Pembrolizumab (MK-3475; Merck), Pidilizumab (CT-011; CureTech), Lambrolizumab, BMS-936559, Atezolizumab, or AMP-224 (GSK/Amplimmune), AMP224 (MedImmune); AUNP12 (Dr. Reddy's Laboratories Ltd.); BGB108 (BeiGene); MCLA134 (Merus BV); MEDI0680 (MedImmune); PDR001 (Novartis); REGN2810 (Regeneron/Sanofi); SHR1210 (Jiangsu Hengrui Medicine/Incyte); STIA110X (Sorrento); STIA1110 (Sorrento); TSR042 (AnaptysBio/Tesaro). In exemplary aspects, the monoclonal antibody that specifically binds to PD1-L1 is BMS-936559 (BMS/Ono), MPDL3280A (Roche/Genentech), or MEDI-4736 (MedImmune), MSB0010718C (Merck/Serono), ALN-PDL (Alnylam); BGBA317 (BeiGene); KD033 (Kadmon Corp.); KY1003 (Kymab Ltd.); STIA100X (Sorrento); STIA1010 (Sorrento); STIA1011 (Sorrento); STIA1012 (Sorrento); and STIA1014 (Sorrento).

In exemplary aspects, the immune checkpoint inhibitor is an inhibitor of 4-1BB (also known as CD137). In exemplary aspects, the immune checkpoint inhibitor of 4-1BB is a monoclonal antibody that specifically binds to 4-1BB, including, but not limited to BMS-663513 (Bristol-Myers Squibb) and PF-05082566 (PF-2566).

In exemplary aspects, the immune checkpoint inhibitor is an inhibitor of OX40. In exemplary aspects, the inhibitor of OX40 is a monoclonal antibody that specifically binds to OX40. An exemplary OX40 monoclonal antibody is described in Curti, et al., A phase I trial of monoclonal antibody to OX40 in patients with advanced cancer (abstract). International Society for Biological Therapy of Cancer Annual Meeting, 2007.

In exemplary embodiments, the checkpoint inhibitor is a LAG-3 inhibitor In exemplary aspects, the inhibitor of LAG-3 is a monoclonal antibody that specifically binds to LAG-3.

In exemplary embodiments, the checkpoint inhibitor is a TIM-3 inhibitor In exemplary aspects, the inhibitor of TIM-3 is a monoclonal antibody that specifically binds to TIM-3.

In various embodiments, the immune checkpoint inhibitor is a small molecule inhibitor that inhibits the activity of one or more of CTLA-4, a CTLA-4 receptor, PD-1, PD1-L1, PD1-L2, 4-1BB, OX40, LAG-3, TIM-3, or a combination thereof.

In exemplary aspects, the immune checkpoint inhibitor, e.g., the PD1 or PD-L1 inhibitor, is administered at a dose within about 1 to 20 mg/kg. In exemplary aspects, the immune checkpoint inhibitor, e.g., the PD1 or PD-L1 inhibitor, is administered at a dose within about 1 to 10 mg/kg. In exemplary aspects, the immune checkpoint inhibitor, e.g., the PD1 or PD-L1 inhibitor, is administered parenterally, such as intravenously. In exemplary aspects, the immune checkpoint inhibitor, e.g., the PD1 or PD-L1 inhibitor, is administered every 1-2 weeks. In exemplary aspects, the immune checkpoint inhibitor, e.g., the PD1 or PD-L1 inhibitor, is administered once every 2 weeks. Dosages and regimens are adjusted to avoid or minimize the treated subject experiencing any adverse events, including, for example, fatigue, rash, diarrhea, skin disorders, gastrointestinal events, endocrinopathies.

In exemplary aspects, an SLC polypeptide is administered in combination with an immune checkpoint inhibitor, and, optionally, the SLC polypeptide comprises an amino acid sequence of SEQ ID NO: 1 or SEQ ID NO: 2.

In exemplary aspects, an SLC polynucleotide encoding an SLC polypeptide is administered in combination with an immune checkpoint inhibitor. Optionally, the encoded SLC polypeptide comprises an amino acid sequence of SEQ ID NO: 1 or SEQ ID NO: 2. In exemplary aspects, the SLC polynucleotide is inserted into and is thus a part of a vector, e.g., a recombinant expression vector, which vector administered to the subject in combination with the immune checkpoint inhibitor. In exemplary aspects, the vector is an adenoviral vector. The adenoviral vector may be any one of those described herein. In exemplary aspects, the adenoviral vector is a replication-deficient adenoviral vector. In exemplary aspects, the subject comprises a solid tumor and the SLC polynucleotide is administered to the subject intratumorally. In alternative aspects, the SLC polynucleotide is administered to the subject parenterally, e.g., intravenously or subcutaneously.

In exemplary aspects, a cell comprising and expressing an SLC polynucleotide encoding an SLC polypeptide is administered in combination with an immune checkpoint inhibitor. In exemplary aspects, the cell is part of a population of cells and the population of cells comprises and expresses the SLC polynucleotide encoding the SLC polypeptide. In exemplary aspects, the population of cells is administered in combination with an immune checkpoint inhibitor. In exemplary aspects, the cell or population of cells comprises and expresses the SLC polynucleotide encoding an SLC polypeptide comprising an amino acid sequence of SEQ ID NO: 1 or SEQ ID NO: 2. In exemplary aspects, the cell or population of cells comprising and expressing the SLC polynucleotide is an APC or a population thereof. In exemplary aspects, the cell or population of cells comprising and expressing the SLC polynucleotide is a dendritic cell or a population thereof. In exemplary aspects, the APC, e.g., the dendritic cell, or population thereof, is autologous to the subject being treated. In such aspects, the method is an ex vivo method.

In exemplary aspects, at least or about $1 \times 10^5$ or at least or about $1 \times 10^6$ cells comprising and expressing the polynucleotide encoding the SLC polypeptide are administered to the subject. In exemplary aspects, at least or about $2 \times 10^6$ cells, at least or about $3 \times 10^6$ cells, at least or about $4 \times 10^6$ cells, at least or about $5 \times 10^6$ cells, at least or about $6 \times 10^6$ cells, at least or about $7 \times 10^6$ cells, at least or about $8 \times 10^6$ cells, at least or about $9 \times 10^6$ cells, at least or about $1 \times 10^7$ cells, at least or about $2 \times 10^7$ cells, or at least or about $3 \times 10^7$ cells comprising and expressing the polynucleotide encoding the SLC polypeptide are administered to the subject. In exemplary aspects, the cells produce a sufficient amount of SLC in a given time period. In exemplary aspects, the cells produce at least or about 0.10 ng of SLC per $1 \times 10^6$ cells in a 24-hour period. In exemplary aspects, the cells produce at least or about 0.15 ng of SLC per $1 \times 10^6$ cells in a 24-hour period. In exemplary aspects, the cells produce at least or about 0.20 ng of SLC per $1 \times 10^6$ cells in a 24-hour period. In exemplary aspects, the cells produce at least or about 0.25 ng of SLC per $1 \times 10^6$ cells in a 24-hour period. In exemplary aspects, the cells produce at least or about 0.30 ng of SLC per $1 \times 10^6$ cells in a 24-hour period. In exemplary aspects, the cells produce at least or about 0.35 ng of SLC per $1 \times 10^6$ cells in a 24-hour period. In exemplary aspects, the cells produce at least or about 0.40 ng of SLC per $1 \times 10^6$ cells in a 24-hour period. In exemplary aspects, the cells produce at least or about 0.45 ng of SLC per $1 \times 10^6$ cells in a 24-hour period. In exemplary aspects, the cells produce at least or about 0.50 ng of SLC per $1 \times 10^6$ cells in a 24-hour period. In exemplary aspects, 1 to 30 million cells produce about 0.2 to 0.45 ng (e.g., 0.292 ng to about 0.413 ng) of SLC per $1 \times 10^6$ cells in a 24-hour period.

In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered before administration of the immune checkpoint inhibitor. In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered about 1 day, about 2 days, about 3 days, about 4 days, about 5 days, about 6 days, about 1 week, about 2 weeks, about 3 weeks, or about 4 weeks before administration of the immune checkpoint inhibitor.

In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered after administration of the immune checkpoint inhibitor. In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered about 1 day, about 2 days, about 3 days, about 4 days, about 5 days, about 6 days, about 1 week, about 2 weeks, about 3 weeks, or about 4 weeks after administration of the immune checkpoint inhibitor.

In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered concurrently with the immune checkpoint inhibitor. In various embodiments, the agents are administered in a separate formulation and administered concurrently, with concurrently referring to agents given within 30 minutes of each other. The methods also provide that the SLC composition and checkpoint inhibitor are administered with a second agent, e.g., a chemotherapeutic, which can be administered prior to administration with either the SLC composition and/or the checkpoint inhibitor, after administration with either the SLC composition and/or the checkpoint inhibitor, or administered concurrent with either the SLC composition and/or checkpoint inhibitor.

In various embodiments, it is contemplated the SLC agent and checkpoint inhibitor may be given simultaneously, in the same formulation.

In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered before and after administration of the immune checkpoint inhibitor administration. In exemplary aspects, the SLC polypeptides, SLC variants, SLC fragments, SLC analogues, SLC derivatives, SLC polynucleotides encoding said polypeptides, variants, or fragments, and/or the SLC agents described herein is/are administered before administration of the immune checkpoint inhibitor, after administration of the immune checkpoint inhibitor, and concurrently with the immune checkpoint inhibitor.

In exemplary aspects, the (i) SLC polypeptide, (ii) polynucleotide encoding the SLC polypeptide, (iii) cell comprising the polynucleotide, or (iv) combination thereof, is administered to the subject more than once. In exemplary aspects, the (i) SLC polypeptide, (ii) polynucleotide encoding the SLC polypeptide, (iii) cell comprising the polynucleotide, or (iv) combination thereof, is administered to the subject twice weekly, once weekly, once every 2 weeks, once every 3 weeks, or once monthly. In exemplary aspects, the immune checkpoint inhibitor is administered to the subject more than once. In exemplary aspects, the immune checkpoint inhibitor is administered to the subject twice weekly, once weekly, once every 2 weeks, once every 3 weeks, or once monthly.

In exemplary aspects, the subject comprises a solid tumor and the cells are administered to the subject intratumorally. In alternative aspects, the cells are administered to the subject parenterally, e.g., intravenously or subcutaneously.

In exemplary aspects, the method comprises intravenously administering to the subject an immune checkpoint inhibitor about once every two weeks at a dosage within about 1 to about 20 mg/kg and intratumorally administering to the subject about 1 to about 30 million cells comprising and expressing an SLC polynucleotide encoding an SLC polypeptide comprising the amino acid sequence of SEQ ID NO: 1 or SEQ ID NO: 2. In exemplary aspects, the method comprises intravenously administering to the subject an immune checkpoint inhibitor about once every two weeks at a dosage within about 1 to about 20 mg/kg and intratumorally administering to the subject an SLC polynucleotide encoding an SLC polypeptide comprising the amino acid sequence of SEQ ID NO: 1 or SEQ ID NO: 2.

In exemplary aspects, the cells or SLC polypeptide are administered to the subject about 2 weeks prior to the first administration of the immune checkpoint inhibitor. In exemplary aspects, the cells or SLC polypeptide are administered to the subject monthly after the first administration of cells or SLC polypeptide. In exemplary aspects, the immune checkpoint inhibitor is administered to the subject every 2 weeks starting two weeks after the first administration of the immune checkpoint inhibitor.

In exemplary aspects, the methods are methods of treating a cancer or a solid tumor in a subject. The cancer may be any of those described herein or known in the art. In exemplary aspects, the cancer is one selected from the group consisting of acute lymphocytic cancer, acute myeloid leukemia, alveolar rhabdomyo sarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma.

The solid tumor in exemplary aspects is a solid tumor of the following: Tumor Type Data Status Acute Myeloid Leukemia (AML), Breast cancer (BRCA), Chromophobe renal cell carcinoma (KICH), Clear cell kidney carcinoma (KIRC), Colon and rectal adenocarcinoma (COAD, READ), Cutaneous melanoma (SKCM), Glioblastoma multiforme (GBM), Head and neck squamous cell carcinoma (HNSC), Lower Grade Glioma (LGG), Lung adenocarcinoma (LUAD), Lung squamous cell carcinoma (LUSC), Ovarian serous cystadenocarcinoma (OV), Papillary thyroid carcinoma (THCA), Stomach adenocarcinoma (STAD), Prostate adenocarcinoma (PRAD), Uterine corpus endometrial carcinoma (UCEC), Urothelial bladder cancer (BLCA), Papillary kidney carcinoma (KIRP), Liver hepatocellular carcinoma (LIHC), Cervical cancer (CESC), Uterine carcinosarcoma (UCS), Adrenocortical carcinoma (ACC), Esophageal cancer (ESCA), Pheochromocytoma & Paraganglioma (PCPG), Pancreatic ductal adenocarcinoma (PAAD), Diffuse large B-cell lymphoma (DLBC), Cholangiocarcinoma (CHOL), Mesothelioma (MESO), Sarcoma (SARC), Testicular germ cell cancer (TGCT), Uveal melanoma (UVM). In exemplary aspects, the solid tumor is a lung tumor. In exemplary aspects, the solid tumor is a non-small cell lung carcinoma (NSCLC) solid tumor.

The SLC polypeptides, SLC polypeptide variants, SLC polypeptide fragments, SLC polynucleotides encoding said polypeptides, variants and fragments, and the SLC agents useful in the methods of the invention can be incorporated into pharmaceutical compositions suitable for administration into a mammal. The term "mammal" as used herein refers to any mammal classified as a mammal, including humans, cows, horses, dogs and cats. In a preferred embodiment of the invention, the mammal is a human. Such compositions typically comprise at least one SLC polypeptide, SLC polypeptide variant, SLC polypeptide fragment, SLC polynucleotide encoding said polypeptide, variant or fragment, an SLC agent, or a combination thereof, and a pharmaceutically acceptable carrier. Methods for formulating the SLC compounds of the invention for pharmaceutical administration are known to those of skill in the art. See, for example, Remington: The Science and Practice of Pharmacy, 19$^{th}$ Edition, Gennaro (ed.) 1995, Mack Publishing Company, Easton, Pa.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the, invention is formulated to be compatible with its intended route of administration.

The route of administration will vary depending on the desired outcome. Generally for initiation of an immune response, injection of the agent at or near the desired site of inflammation or response is utilized. Alternatively other routes of administration may be warranted depending upon the disease condition. That is, for suppression of neoplastic or tumor growth, injection of the pharmaceutical composition at or near the tumor site is preferred. Alternatively, for prevention of graft rejection, systemic administration maybe used. Likewise, for the treatment or prevention of autoimmune diseases systemic administration may be preferred. Examples of routes of systemic administration include parenteral, e.g., intravenous, intradermal, subcutaneous, oral (e.g., inhalation) transdermal (topical), transmucosal, and rectal administration. Solutions or suspensions used for parenteral, intradermal, or subcutaneous application can include the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose.

In one embodiment, the pharmaceutical composition can be delivered via slow release formulation or matrix comprising SLC protein or DNA constructs suitable for expression of SLC protein into or around a site within the body. In this manner, a transient lymph node can be created at a desired implant location to attract dendritic cells and T cells initiating an immune response.

The pharmaceutical compositions can be included in a container, pack, or dispenser together with instructions for administration. That result can be reduction and/or alleviation of the signs, symptoms, or causes of a disease or any other desired alteration of a biological system. The pharmaceutical compositions of the invention, comprising SLC polypeptides, SLC polypeptide variants, SLC polypeptide fragments, polynucleotides encoding said SLC polypeptides, variants and fragments, as well as SLC agents, as defined above, are administered in therapeutically effective amounts. The "therapeutically effective amount" refers to a nontoxic dosage level sufficient to induce a desired biological result (e.g. the enhancement of an immune response). In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

Amounts for administration may vary based upon the desired activity, the diseased state of the mammal being treated, the dosage form, method of administration, patient factors such as age, sex, and severity of disease. It is recognized that a therapeutically effective amount is provided in a broad range of concentrations. Such range can be determined based on binding assays, chemotaxis assays, and in vivo assays.

Regimens of administration may vary. A single injection or multiple injections of the agent may be used. Likewise, expression vectors can be used at a target site for continuous expression of the agent. Such regimens will vary depending on the severity of the disease and the desired outcome. In a preferred embodiment, an SLC or SLC composition is injected directly into the tumor or into a peritumor site. By peritumor site is meant a site less than about 15 cm from an outer edge of the tumor. In a highly preferred embodiment, an SLC or SLC composition is injected into an lymph node that is proximal to the tumor. SLC administration may be to one or more sites. Preferably, SLC administration is at multiple sites within a tumor and/or surrounding a tumor.

The SLC polypeptide is preferably administered to the mammal in a carrier; preferably a pharmaceutically-acceptable carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing, for example, the SLC polypeptide, which matrices are in the form of shaped articles, e.g., films, liposomes or microparticles. It will be apparent to those persons skilled in the art that certain carriers may be more preferable depending upon, for instance, the route of administration and concentration of SLC polypeptide being administered.

The SLC polypeptide can be administered to the mammal by injection (e.g., intravenous, intraperitoneal, subcutaneous, intramuscular, intraportal), or by other methods such as infusion that ensure its delivery to the bloodstream in an effective form. The SLC polypeptide may also be administered by isolated perfusion techniques, such as isolated tissue perfusion, to exert local therapeutic effects. Local or intravenous injection is preferred.

Effective dosages and schedules for administering the SLC polypeptides may be determined empirically (e.g. using the models disclosed herein), and making such determinations is within the skill in the art. Those skilled in the art will understand that the dosage of SLC polypeptide that must be administered will vary depending on, for example, the mammal which will receive the SLC polypeptide, the route of administration, the particular type of molecule used (e.g. polypeptide, polynucleotide etc.) used and other drugs being administered to the mammal.

As noted above, the SLC polypeptide may be administered sequentially or concurrently with one or more other therapeutic agents. The amounts of this molecule and therapeutic agent depend, for example, on what type of drugs are used, the pathological condition being treated, and the scheduling and routes of administration but would generally be less than if each were used individually. It is contemplated that the antagonist or blocking SLC antibodies may also be used in therapy. For example, a SLC antibody could be administered to a mammal (such as described above) to block SLC receptor binding.

Following administration of a SLC polypeptide to the mammal, the mammal's physiological condition can be monitored in various ways well known to the skilled practitioner. The therapeutic effects of the SLC polypeptides of the invention can be examined in in vitro assays and using in vivo animal models. A variety of well known animal models can be used to further understand the role of the SLC in the development and pathogenesis of for instance, immune related disease or cancer, and to test the efficacy of the candidate therapeutic agents. The in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

In a further embodiment of the invention, there are provided articles of manufacture and kits containing materials useful for treating pathological conditions or detecting or purifying SLC. The article of manufacture comprises a container with a label. Suitable containers include, for example, bottles, vials, and test tubes. The containers may be formed from a variety of materials such as glass or plastic. The container holds a composition having an active agent which is effective for treating pathological conditions such as cancer. The active agent in the composition is preferably SLC. The label on the container indicates that the composition is used for treating pathological conditions or detecting or purifying SLC, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

In exemplary aspects, the kit comprises (i) a SLC polypeptide, (ii) a polynucleotide encoding the SLC polypeptide, (iii) a cell comprising the polynucleotide, or (iv) a combination thereof, and an immune checkpoint inhibitor. In exemplary aspects, the immune checkpoint inhibitor is an inhibitor of CTLA-4. In exemplary aspects, the immune checkpoint inhibitor is an inhibitor of CTLA-4 receptor. In exemplary aspects, the immune checkpoint inhibitor is an inhibitor of PD-1. In exemplary aspects, the immune checkpoint inhibitor is an inhibitor of any PD-1 ligand, including, PD1-L1 and PD1-L2.

In various embodiments, the immune checkpoint inhibitor is an antibody, optionally, a monoclonal antibody, specific for one or more of CTLA-4, a CTLA-4 receptor, PD-1, PD1-L1, PD1-L2, 4-1BB, OX40, LAG-3, TIM-3, or a combination thereof.

In various embodiments, the immune checkpoint inhibitor is a small molecule inhibitor that inhibits the activity of one or more of CTLA-4, a CTLA-4 receptor, PD-1, PD1-L1, PD1-L2, 4-1BB, OX40, LAG-3, TIM-3, or a combination thereof.

In exemplary aspects, the immune checkpoint inhibitor is a monoclonal antibody that specifically binds to CTLA-4 or the CTLA-4 receptor. In exemplary aspects, the monoclonal antibody that specifically binds to CTLA-4 is ipilimumab or tremilimumab.

In exemplary aspects, the immune checkpoint inhibitor is a monoclonal antibody that specifically binds to PD-1, or any one of its ligands. In exemplary aspects, the immune checkpoint inhibitor is a monoclonal antibody that specifically binds to PD-L1. In exemplary aspects, the immune checkpoint inhibitor is a monoclonal antibody that specifically binds to PD1-L2.

In exemplary aspects, the monoclonal antibody that specifically binds to PD-1 is Nivolumab (BMS936558; Bristol Meyers Squibb), Pembrolizumab (MK-3475; Merck), Pidilizumab (CT-011; CureTech), Lambrolizumab, BMS-936559, Atezolizumab, or AMP-224 (GSK/Amplimmune), AMP224 (MedImmune); AUNP12 (Dr. Reddy's Laboratories Ltd.); BGB108 (BeiGene); MCLA134 (Merus BV); MEDI0680 (MedImmune); PDR001 (Novartis); REGN2810 (Regeneron/Sanofi); SHR1210 (Jiangsu Hengrui Medicine/Incyte); STIA110X (Sorrento); STIA1110 (Sorrento); and TSR042 (AnaptysBio/Tesaro).

In exemplary aspects, the monoclonal antibody that specifically binds to PD1-L1 is BMS-936559 (BMS/Ono), MPDL3280A (Roche/Genentech), or MEDI-4736 (MedImmune), MSB0010718C (Merck/Serono), ALN-PDL (Alnylam); BGBA317 (BeiGene); KD033 (Kadmon Corp.); KY1003 (Kymab Ltd.); STIA100X (Sorrento); STIA1010 (Sorrento); STIA1011 (Sorrento); STIA1012 (Sorrento); STIA1014 (Sorrento).

In exemplary aspects, the immune checkpoint inhibitor is an inhibitor of 4-1BB (also known as CD137). In exemplary aspects, the immune checkpoint inhibitor of 4-1BB is a monoclonal antibody that specifically binds to 4-1BB, including, but not limited to BMS-663513.

In exemplary aspects, the immune checkpoint inhibitor is an inhibitor of OX40. In exemplary aspects, the inhibitor of OX40 is a monoclonal antibody that specifically binds to OX40. An exemplary OX40 monoclonal antibody is described in Curti, et al., A phase I trial of monoclonal antibody to OX40 in patients with advanced cancer (abstract). International Society for Biological Therapy of Cancer Annual Meeting, 2007.

In exemplary embodiments, the checkpoint inhibitor is a LAG-3 inhibitor. In exemplary aspects, the inhibitor of LAG-3 is a monoclonal antibody that specifically binds to LAG-3.

In exemplary embodiments, the checkpoint inhibitor is a TIM-3 inhibitor. In exemplary aspects, the inhibitor of TIM-3 is a monoclonal antibody that specifically binds to TIM-3.

In exemplary aspects, the immune checkpoint inhibitor, e.g., the PD1 or PD-L1 inhibitor, is provided in the kit at a dose within about 1 to 20 mg/kg. In exemplary aspects, the immune checkpoint inhibitor, e.g., the PD1 or PD-L1 inhibitor, is provided in the kit at a dose within about 1 to 10 mg/kg. In exemplary aspects, the immune checkpoint inhibitor, e.g., the PD1 or PD-L1 inhibitor, is provided in the kit in a form which is suitable for parenteral, e.g., intravenous, administration.

In exemplary aspects, the kit comprises an SLC polypeptide and an immune checkpoint inhibitor and, optionally, the SLC polypeptide comprises an amino acid sequence of SEQ ID NO: 1 or SEQ ID NO: 2.

In exemplary aspects, the kit comprises an SLC polynucleotide encoding an SLC polypeptide and an immune checkpoint inhibitor. Optionally, the encoded SLC polypeptide comprises an amino acid sequence of SEQ ID NO: 1 or SEQ ID NO: 2. In exemplary aspects, the SLC polynucleotide is inserted into and is thus a part of a vector, e.g., a recombinant expression vector, which vector is part of the kit of the invention. In exemplary aspects, the vector is an adenoviral vector. The adenoviral vector may be any one of those described herein. In exemplary aspects, the adenoviral vector is a replication-deficient adenoviral vector. In exemplary aspects, the SLC polynucleotide is provided in the kit in a form which is suitable for intratumor administration. In alternative aspects, the SLC polynucleotide is provided in the kit in a form which is suitable for parenteral, e.g., intravenous, administration.

In exemplary aspects, the kit comprises a cell comprising and expressing an SLC polynucleotide encoding an SLC polypeptide and an immune checkpoint inhibitor. In exemplary aspects, the cell is part of a population of cells and the population of cells comprises and expresses the SLC polynucleotide encoding the SLC polypeptide. In exemplary aspects, the population of cells is administered in combination with an immune checkpoint inhibitor. In exemplary aspects, the cell or population of cells comprises and expresses the SLC polynucleotide encoding an SLC polypeptide comprising an amino acid sequence of SEQ ID NO: 1 or SEQ ID NO: 2. In exemplary aspects, the cell or population of cells comprising and expressing the SLC polynucleotide is an APC or a population thereof. In exemplary aspects, the cell or population of cells comprising and expressing the SLC polynucleotide is a dendritic cell or a population thereof.

In exemplary aspects, at least or about $1 \times 10^5$ or at least or about $1 \times 10^6$ cells comprising and expressing the polynucleotide encoding the SLC polypeptide are provided in the kit. In exemplary aspects, at least or about $2 \times 10^6$ cells, at least or about $3 \times 10^6$ cells, at least or about $4 \times 10^6$ cells, at least or about $5 \times 10^6$ cells, at least or about $6 \times 10^6$ cells, at least or about $7 \times 10^6$ cells, at least or about $8 \times 10^6$ cells, at least or about $9 \times 10^6$ cells, at least or about $1 \times 10^7$ cells, at least or about $2 \times 10^7$ cells, or at least or about $3 \times 10^7$ cells comprising and expressing the polynucleotide encoding the SLC polypeptide are provided in the kit. In exemplary aspects, the cells produce a sufficient amount of SLC in a given time period.

In exemplary aspects, the cells produce at least or about 0.10 ng of SLC per $1 \times 10^6$ cells in a 24-hour period. In exemplary aspects, the cells produce at least or about 0.15 ng of SLC per $1 \times 10^6$ cells in a 24-hour period. In exemplary aspects, the cells produce at least or about 0.20 ng of SLC per $1 \times 10^6$ cells in a 24-hour period. In exemplary aspects, the cells produce at least or about 0.25 ng of SLC per $1 \times 10^6$ cells in a 24-hour period. In exemplary aspects, the cells produce at least or about 0.30 ng of SLC per $1 \times 10^6$ cells in a 24-hour period. In exemplary aspects, the cells produce at least or about 0.35 ng of SLC per $1 \times 10^6$ cells in a 24-hour period. In exemplary aspects, the cells produce at least or about 0.40 ng of SLC per $1 \times 10^6$ cells in a 24-hour period. In exemplary aspects, the cells produce at least or about 0.45 ng of SLC per $1 \times 10^6$ cells in a 24-hour period. In exemplary aspects, the cells produce at least or about 0.50 ng of SLC per $1 \times 10^6$ cells in a 24-hour period.

Illustrative Embodiments of the Invention

The invention disclosed herein has a number of embodiments. A preferred embodiment of the invention is a method of effecting or modulating cytokine expression (e.g. changing an existing cytokine profile) in a mammal or in a population of cells derived from a mammal by exposing the population of cells to an amount of secondary lymphoid tissue chemokine (SLC) polypeptide sufficient to inhibit the growth of syngeneic tumor cells such as the spontaneous carcinoma cells that arise in the transgenic mouse model described herein. As disclosed herein, because the syngeneic models disclosed herein demonstrate how the addition of SLC coordinately modulates cytokine expression and inhibits the growth of the tumor cells, observations of these phenomena (modulation of cytokine expression and inhibition of tumor growth) can be used in cell based assays designed to assess the effects of potential immunostimulatory or immunoinhibitory test compounds. For example the disclosure provided herein allows one to examine the effects that test compound has on the ability of SLC to modulate cytokine expression and to identify compounds which modulate cytokine profiles in an advantageous manner.

The methods described herein can be employed in a number of contexts. For example the method described above can be practiced serially as the effects of compounds that have the ability modulate the cytokine profiles is examined. In one such embodiment of the invention, the cytokine profile (and/or inhibition of tumor growth) in response to SLC in a given cancer model is first examined to determine the effects of SLC in that specific context. The results of such assays can then be compared to the effects that SLC has on a known cancer model such as the transgenic mouse model described herein in order to confirm the effects of SLC in that model. A variation of the method can then be repeated using a test compound in place of SLC and the cytokine profile with the response to the test compound in the model then being examined to identify molecules which can produce physiological effects that are similar or dissimilar to SLC (e.g. modulate cytokine profile and/or inhibition of tumor growth in a specific way). In a related embodiment SLC and a test compound can be added simultaneously to see if the test compound can modulate the effects of SLC in a manner that may have some clinical applicability, for example to modulate the cytokine profile in a manner that enhances the inhibition of tumor growth, allows inhibition of growth with fewer side effects etc. As these models measure and compare both cytokine profiles and/or inhibition of tumor growth and because these are shown herein to be linked, the models provide internal references which facilitates the identification new molecules of interest and the dissection their effects on cellular physiology.

These methods provide a particularly useful clinical model because they parallel methods of treatment. Specifically, treating a cancer with SLC entails a method of effecting or modulating cytokine expression (e.g. changing the existing cytokine profile) in a mammal or in a certain population of cells derived from a mammal by exposing the population of cells to an amount of secondary lymphoid tissue chemokine (SLC) polypeptide sufficient to inhibit the growth of syngeneic tumor cells. In such clinical contexts, the effects of SLC in a given system can be observed or monitored in a number of ways, for example, the effects of SLC can be observed by the evaluation of a change in a cytokine profile, an evaluation the inhibition of tumor growth or tumor killing (e.g. by observing a reduction in tumor size and/or a reduction in the severity of symptoms associated with the tumor and/or tumor growth), an increased survival rate (as observed with the transgenic mouse model disclosed herein) and the like.

A specific embodiment of this embodiment of the invention is a method of effecting an increase in the expression of Interferon-γ (IFN-γ) polypeptide and a decrease in the expression of Transforming Growth Factor-β (TGF-β) polypeptide in a population of syngeneic mammalian cells including CD8 positive T cells, CD4 positive T cells, Antigen Presenting Cells and tumor cells comprising exposing the population of cells to an amount of secondary lymphoid tissue chemokine (SLC) polypeptide sufficient to inhibit the growth of the tumor cells and then repeating this method and additionally exposing the population of cells to a test compound consisting of a small molecule or polypeptide agent. The data from these assays can then be compared to observe effect that the test compound has on the expression of IFN-γ polypeptide or the expression of TGF-β polypeptide.

Any molecule known in the art can be tested for its ability to mimic or modulate (increase or decrease) the activity of SLC as detected by a change in the level of certain cytokines. For identifying a molecule that mimics or modulates SLC activity, candidate molecules can be directly provided to a cell or test subject in vivo or in vitro in order to detect the change in cytokine expression. Moreover, any lead activator or inhibitor structure known in the art can be used in conjunction with the screening and treatment methods of the invention. Such structures may be used, for example, to assist in the development of activators and/or inhibitors of SLC.

This embodiment of the invention is well suited to screen chemical libraries for molecules which modulate, e.g., inhibit, antagonize, or agonize or mimic, the activity of SLC as measured by the change in cytokine levels. The chemical libraries can be peptide libraries, peptidomimetic libraries, chemically synthesized libraries, recombinant, e.g., phage display libraries, and in vitro translation-based libraries, other non-peptide synthetic organic libraries, etc.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1-20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, Nature 354:84-86, which describes mixtures of free hexapeptides in which the first and second residues in each peptide were individually and specifically defined; Lam et al., 1991, Nature 354:82-84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709-710, which describes split synthesis and T-bag synthesis methods; and Gallop et al., 1994, J. Medicinal Chemistry 37(9): 1233-1251. Simply by way of other examples, a combinatorial library may be prepared for use, according to the methods of Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; or Salmon et al., 1993, Proc. Natl. Acad. Sci. USA 90:11708-11712. PCT Publication No. WO 93/20242 and Brenner and Lerner, 1992, Proc. Natl. Acad. Sci. USA 89:5381-5383 describe "encoded combinatorial chemical libraries," that contain oligonucleotide identifiers for each chemical polymer library member.

In a preferred embodiment, the library screened is a biological expression library that is a random peptide phage display library, where the random peptides are constrained (e.g., by virtue of having disulfide bonding).

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708-4712) may be used.

Conformationally constrained libraries that can be used include but are not limited to those containing invariant cysteine residues which, in an oxidizing environment, cross-link by disulfide bonds to form cysteines, modified peptides (e.g., incorporating fluorine, metals, isotopic labels, are phosphorylated, etc.), peptides containing one or more non-naturally occurring amino acids, non-peptide structures, and peptides containing a significant fraction of (-carboxyglutamic acid.

Libraries of non-peptides, e.g., peptide derivatives (for example, that contain one or more non-naturally occurring amino acids) can also be used. One example of these are peptoid libraries (Simon et al., 1992, Proc. Natl. Acad. Sci. USA 89:9367-9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138-11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, "-amino isobutyric acid, 4-aminobutyric acid, Abu, 2-amino butyric acid; (-Abu, -Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, C"-methyl amino acids, N"-methyl amino acids, fluoro-amino acids and amino acid analogs in general. Furthermore, the amino acid can be D (dextrorotary) or L (levorotary).

In a specific embodiment, fragments and/or analogs of proteins of the invention, especially peptidomimetics, are screened for activity as competitive or non-competitive inhibitors of activity.

In another embodiment of the present invention, combinatorial chemistry can be used to identify modulators. Combinatorial chemistry is capable of creating libraries containing hundreds of thousands of compounds, many of which may be structurally similar. While high throughput screening programs are capable of screening these vast libraries for affinity for known targets, new approaches have been developed that achieve libraries of smaller dimension but which provide maximum chemical diversity. (See e.g., Matter, 1997, Journal of Medicinal Chemistry 40:1219-1229).

One method of combinatorial chemistry, affinity fingerprinting, has previously been used to test a discrete library of small molecules for binding affinities for a defined panel of proteins. The fingerprints obtained by the screen are used to predict the affinity of the individual library members for other proteins or receptors of interest The fingerprints are compared with fingerprints obtained from other compounds known to react with the protein of interest to predict whether the library compound might similarly react. For example, rather than testing every ligand in a large library for interaction with a complex or protein component, only those ligands having a fingerprint similar to other compounds known to have that activity could be tested. (See, e.g., Kauvar et al., 1995, Chemistry and Biology 2:107-118; Kauvar, 1995, Affinity fingerprinting, Pharmaceutical Manufacturing International. 8:25-28; and Kauvar, Toxic-Chemical Detection by Pattern Recognition in New Frontiers in Agrochemical Immunoassay, D. Kurtz. L. Stanker and J. H. Skerritt. Editors, 1995, AOAC: Washington, D.C., 305-312).

Kay et al., 1993, Gene 128:59-65 (Kay) discloses a method of constructing peptide libraries that encode peptides of totally random sequence that are longer than those of any prior conventional libraries. The libraries disclosed in Kay encode totally synthetic random peptides of greater than about 20 amino acids in length. Such libraries can be advantageously screened to identify complex modulators.

(See also U.S. Pat. No. 5,498,538 dated Mar. 12, 1996; and PCT Publication No. WO 94/18318 dated Aug. 18, 1994).

A comprehensive review of various types of peptide libraries can be found in Gallop et al., 1994, J. Med. Chem. 37:1233-1251.

The population of syngeneic mammalian cells used in these methods typically includes CD8 positive T cells (i.e. those T cells expressing the CD8 antigen), CD4 positive T cells (i.e. those T cells expressing the CD8 antigen), Antigen Presenting Cells (APCs) and tumor cells. The term antigen presenting cell refers to cells that constitutively express class II MHC molecules and present stimulatory antigens to $T_H$ cells. There are three major classes of cells that function as APCs. These classes are macrophages, dendritic cells and B lymphocytes. Dendritic cells are the most potent among antigen presenting cells and are believed to be indispensable to the initiation of primary immune responses (see, e.g., Lanzavecchia (1993) Science 260: 937 and Grabbe et al., (1995) Immunology Today 16:117). Tumor cells are typically identified through a wide variety of techniques, including but not limited to, palpation, blood analysis, x-ray, NMR and the like. Moreover, a wide variety of diagnostic factors that are known in the art to be associated with cancer may be utilized to identify a tumor cells such as the expression of genes associated with malignancy (e.g. PSA, PSCA, PSM and human glandular kallikrein expression) as well as gross cytological observations (see e.g. Bocking et al., Anal Quant Cytol. 6(2):74-88 (1984); Eptsein, Hum Pathol. 1995 February; 26(2):223-9 (1995); Thorson et al., Mod Pathol. 1998 June; 11(6):543-51; Baisden et al., Am J Surg Pathol. 23(8):918-24 (1999)).

Using the models and methods disclosed herein, one can readily assess how the administration of SLC modulates cytokine profiles in an immune reaction and/or inhibits the growth of various spontaneous tumors. In preferred embodiments of the invention, SLC is administered to modulate cytokine profiles and/or inhibit the growth of spontaneous tumor cells of the adenocarcinoma lineage as is demonstrated herein. As is known in the art, the major forms of lung cancer including adenocarcinoma, squamous cell carcinoma, small cell carcinoma and large cell carcinoma represent a continuum of differentiation within a common cell lineage and express a number of tumor associated antigens (see, e.g. Berger et al., J Clin Endocrinol Metab 1981 53(2): 422-429 and Niho et al., Gan To Kagaku Ryoho 2001: 28(13): 2089-93; Ohshio et al., Tumori 1995 81(1): 67-73 and Hamasaki et al., Anticancer Res 2001 21(2A): 979-984). Consequently, the shared lineage relationships and antigenic profile provide evidence that SLC will have a closely analogous effect on the growth of these cancers of the lung (i.e. adenocarcinoma related lung cancers).

Preferably this method of effecting or modulating cytokine expression entails increasing the expression of Interferon-γ (IFN-γ, see, e.g. accession nos. AAB59534 and P01580) polypeptides and/or decreasing in the expression of Transforming Growth Factor-β (TGF-β, see, e.g., accession nos. AAA50405 and AAK56116) polypeptides in a population of syngeneic mammalian cells. In preferred methods, the increase in the expression of Interferon-γ (IFN-γ) polypeptides is at least about two-fold and a decrease in the expression of Transforming Growth Factor-β (TGF-β) polypeptides is at least about two-fold as measured by an enzyme linked immunoadsorbent (ELISA) assay. The effects of SLC in a given system can be observed in a number of other ways in addition to the ELISA assays discussed herein. For example, the effects of SLC can be observed by evaluation the inhibition of tumor growth or tumor killing (e.g. by observing a reduction in tumor size), and an increased survival rate (as observed with the transgenic mouse model disclosed herein) etc.

As disclosed herein the addition of SLC to this population of cells effects an increase in Granulocyte-Macrophage colony stimulating factor (GM-CSF, See, e.g. accession nos. gi:2144692 and gi:69708) polypeptides, monokine induced by IFN-γ (MIG, see, e.g. accession nos. P18340 and Q07325) polypeptides, Interleukin-12 (IL-12, see, e.g. accession nos. NP_032377 AAD56385 and AAD56386) polypeptides or IFN-γ inducible protein 10 (see, e.g. accession nos. P02778 and AAA02968) polypeptides; as well as a decrease in Prostaglandin E(2) polypeptides or vascular endothelial growth factor (VEGF, see, e.g. accession nos. NP_003367 and NP_033531) polypeptides. Consequently, preferred methods include those that generate a change in the cytokine profiles of these molecules via the administration of SLC. This modulation of polypeptide expression can be determined by any one of the wide variety of methods that are used in the art for evaluating gene expression such as the ELISA assays disclosed herein. In preferred methods, the increase and/or decrease in the expression of the polypeptides is at least about two-fold as measured by an enzyme linked immunoadsorbent (ELISA) assay. Additional profiling techniques are known in the art (see, e.g., Peale et al., J. Pathol 2001; 195(1):7-19).

The inhibition of tumor growth can be measured by any one of a wide variety of methods known in the art. Preferably wherein the inhibition of the growth of the syngeneic tumor cells is measured by quantification of tumor surface area. In preferred methods the syngeneic tumor cells are spontaneous cancer cells. As disclosed herein, transgenic which express SV40 large TAg transgene under the control of the murine Clara cell-specific promoter develop diffuse bilateral bronchoalveolar carcinoma. This model is but one of many syngeneic animal models of cancer known in the art that can be utilized according to the methods described herein (see, also Hakem et al., Annu. Rev. Genet. 2001; 35:209-41; Mundy Semin. Oncol. 2001 28(4 Suppl 11): 2-8; Sills et al., Toxicol Lett 2001 120(1-3): 1887-198; Kitchin, Toxicol Appl Pharmacol 2001; 172(3):249-61; and D'Angelo et al., J. Neurooncol 2000; 50(1-2):89-98).

In the methods disclosed hereinabove, the syngeneic cells can be exposed to the SLC by a variety of methods, for example by administering SLC polypeptide to a mammal via intratumoral injection, or alternatively administering SLC polypeptide to a mammal via intra-lymph node injection. In yet another mode of administration, an expression vector having a polynucleotide encoding a SLC polypeptide is administered to the mammal and the SLC polypeptide is produced by a syngeneic mammalian cell that has been transduced with an expression vector encoding the SLC polypeptide.

Yet another embodiment of the invention is a method of inhibiting the growth of spontaneous mammalian cancer cells in a population of syngeneic CD8 positive T cells, CD4 positive T cells and Antigen Presenting Cells by exposing the population of cells to an amount of secondary lymphoid tissue chemokine (SLC) polypeptide sufficient to inhibit the growth of the cancer cells. A closely related embodiment of the invention is a method of treating a syngeneic cancer in a mammalian subject comprising administering a therapeutically effective amount of an SLC to the subject. In preferred methods the SLC is human SLC. In highly preferred methods the SLC has the polypeptide sequence shown in SEQ ID NO: 1. Preferably, the SLC polypeptide is administered to a mammal via intratumoral injection, or via intra-lymph node injection. In yet another mode of administration, an expression vector having a polynucleotide encoding a SLC polypeptide is administered to the mammal and the SLC polypeptide is produced by a syngeneic mammalian cell that has been transduced with an expression vector encoding the SLC polypeptide. In a highly preferred embodiment, the cells are exposed to a SLC polypeptide that is expressed by a mammalian cell that has been transduced with an expression vector encoding the SLC polypeptide. A related embodiment of the invention consists of syngeneic host cells that have been transduced with an expression vector encoding the SLC polypeptide. In highly preferred embodiments of this aspect of the invention, the syngeneic host cells have been transduced with an expression vector encoding the SLC polypeptide in vivo.

Yet another embodiment of the invention is a method of inhibiting the growth of cancer cells (most preferably spontaneous cancer cells) in a mammal comprising administering secondary lymphoid tissue chemokine (SLC) to the mammal; wherein the SLC is administered to the mammal by transducing the cells of the mammal with a polynucleotide encoding the SLC shown in SEQ ID NO: 1 such that the transduced cells express the SLC polypeptide in an amount sufficient to inhibit the growth of the cancer cells. Preferably the vector is administered to a mammal via intratumoral injection, or alternatively via intra-lymph node injection.

Yet another embodiment of the invention is a method of inhibiting the growth of cancer cells (most preferably spontaneous cancer cells) in a mammal comprising administering secondary lymphoid tissue chemokine (SLC) ex vivo to the mammalian cells. As illustrated in Example 10, in a preferred embodiment, the SLC is administered to the mammal by transducing the cells of the mammal with a polynucleotide encoding SLC (e.g. SLC as shown in SEQ ID NO: 1) such that the transduced cells express the SLC polypeptide in an amount sufficient to inhibit the growth of syngeneic cancer cells. In such embodiments the population of cells can be removed from the mammal by any one of the variety of methods known in the art. Typically the cells are removed from the mammal at a site proximal to the cancer cells (e.g. at the site of the tumor or from a lymph node proximal to the tumor) and then reintroduced into the mammal after administration of the SLC (typically a site proximal to the cancer cells such as at the site of the tumor or at a lymph node proximal to the tumor).

One such embodiment of the invention is an ex vivo an method of treating a syngeneic cancer in a mammalian subject comprising administering a therapeutically effective amount of an SLC to the subject; wherein the SLC is expressed by a mammalian cell that has been transduced with an expression vector encoding the SLC polypeptide shown in SEQ ID NO: 1 or NO: 3, wherein the expression vector is administered after being transduced into a DC cell derived from the mammalian subject.

A related embodiment of the invention is an ex vivo method of treating a syngeneic cancer in a mammalian subject comprising administering a therapeutically effective amount of an SLC to the subject, wherein the SLC so administered is expressed by an autologous cell transduced with a polynucleotide encoding the SLC polypeptide of SEQ ID NO: 1; and further wherein the autologous cell is administered to the mammalian subject.

Yet another embodiment of the invention is an ex vivo method of facilitating in vivo tumor antigen uptake and presentation by an antigen presenting cell in a mammalian subject comprising transducing a syngeneic cell with a vector encoding the SLC polypeptide of SEQ ID NO: 1 so that the SLC polypeptide is expressed by the syngeneic cell and placing the syngeneic cell proximal to a syngeneic tumor cell expressing the tumor antigen. Preferably the syngeneic cell is an autologous DC cell, although the use of analogous antigen presenting cells known in the art is also contemplated.

Another embodiment of the invention is an method of attracting a T lymphocyte or a mature host dendritic cell to a site of a syngeneic tumor (e.g. an adenocarcinoma) in a mammal comprising the steps of: obtaining a dendritic cell from the mammal; introducing an exogenous polynucleotide encoding secondary lymphoid tissue chemokine as shown in SEQ ID NO: 1 into the dendritic cell (e.g. via transduction with a vector comprising this sequence) so that the cell expresses the secondary lymphoid tissue chemokine; and then placing the dendritic cell generated in this manner at the site of the syngeneic tumor in the mammal (e.g. via intratumoral injection); wherein the secondary lymphoid tissue chemokine expressed by the dendritic cell then attracts the T lymphocyte or the mature host dendritic cell to the site of the syngeneic tumor in the mammal via chemotaxis. As shown in Example 10, this method can be successfully employed to elicit a significant chemotaxis of peripheral blood lymphocytes and dendritic cells to the site of a tumor in vivo. Correspondingly, sixty percent of mice treated with method showed the complete eradication of syngeneic tumors treated with this method while only 12% of mice treated with unmodified or control dendritic cells responded. This method has a number of uses. For example this method can be applied to therapeutic contexts (e.g. in the treatment of individuals suffering from a cancer). In addition, this method provides a model for dissecting the various physiological process associated with immunosurveillance, in particular the natural ability that mammals have to respond to cancers. In addition, this model can be used to study the coordinate use of various known chemotherapeutic agents, for example the effect that a specific chemotherapeutic agent has on the immune response associated with the chemotaxis of peripheral blood lymphocytes and dendritic cells to the site of a tumor in vivo.

In such methods, the autologous cell expressing an endogenous SLC can be administered to the mammalian subject by a variety of methods known in the art. Preferably the autologous cell expressing an endogenous SLC is administered to the subject by intratumoral injection. Alternatively the autologous cell expressing an endogenous SLC is administered to the subject by intra-lymph node injection. Such methods can be used in the treatment of a variety of cancers, most preferably adenocarcinomas.

In alternative embodiments of the invention, SLC is administered as an SLC polypeptide in an amount sufficient to modulate a physiological process in the target cell (e.g. to upregulate the expression of polypeptides associated with immunosurveillance), wherein the physiological process so modulated facilitates the target cell's inhibition of the growth of syngeneic cancer cells.

Other embodiments of the invention include methods for the preparation of a medication for the treatment of pathological conditions including cancer by preparing a SLC composition for administration to a mammal having the pathological condition. A related method is the use of an effective amount of a SLC in the preparation of a medicament for the treatment of cancer, wherein the cancer cells are syngeneic cancer cells. Such methods typically involve the steps of including an amount of SLC sufficient to modulate a cytokine profile as discussed above and/or inhibit the growth of syngeneic (preferably spontaneous) cancer cells in vivo and an appropriate amount of a physiologically acceptable carrier. As is known in the art, optionally other agents can be included in these preparations.

Throughout this application, various publications are referenced (within parentheses for example). The disclosures of these publications are hereby incorporated by reference herein in their entireties. For example, certain general methods that are related to methods used with the invention disclosed herein are described in International Patent Application Number WO 00/38706, the contents of which are incorporated herein by reference. In order to facilitate an understanding of various typical aspects of the invention, certain aspects of these incorporated materials are reproduced herein.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention. However, the invention is only limited by the scope of the appended claims.

Examples

Example 1: Methods and Materials for Examining Immunomodulatory Molecules Such as SLC in Syngeneic Transplantable Tumor Models 1. Cell Culture and Tumorigenesis Models Two weakly immunogenic lung cancers, line 1 alveolar carcinoma (L1C2, H-2d) and Lewis lung carcinoma (3LL, H-2b), were utilized for assessment of antitumor responses in vivo. The cells were routinely cultured as monolayers in 25-$cm^3$ tissue culture flasks containing RPMI 1640 (Irvine Scientific, Santa Ana, Calif.) supplemented with 10% FBS (Gemini Bioproducts, Calabasas, Calif.), penicillin (100 U/ml), streptomycin (0.1 mg/ml), 2 mM glutamine (JRH Biosciences, Lenexa, Kans.) and maintained at 37° C. in a humidified atmosphere containing 5% $CO_2$ in air. The cell lines were *Mycoplasma* free, and cells were utilized up to the tenth passage before thawing frozen stock cells from liquid $N_2$. For tumorigenesis experiments, 105 3LL or L1C2 tumor cells were inoculated by s.c. injection in the right suprascapular area of C57BL/6 or BALB/c mice, and tumor volume was monitored three times per week. Five-day-old established tumors were treated with intratumoral injection of 0.5 μg of murine recombinant SLC or PBS diluent (Pepro Tech, Rocky Hill, N.J.) administered three times per week for 2 weeks. The endotoxin level reported by the manufacturer was <0.1 ng/μg (1 EU/μg) of SLC. The amount of SLC (0.5 μg) used for injection was determined by the in vitro biological activity data provided by the manufacturer. Maximal chemotactic activity of SLC for total murine T cells was 100 ng/ml. For in vivo evaluation of SLC-mediated antitumor properties, we utilized 5-fold more than this amount for each intratumoral injection. Tumorigenesis experiments were also performed in which equivalent amounts of murine serum albumin were utilized (Sigma, St. Louis, Mo.) as an irrelevant protein for control injections. Experiments were also performed in which the SLC was administered at the time of tumor inoculation. To determine the importance of the immune system in mediating antitumor responses after SLC administration, tumorigenesis experiments were conducted in SCID beige CB17 mice. SLC was administered s.c. at the time of tumor inoculation and then three times per week. CD4 and CD8 knockout mice were utilized to determine the contribution of CD4 and CD8 cells in tumor eradication. Two bisecting diameters of each tumor were measured with calipers. The volume was calculated using the formula (0.4) (ab2), with a as the larger diameter and b as the smaller diameter.

2. Cytokine Determination from Tumor Nodules, Lymph Nodes, and Spleens

The cytokine profiles in tumors, lymph nodes, and spleens were determined in both SLC and diluent-treated mice as previously described (Sharma et al., J. Immunol. 163:5020). Non necrotic tumors were harvested, cut into small pieces, and passed through a sieve (Bellco Glass, Vineland, N.J.). Tumor-draining lymph nodes and spleens were harvested from SLC-treated tumor-bearing, control tumor-bearing, and normal control mice. Lymph nodes and spleens were teased apart, RBC depleted with double-distilled H2O, and brought to tonicity with 1×PBS. Tumor nodules were evaluated for the production of IL-10, IL-12, GM-CSF, IFN-γ, TGF-β, vascular endothelial growth factor (VEGF), monokine induced by IFN-γ (MIG), and IP-10 by ELISA and PGE2 by enzyme immunoassay (EIA) in the supernatants after an overnight culture. Tumor-derived cytokine and PGE2 concentrations were corrected for total protein by Bradford assay (Sigma, St. Louis, Mo.). For cytokine determinations after secondary stimulation with irradiated tumor cells (5×10 6 cells/ml), splenic or lymph node-derived lymphocytes were cocultured with irradiated 3LL (105 cells/ml) at a ratio of 50:1 in a total volume of 5 ml. After an overnight culture, supernatants were harvested and GM-CSF, IFN-γ, IL-12, and IL-10 determined by ELISA.

3. Cytokine ELISA

Cytokine protein concentrations from tumor nodules, lymph nodes and spleens were determined by ELISA as previously described (Huang et al., Cancer Res. 58:1208). Briefly, 96-well Costar (Cambridge, Mass.) plates were coated overnight with 4 µg/ml of the appropriate anti-mouse mAb to the cytokine being measured. The wells of the plate were blocked with 10% fetal bovine serum (Gemini Bioproducts) in PBS for 30 min. The plate was then incubated with the Ag for 1 h, and excess Ag was washed off with PBS-Tween. The plate was incubated with 2 µg/mlbiotinylated mAb to the appropriate cytokine (PharMingen, San Diego, Calif.) for 30 min, and excess Ab was washed off with PBS-Tween. The plates were incubated with avidin peroxidase, and after incubation in OPD substrate to the desired extinction, the subsequent change in color was read at 490 nm with a Microplate Reader (Molecular Dynamics, Sunnyvale, Calif.). The recombinant cytokines used as standards in the assay were obtained from PharMingen. IL-12 (Biosource) and VEGF (Oncogene Research Products, Cambridge, Mass.) were determined by kits according to the manufacturer's instructions. MIG and IP-10 were quantified by a modification of a double ligand method as previously described (Standiford et al., J. Clin. Invest. 86:1945). The MIG and IP-10 Abs and protein were from R&D (Minneapolis, Minn.). The sensitivities of the IL-10, GM-CSF, IFN-γ, TGF-β, MIG, and IP-10 ELISA were 15 pg/ml. For IL-12 and VEGF, the sensitivities were 5 pg/ml.

4. PGE2 EIA

PGE2 concentrations were determined using a kit from Cayman Chemical (Ann Arbor, Mich.) according to the manufacturer's instructions as previously described (Huang et al., Cancer Res. 58:1208). The EIA plates were read by a Molecular Dynamics Microplate Reader.

5. Cytolytic Experiments

Cytolytic activity was assessed as previously described (Sharma et al., J. Immunol. 163:5020). To quantify tumor cytolysis after a secondary stimulation with irradiated tumor cells, lymph node-derived lymphocytes ($5×10^6$ cells/ml) from SLC-treated and diluent tumor-bearing mice were cultured with irradiated 3LL ($10^5$ cells/ml) tumors at a ratio of 50:1 in a total volume of 5 ml. After a 5-day culture, the lytic capacity of lymph node-derived lymphocytes were determined against chromium-labeled ($^{51}$Cr, Amersham Arlington, Heights, Ill.; sp. act. 250-500 mCi/mg) 3LL targets at varying E:T ratios for 4 h in 96-well plates. Spontaneous release and maximum release with 5% Triton X also were assessed. After the 4-h incubation, supernatants were removed and activity was determined with a gamma counter (Beckman, Fullerton, Calif.). The percent specific lysis was calculated by the formula: % lysis=100×(experimental cpm−spontaneous release)/(maximum release−spontaneous release).

6. Flow Cytometry

For flow cytometric experiments, two or three fluorochromes (PE, FITC, and Tri-color) (PharMingen) were used to gate on the CD3 T lymphocyte population of tumor nodule single-cell suspensions. DCs were defined as the CD11c and DEC 205 bright populations within tumor nodules and lymph nodes. Cells were identified as lymphocytes or DC by gating based on forward and side scatter profiles. Flow cytometric analyses were performed on a FACScan flow cytometer (Becton Dickinson, San Jose, Calif.) in the University of California, Los Angeles, Jonsson Cancer Center Flow Cytometry Core Facility. Between 5,000 and 15,000 gated events were collected and analyzed using Cell Quest software (Becton Dickinson).

7. Intracellular Cytokine Analysis

T lymphocytes from single-cell suspensions of tumor nodules and lymph nodes of SLC-treated and diluent-treated 3LL tumor-bearing mice were depleted of RBC with distilled, deionized $H_2O$ and were evaluated for the presence of intracytoplasmic GM-CSF and IFN-γ. Cell suspensions were treated with the protein transport inhibitor kit GolgiPlug (PharMingen) according to the manufacturer's instructions. Cells were harvested and washed twice in 2% FBS-PBS. Cells ($5×10^5$) cells were resuspended in 200 µl of 2% FBS-PBS with 0.5 µg FITC-conjugated mAb specific for cell surface Ags CD3, CD4, and CD8 for 30 min at 4° C. After two washes in 2% FBS-PBS, cells were fixed, permeabilized, and washed using the Cytofix/Cytoperm Kit (PharMingen) following the manufacturer's protocol. The cell pellet was resuspended in 100 µl Perm/Wash solution and stained with 0.25 µg PE-conjugated anti-GM-CSF and anti-IFN-γ mAb for intracellular staining. Cells were incubated at room temperature in the dark for 30 min, washed twice, resuspended in 300 µl PBS, 2% paraformaldehyde solution, and analyzed by flow cytometry.

Typical SLC Polypeptides.

Table 4 below provides illustrative human and murine SLC polypeptide sequences.

TABLE 4

Human SLC

MAQSLALSLLILVLAFGIPRTQGSDGGAQDCCLKYSQRKIPAKVVRSYRKQEPSLGCS
IPAILFLPRKRSQAELCADPKELWVQQLMQHLDKTPSPQKPAQGCRKDRGASKTGK
KGKGSKGCKRTERSQTPKGP (SEQ ID NO: 1)

Murine

SLCMAQMMTLSLLSLDLALCIPWTQGSDGGGQDCCLKYSQKKIPYSIVRGYRKQEPS
LGCPIPAILFLPRKHSKPELCANPEEGWVQNLMRRLDQPPAPGKQSPGCRKNRGTSK
SGKKGKGSKGCKRTEQTQPSRG (SEQ ID NO: 2)

Example 2: Examining Immunomodulatory Molecules in Syngeneic Transplantable Tumor Models Using SLC as a Illustrative Molecule The disclosure provided herein tests antitumor properties of SLC utilizing two syngeneic transplanted murine lung cancer models. In both models, intratumoral SLC administration caused significant reduction in tumor volumes compared with diluent-treated tumor-bearing control mice ($p<0.01$), and 40% of mice showed complete tumor eradication (FIGS. 1, A and D). To determine whether the decrease in tumor volumes resulted from a direct effect of SLC on L1C2 and 3LL, the in vitro proliferation of the tumor cells was assessed in the presence of SLC. SLC (200 ng/ml) was added to 105 L1C2 and 3LL cells plated in 12-well Costar plates, and cell numbers were monitored daily for 3 days. SLC did not alter the in vitro proliferation rates of these tumor cells.

To evaluate the role of host immunity in SLC-mediated antitumor responses, SLC was injected intratumorally in tumor-bearing SCID beige CB17 mice. SLC administration did not alter tumor volumes in SCID mice (FIG. 1E). Similarly, in CD4 and CD8 knockout mice, SLC failed to reduce tumor volumes, indicating that SLC-mediated antitumor responses were both CD4 and CD8 dependent (FIG. 1, B and C).

Because tumor progression can be modified by host cytokine profiles (Alleva et al., J. Immunol. 153:1674; Rohrer et al., J. Immunol. 155:5719), the cytokine production from tumor nodules after intratumoral SLC administration was examined. The following cytokines were measured: VEGF, IL-10, PGE2, TGF-$\beta$, IFN-$\gamma$, GM-CSF, IL-12, MIG, and IP-10 (Table 1A). The production of these cytokines were evaluated for the following reasons. The tumor site has been documented to be an abundant source of PGE-2, VEGF, IL-10, and TGF-$\beta$, and the presence of these molecules at the tumor site have been shown to suppress immune responses (Huang et al., Cancer Res. 58:1208; Bellone et al., Am. J. Pathol. 155:537; Gabrilovich et al., Nat. Med. 2:1096). VEGF, PGE2, and TGF-$\beta$ have also previously been documented to promote angiogenesis (Fajardo et al., Lab. Invest. 74:600; Ferrara et al., Breast Cancer Res. Treat. 36:127; 28; Tsujii et al., Cell 93:705). Abs to VEGF, TGF-$\beta$, PGE-2 and IL-10 have the capacity to suppress tumor growth in in vivo model systems. VEGF has also been shown to interfere with DC maturation (Gabrilovich et al., Nat. Med. 2:1096). Both IL-10 and TGF$\beta$ are immune inhibitory cytokines that may potently suppress Ag presentation and antagonize CTL generation and macrophage activities, thus enabling the tumor to escape immune detection (Sharma et al., J. Immunol. 163:5020; Bellone et al., Am. J. Pathol. 155:537). Compared with tumor nodules from diluent-treated tumor-bearing controls, mice treated intratumorally with SLC had significant reductions of PGE2 (3.5-fold), VEGF (4-fold), IL-10 (2-fold) and TGF-$\beta$ (2.3-fold) (Table 1A). An overall decrease in IL-10 and TGF$\beta$ at the tumor site after SLC administration may have promoted Ag presentation and CTL generation. The decrease in VEGF and TGF-$\beta$ at the tumor site after SLC administration may have contributed to an inhibition of angiogenesis. In contrast, there was a significant increase in IFN-$\gamma$ (5-fold), GM-CSF (10-fold), IL-12 (2-fold), MIG (6.6-fold), and IP-10 (2-fold) after SLC administration (Table 1A).

Although IL-12 is a key inducer of type 1 cytokines, IFN-$\gamma$ is a type 1 cytokine that promotes cell-mediated immunity. Increases in IL-12 (2-fold) could explain the relative increase in IFN-$\gamma$ (5-fold) at the tumor site of SLC-treated mice (Table 1A). The tumor cells used for this study do not make detectable levels of IL-12. We therefore anticipate that macrophages and DC are the predominant sources of IL-12 at the tumor site.

MIG and IP-10 are potent angiostatic factors that are induced by IFN-$\gamma$ and may be responsible, in part, for IL-12-mediated tumor reduction (Strieter et al., Biochem. Biophys. Res. Commun. 210:51; Tannenbaum et al., J. Immunol. 161:927; Arenberg et al., J. Exp. Med. 184:981). Hence, an increase in IFN-$\gamma$ at the tumor site of SLC-treated mice could explain the relative increase in MIG (6.6-fold) and IP-10 (2-fold) (Table 1A). Both MIG and IP-10 are chemotactic for stimulated CXCR3-expressing T lymphocytes, and this could also increase IFN-$\gamma$ at the tumor site (Farber et al., J. Leukocyte Biol. 61:246). An increase in GM-CSF (10-fold) in the tumor nodules of SLC treated mice could enhance DC maturation and Ag presentation (Banchereau et al., Nature 392:245).

Based on the current results, the decrease in immunosuppressive cytokines and concomitant increase in type 1 cytokines could be a direct effect of SLC on the cells resident within the tumor nodules. Alternatively, these changes could be a result of SLC-recruited T cells and DC. To begin to address this question, we evaluated the production of type 1 and immunosuppressive cytokines from tumor- and lymph node-derived cells in response to SLC in vitro. Tumor cells ($1 \times 10^6$) or lymph node-derived cells ($5 \times 10^6$) were cocultured with SLC (200 ng/ml) for 24 h for cytokine determinations. SLC did not affect tumor cell production of VEGF, TGF-$\beta$, IL-10, or PGE-2. Compared with the control untreated lymph node cells SLC significantly increased lymph node-derived IL-12 ($288 \pm 15$ pg/ml vs $400 \pm 7$ pg/ml) while decreasing IL-10 ($110 \pm 5$ pg/ml vs $67 \pm 1$ pg/ml), PGE2 ($210 \pm 4$ pg/ml vs $70 \pm 2$ pg/ml), and TGF-$\beta$ ($258 \pm 9$ pg/ml vs $158 \pm 7$ pg/ml) production in an overnight in vitro culture. SLC did not alter lymph node-derived lymphocyte production of IFN-$\gamma$ and GM-CSF in vitro. Because SLC is documented to have antiangiogenic effects (Soto et al., Proc.

Natl. Acad. Sci. USA 95:8205; Arenberg et al., Am. J. Respir. Crit. Care Med. 159:A746), the tumor reductions observed in these models may be due to T cell-dependent immunity as well as a participation by T cells in inhibiting angiogenesis (Tannenbaum et al., J. Immunol. 161:927). Further studies will be necessary to delineate the cell types and proteins critical for the decrease in immunosuppressive cytokines and the increase in type 1 cytokines after SLC administration.

To determine whether the increase in GM-CSF and IFN-γ in the tumor nodules in response to SLC could be explained by an increase in the frequency of CD4 and CD8 T cell subsets secreting these cytokines, flow cytometric analyses were performed. CD3 T cells that stained positively for cell surface markers CD4 or CD8 were evaluated in single-cell suspensions from tumor nodules. In the tumor nodules of SLC-treated mice, within the gated T lymphocyte population, there was a significant increase in the frequency of CD4 and CD8 T lymphocytes in comparison to diluent-treated mice (25 and 33% vs 15 and 11%, respectively; p<0.01). The GM-CSF and IFN-γ profile of CD4 and CD8 T cells at the tumor sites and lymph nodes were determined by intracytoplasmic staining. SLC administration resulted in an increased frequency of CD4 and CD8 T lymphocytes from tumor nodules and lymph nodes secreting GM-CSF and IFN-γ (Table 2A).

Figure 2:
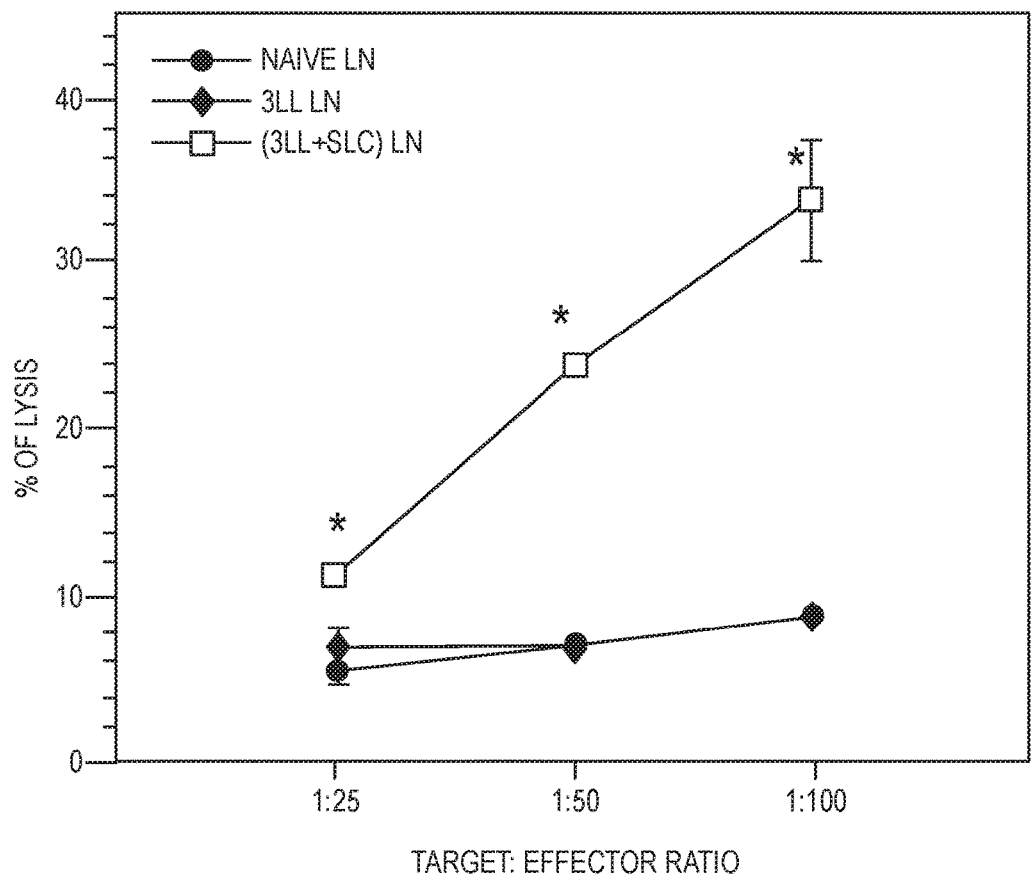
FIG. 2. Intratumoral SLC administration augments the cytolytic capacity of lymph node (LN)-derived lymphocytes. The cytolytic capacity of lymph node-derived lymphocytes from SLC-treated and diluent control tumor-bearing mice was determined after 1 week of stimulation with irradiated 3LL tumors. Lymph node-derived lymphocytes ($5 \times 10^6$ cells/ml) were cultured with irradiated 3LL ($10^5$ cells/ml) tumors at a ratio of 50:1 in a total volume of 5 ml. After a 5-day culture, the lymph node-derived lymphocytes cytolytic capacity was assessed against $^{51}$Cr-labeled 3LL tumor targets. After intratumoral SLC administration, the cytolytic capacity of LNDL was significantly enhanced above that of lymphocytes from diluent-treated tumor-bearing mice. *, p<0.01.

DC are uniquely potent APC involved in the initiation of immune responses, and it is well documented that SLC strongly attracts mature DC (Chan et al., Blood 93:3610; Banchereau et al., Nature 392:245). Because intratumoral SLC administration led to significant tumor reduction, we questioned whether intratumoral SLC administration led to enhanced DC infiltration of tumor nodules and lymph nodes. Single-cell suspensions of tumor nodules and lymph nodes from SLC and diluent-treated tumor-bearing mice were stained for the DC surface markers CD11c and DEC205. In the SLC-treated tumor-bearing mice, there was an increase in both the frequency and mean channel fluorescence intensities of DC for cell surface staining of CD11c and DEC205 in the tumor nodules and lymph nodes in comparison with diluent-treated 3LL tumor-bearing mice (Table 2A). These findings indicate that intratumoral SLC administration effectively recruited DC to the tumor site We next asked whether intratumoral SLC administration could induce significant systemic immune responses. To address this question, lymph node and splenocytes from SLC and diluent-treated tumor-bearing mice were cocultured with irradiated tumor cells for 24 h, and GM-CSF, IFN-γ, IL-10, and IL-12 levels were determined by ELISA. After secondary stimulation with irradiated tumor cells, splenocytes and lymph node-derived cells from SLC-treated tumor-bearing mice secreted significantly increased levels of IFN-γ (13- to 28-fold), GM-CSF (3-fold spleen only) and IL-12 (1.3- to 4-fold). In contrast, IL-10 secretion was reduced (6- to 9-fold) in SLC-treated mice (Table 3A). Moreover, intratumoral SLC administration led to enhanced lymph node-derived lymphocyte cytolytic activity against the parental tumor cells (FIG. 2). We speculate that the phenotype of the effector cell population in the cytolytic experiments is CD8+T lymphocytes because SLC did not affect tumor growth in SCID mice. However, tumorigenesis experiments utilizing CD4 and CD8 knockout mice demonstrate the importance of both CD4 and CD8 T lymphocytes subsets for effective tumor reduction. Because CD4 T lymphocytes can also act as cytolytic effectors (Sun et al., Cell. Immunol. 195:81; Semino et al., Cell. Immunol. 196: 87), further studies will be required to delineate the role of CD4 T lymphocytes in SLC-mediated tumor reduction.

The results of this study indicate that intratumoral SLC administration leads to colocalization of both DC and T lymphocytes within tumor nodules and T cell dependent tumor rejection. These findings provide a strong rationale for further evaluation of SLC in tumor immunity and its use in cancer immunotherapy.

Example 3: Methods and Materials for Examining Immunomodulatory Molecules Such as SLC in Spontaneous Tumor Models 1. Cell Culture.

Clara cell lung tumor cells (CC-10 Tag and H-2q) were derived from freshly excised lung tumors that were propagated in RPMI 1640 (Irvine Scientific, Santa Ana, Calif.) supplemented with 10% FBS (GeminiBioproducts, Calabasas, Calif.), penicillin (100 units/ml), streptomycin (0.1 mg/ml), and 2 mM of glutamine (JRH Biosciences, Lenexa, Kans.) and maintained at 37° C. in humidified atmosphere containing 5% CO2 in air. After two in vivo passages, CC-10 TAg tumor clones were isolated. The cell lines were *Mycoplasma* free, and cells were used up to the tenth passage before thawing frozen stock cells from liquid $N_2$.

2. CC10TAg Mice.

The transgenic CC-10 TAg mice, in which the SV40large TAg is expressed under control of the murine Clara cell-specific promoter, were used in these studies (Magdaleno et al., Cell Growth Differ., 8: 145-155, 1997). All of the mice expressing the transgene developed diffuse bilateral bronchoalveolar carcinoma. Tumor was evident bilaterally by microscopic examination as early as 4 weeks of age. After 3 months of age, the bronchoalveolar pattern of tumor growth coalesced to form multiple bilateral tumor nodules. The CC-10 TAg transgenic mice had an average life span of 4 months. Extrathoracic metastases were not noted. Breeding pairs for these mice were generously provided by Francesco J. DeMayo (Baylor College of Medicine, Houston, Tex.). Transgenic mice were bred at the West Los Angeles Veteran Affairs vivarium and maintained in the animal research facility. Before each experiment using the CC-10 TAg transgenic mice, presence of the transgene was confirmed by PCR of mouse tail biopsies. The 5' primer sequence was SM19-TAG: 5'-TGGACCTTCTAGGTCTT-GAAAGG-3' (SEQ ID NO: 3), and the 3' primer sequence was SM36-TAG: 5'-AGGCATTCCACCACTGCTCC-CATT-3' (SEQ ID NO: 4). The size of the resulting PCR fragment is 650 bp. DNA (1 μg) was amplified in a total volume of 50 μl, which contained 10 mM Tris-HCl (pH 8.3), 50 mM KCl, 200 μM each deoxynucleotidetriphosphates, 0.1 μM primers, 2.5 mM MgCl2, and 2.5 units of Taq polymerase. PCR was performed in a Perkin-Elmer DNA thermal cycler (Norwalk, Conn.). The amplification profile for the SV40 transgene consisted of 40 cycles, with the first cycle denaturation at 94° C. for 3 min, annealing at 58° C. for 1 min, and extension at 72° C. for 1 min, followed by 39 cycles with denaturation at 94° C. for 1 min, and the same annealing and extension conditions. The extension step for the last cycle was 10 min. After amplification, the products were visualized against molecular weight standards on a 1.5% agarose gel stained with ethidium bromide. All of the experiments used pathogen-free CC-10 TAg transgenic mice beginning at 4-5 week of age.

3. The SLC Therapeutic Model in CC-10 TAg Mice.

CC-10 TAg transgenic mice were injected in the axillary node region with murine recombinant SLC (0.5 μg/injection;

Pepro Tech, Rocky Hill, N.J.) or normal saline diluent, which contained equivalent amounts of murine serum albumin (Sigma Chemical Co., St. Louis, Mo.) as an irrelevant protein for control injections. Beginning at 4-5 weeks of age, SLC or control injections were administered three times per week for 8 weeks. The endotoxin level reported by the manufacturer was <0.1 ng/µg (1 endotoxin unit/µg) of SLC. The dose of SLC (0.5 µg/injection) was chosen based on our previous studies (Arenberg et al., J. Exp. Med. 184:981) and the in vitro biological activity data provided by the manufacturer. Maximal chemotactic activity of SLC for total murine T cells was found to be 100 ng/ml. For in vivo evaluation of SLC-mediated antitumor properties we used 5-fold more than this amount for each injection. At 4 months, mice were sacrificed, and lungs were isolated for quantification of tumor surface area. Tumor burden was assessed by microscopic examination of H&E-stained sections with a calibrated graticule (a 1-cm$^2$ grid subdivided into 100 1-mm$^2$ squares). A grid square with tumor occupying >50% of its area was scored as positive, and the total number of positive squares was determined as described previously (Sharma et al., J. Immunol., 163: 5020-5028, 1999). Ten separate fields from four histological sections of the lungs were examined under high-power (×20 objective). Ten mice from each group were not sacrificed so that survival could be assessed.

4. Cytokine Determination from Tumor Nodules, Lymph Nodes, and Spleens.

The cytokine profiles in tumors, lymph nodes, and spleens were determined in both SLC and diluent-treated mice as described previously (Sharma et al., J. Immunol., 163: 5020-5028, 1999). Non-necrotic tumors were harvested and cut into small pieces and passed through a sieve (Bellco, Vineland, N.J.). Axillary lymph nodes and spleens were harvested from SLC-treated tumor-bearing, control tumor-bearing, and normal control mice. Lymph nodes and spleens were teased apart, RBC depleted with ddH2O, and brought to tonicity with 1×PBS. After a 24-h culture period, tumor nodule supernatants were evaluated for the production of IL-10, IL-12, GM-CSF, IFN-γ, TGF-β, VEGF, MIG, and IP-10 by ELISA and PGE-2 by EIA. Tumor-derived cytokine and PGE-2 concentrations were corrected for total protein by Bradford assay (Sigma Chemical Co.). For cytokine determinations after secondary stimulation with irradiated tumor cells, splenocytes (5×10$^6$ cells/ml), were cocultured with irradiated (100 Gy, Cs$^{137}$ x-rays) CC-10 TAg tumor cells (10$^5$ cells/ml) at a ratio of 50:1 in a total volume of 5 ml. After a 24-h culture, supernatants were harvested and GM-CSF, IFN-γ, and IL-10 determined by ELISA.

5. Cytokine ELISA.

Cytokine protein concentrations from tumor nodules, lymph nodes, and spleens were determined by ELISA as described previously (Sharma et al., Gene Ther., 4: 1361-1370, 1997). Briefly, 96-well Costar (Cambridge, Mass.) plates were coated overnight with 4 µg/ml of the appropriate antimouse mAb to the cytokine being measured. The wells of the plate were blocked with 10% FBS (Gemini Bioproducts) in PBS for 30 min. The plate was then incubated with the antigen for 1 h, and excess antigen was washed off with PBS/Tween 20. The plate was incubated with 2 µg/ml of biotinylated mAb to the appropriate cytokine (PharMingen) for 30 min, and excess antibody was washed off with PBS/Tween 20. The plates were incubated with avidin peroxidase, and after incubation in 0-phenylenediamine substrate to the desired extinction, the subsequent change in color was read at 490 nm with a Molecular Devices Microplate Reader (Sunnyvale, Calif.). The recombinant cytokines used as standards in the assay were obtained from PharMingen. IL-12 (Biosource) and VEGF (Oncogene Research Products, Cambridge, Mass.) were determined using kits according to the manufacturer's instructions. MIG and IP-10 were quantified using a modification of a double ligand method as described previously (Standiford et al., J. Clin. Investig., 86: 1945-1953, 1990). The MIG and IP-10 antibodies and protein were obtained from R&D (Minneapolis, Minn.). The sensitivities of the IL-10, GM-CSF, IFN-γ, TGF-β, MIG, and IP-10 ELISA were 15 pg/ml. For IL-12 and VEGF the ELISA sensitivities were 5 pg/ml.

5. PGE2 EIA.

PGE2 concentrations were determined using a kit from Cayman Chemical Co. (Ann Arbor, Mich.) according to the manufacturer's instructions as described previously (Huang et al., Cancer Res., 58: 1208-1216, 1998). The EIA plates were read by a Molecular Devices Microplate reader (Sunnyvale, Calif.).

6. Flow Cytometry.

For flow cytometric experiments, two or three fluorochromes (PE, FITC, and Tri-color; PharMingen) were used to gate on the CD3T-lymphocyte population of tumor nodule, lymph node, and splenic single cell suspensions. DCs were defined as the CD11c and DEC 205 bright populations within tumor nodules, lymph nodes, and spleens. Cells were identified as lymphocytes or DCs by gating based on forward and side scatter profiles. Flow cytometric analyses were performed on a FACScan flow cytometer (Becton Dickinson, San Jose, Calif.) in the University of California, Los Angeles, Jonsson Cancer Center Flow Cytometry Core Facility. Between 5,000 and 15,000 gated events were collected and analyzed using Cell Quest software (Becton Dickinson).

7. Intracellular Cytokine Analysis.

T lymphocytes from single cell suspensions of tumor nodules, lymph nodes, and spleens of SLC-treated and diluent treated CC-10 TAg transgenic mice were depleted of RBC with distilled, deionized H$_2$O and were evaluated for the presence of intracytoplasmic GM-CSF and IFN-γ Cell suspensions were treated with the protein transport inhibitor kit Golgi Plug (PharMingen) according to the manufacturer's instructions. Cells were harvested and washed twice in 2% FBS/PBS. Cells (5×10$^5$) were resuspended in 200 µl of 2% FBS/PBS with 0.5 µg of FITC-conjugated mAb specific for cell surface antigens CD3, CD4, and CD8 for 30 min at 4° C. After two washes in 2% FBS/PBS, cells were fixed, permeabilized, and washed using the Cytofix/Cytoperm kit (PharMingen) following the manufacturer's protocol. The cell pellet was resuspended in 100 µl of Perm/Wash solution and stained with 0.25 µg of PE-conjugated anti-GM-CSF and anti-IFN-γ mAb for intracellular staining. Cells were incubated at room temperature in the dark for 30 min and washed twice, resuspended in 300 µl of PBS/2% paraformaldehyde solution, and analyzed by flow cytometry.

Example 4: SLC Mediates Potent Antitumor Responses in a Murine Model of Spontaneous Bronchoalveolar Carcinoma Using the material and methods described in Example 3, the antitumor efficacy of SLC in a spontaneous bronchoalveolar cell carcinoma model in transgenic mice in which the SV40 large TAg is expressed under control of the murine Clara cell-specific promoter, CC-10 was evaluated. (Magdaleno et al., Cell Growth Differ., 8: 145-155, 1997). Mice expressing the transgene develop diffuse bilateral bronchoalveolar carcinoma and have an average life span of 4 months. SLC (0.5 μg/injection) or the same concentration of murine serum albumin was injected in the axillary lymph node region beginning at 4 weeks of age, three times per week and continuing for 8 weeks. At 4 months when the control mice started to succumb because of progressive lung tumor growth, mice were sacrificed in all of the treatment groups, and lungs were isolated and paraffin embedded. H&E staining of paraffin-embedded lung tumor sections from control-treated mice revealed large tumor masses throughout both lungs with minimal lymphocytic infiltration (FIG. 3 A and C). In contrast, SLC-treated mice had significantly smaller tumor nodules with extensive lymphocytic infiltration (FIG. 3, B and D). Mice treated with SLC had a marked reduction in pulmonary tumor burden as compared with diluent treated control mice (FIG. 3E). SLC-treated mice had prolonged survival compared with mice receiving control injections. Median survival was 18±2 weeks for control-treated mice, whereas mice treated with SLC had a median survival of 34±3 weeks (P<0.001).

Example 5: SLC Treatment of CC-10 Tag Mice Promotes Type 1 Cytokine and Antiangiogenic Chemokine Release and a Decline in the Immunosuppressive Cytokines TGF-β and VEGF On the basis of previous reports indicating that tumor progression can be modified by host cytokine profiles (Alleva et al., J. Immunol., 153: 1674-1686, 1994; Rohrer et al., J. Immunol., 155: 5719-5727, 1995), we evaluated the cytokine production from tumor sites, lymph nodes, and spleen after SLC therapy. Cytokine profiles in the lungs, spleens, and lymph nodes of CC-10 TAg mice treated with recombinant SLC were compared with those in diluent-treated control mice bearing tumors as well as nontumor bearing controls. SLC treatment of CC-10 TAg mice led to systemic induction of Type 1 cytokines but decreased production of immunosuppressive mediators. Lungs, lymph node, and spleens were harvested, and after a 24-h culture period, supernatants were evaluated for the presence of VEGF, IL-10, IFN-γ, GM-CSF, IL-12, MIG, IP-10, and TGF-β by ELISA and for PGE-2 by EIA. Compared with lungs from the diluent-treated group, CC-10 TAg mice treated with SLC had significant reductions in VEGF (3.5-fold) and TGF-β (1.83-fold) but an increase in IFN-γ (160.5-fold), IP-10 (1.7-fold), IL-12 (2.1-fold), MIG (2.1-fold), and GM-CSF (8.3-fold; Table 1B). Compared with the diluent treated group, splenocytes from SLC-treated CC-10 TAg mice revealed reduced levels of PGE-2 (14.6-fold) and VEGF (20.5-fold) but an increase in GM-CSF (2.4-fold), IL-12 (2-fold), MIG (3.4-fold), and IP-10 (4.1-fold; Table 1B). Compared with diluenttreated CC-10 TAg mice, lymph node-derived cells from SLC treated mice secreted significantly enhanced levels of IFN-γ (2.2-fold), IP-10 (2.3-fold), MIG (2.3-fold), and IL-12 (2.5-fold) but decreased levels of TGF-β (1.8-fold; Table 1B). The immunosuppressive mediators PGE-2 and IL-10 were not altered at the tumor sites of SLC-treated mice; however, there was a significant reduction in the level of PGE-2 in the spleen of SLC-treated mice. To determine whether SLC administration induced significant specific systemic immune responses, splenocytes from SLC and diluent treated CC-10 TAg mice were cocultured in vitro with irradiated CC-10 TAg tumor cells for 24 h, and GM-CSF, IFN-γ, and IL-10 were determined by ELISA. After secondary stimulation with irradiated tumor cells, splenocytes from SLC-treated tumor-bearing mice secreted significantly increased levels of IFN-γ (5.9-fold) and GM-CSF (2.2-fold). In contrast, IL-10 secretion was reduced 5-fold (Table 3B).

Example 6: SLC Treatment of CC-10 Tag Mice Leads to Enhanced DC and T-Cell Infiltrations of Tumor Sites, Lymph Nodes, and Spleen To determine the cellular source of GM-CSF and IFN-γ, single cell suspensions of tumors, lymph nodes, and spleens were isolated from SLC and diluent control-treated CC-10 TAg mice. T-lymphocyte infiltration and intracellular cytokine production were assessed by flow cytometry. The cells were also stained to quantify DC infiltration at each site. Compared with the diluent-treated control group, the SLC-treated CC-10 TAg mice showed significant increases in the frequency of cells expressing the DC surface markers CD11c and DEC 205 at the tumor site, lymph nodes, and spleen (Table 2B). Similarly, as compared with the diluent-treated control group, there were significant increases in the frequency of CD4 and D8 cells expressing IFN-γ and GM-CSF at the tumor sites, lymph nodes, and spleen of SLC-treated CC-10 TAg mice (Table 2B).

Example 7: SLC-Mediated Anti-Tumor Responses Require IFN-γ, MIG and IP-10

Studies presented herein teach that the SLC-mediated anti-tumor response is accompanied by the enhanced elaboration of IFN-γ, IP-10 and MIG at the tumor site. IP-10, MIG and IFN-γ are known to have potent anti-tumor activities in vivo. In this context a study was undertaken to determine if the augmentation of these cytokines served as effector molecules in SLC mediated tumor reduction. Here we show that SLC-mediated anti-tumor responses require the cytokines IP-10, MIG and IFN-γ.

We determined the roles of IFN-γ, IFN-γ inducible protein IP-10 (IP-10) and monokine-induced by IFN-γ (MIG) in the in vivo SLC-mediated anti-tumor responses. Depletion of IP-10, MIG and IFN-γ in vivo significantly reduced the antitumor efficacy of SLC. Assessment of cytokine production at the tumor site showed an interdependence of IFN-γ, MIG and IP-10; neutralization of any one of these cytokines in vivo caused a concomitant decrease in all three cytokines. These findings indicate that the SLC-mediated anti-tumor response requires the induction of IP-10, MIG and IFN-γ at the tumor site.

Materials and Methods

Cell Culture and Tumorigenesis Model

A weakly immunogenic lung cancer, Lewis lung carcinoma (3 LL, H-$2^b$) was utilized for assessment of cytokines important for SLC-mediated anti-tumor responses in vivo. The cells were routinely cultured as monolayers in 25 cm$^3$ tissue culture flasks containing RPMI 1640 medium (Irvine Scientific, Santa Anna, Calif.) supplemented with 10% fetal bovine serum (FBS) (Gemini Bioproducts, Calabasas, Calif.), penicillin (100 U/ml), streptomycin (0.1 mg/ml), 2 mM glutamine (JRH Biosciences, Lenexa, Kans.) and maintained at 37° C. in humidified atmosphere containing 5% $CO_2$ in air. The cell lines were mycoplasma free and cells were utilized up to the tenth passage before thawing frozen stock cells from liquid $N_2$. For tumorigenesis experiments, $10^5$ 3 LL tumor cells were inoculated by s.c. injection in the right supra scapular area of C57Bl/6 and tumor volume was monitored 3 times per week. Five day established tumors were treated with intratumoral injection of 0.5 μg of murine recombinant SLC or PBS diluent (Pepro Tech, Rocky Hill, N.J.) administered three times per week for two weeks. The endotoxin level reported by the manufacturer was less than 0.1 ng per µg (1 EU/µg) of SLC. The amount of SLC (0.5 µg) used for injection was determined by the in vitro biological activity data provided by the manufacturer. Maximal chemotactic activity of SLC for total murine T cells was found to be 100 ng/ml. For in vivo evaluation of SLC-mediated anti-tumor properties we utilized 5 fold more than this amount for each intratumoral injection. Tumorigenesis experiments were also performed in which equivalent amounts of murine serum albumin were utilized (Sigma, St. Louis, Mo.) as an irrelevant protein for control injections. 24 hours prior to SLC treatment, and then three times a week, mice were treated i.p. with 35 mg/dose of anti-IP-10 or anti-MIG, and 100 µg/dose of purified IFN-γ (ATCC R4562) or 35 mg/dose of control antibody for the duration of the experiment. At doses of antibody administered there was a significant in vivo depletion of the respective cytokines at the tumor site. Two bisecting diameters of each tumor were measured with calipers. The volume was calculated using the formula (0.4) (ab$^2$), with "a" as the larger diameter and "b" as the smaller diameter.

Cytokine ELISA

MIG, IP-10 and IFN-γ were quantified using a modification of a double ligand method as previously described. The MIG and IP10 antibodies and recombinant cytokine proteins were from R&D (Minneapolis, Minn.). The IFN-γ antibodies pairs and recombinant cytokine were from Pharmingen. The sensitivities of the IFNγ, MIG and IP-10 ELISA were 15 pg/ml.

Results

Because SLC is documented to have direct anti-angiogenic effects, the tumor reductions observed in our model could have been due to T cell-dependent immunity as well as participation by T cells secreting IFN-γ in inhibiting angiogenesis. IFN-γ mediates a range of biological effects that facilitate anticancer immunity. MIG and IP-10 are potent angiostatic factors that are induced by IFN-γ and hence we postulated that in addition to IFN-γ they are be responsible in part for the tumor reduction following SLC administration.

To determine if the co-localization of DC and T cells to the tumor site was sufficient for SLC-mediated anti-tumor responses and/or whether the accompanying relative increases in the cytokines MIG, IP-10 and IFN-γ at the tumor site play a role in tumor reduction, these cytokines were depleted with antibodies in SLC treated mice. Anti-IP-10, MIG and IFN-γ antibodies significantly inhibited the efficacy of SLC (* $p<0.01$ compared to the control antibody group). Cytokine determinations at the tumor site showed that the relative increase in MIG and IP-10 at the tumor site are IFN-γ dependent because neutralization of IFN-γ caused a decrease in these cytokines. Thus, an increase in IFN-γ at the tumor site of SLC-treated mice could explain the relative increases in IP-10 and MIG. The converse was also observed; IFN-γ production at the tumor site was found to be dependent on MIG and IP-10 because neutralization of these cytokines caused a decrease in IFN-γ. Thus IFN-γ, MIG and IP-10 in SLC treated mice showed an interdependence since in vivo neutralization of any one of these cytokines caused a concomitant decrease in all three cytokines. Both MIG and IP-10 are chemotactic for stimulated CXCR3-expressing activated T lymphocytes that could further amplify IFN-γ at the tumor site. Our results suggest that the anti-tumor properties of SLC may be due to its chemotactic capacity in colocalization of DC and T cells as well as the induction of key cytokines such as IFN-γ, IP-10, MIG.

$10^5$ 3 LL tumors were implanted in C57Bl/6 mice. 5 days following tumor implantation, mice were treated intratumorally with 0.5 µg of recombinant murine SLC three times per week. One day before SLC administration, mice were given the respective cytokine antibody by i.p. injection. The antibodies were administered three times per week. SLC treated mice had a significant induction in IFN-γ, MIG and IP-10 compared to diluent treated control tumor bearing mice ($p<0.001$). Whereas neutralization of IFN-γ in vivo reduced IFN-γ, IP-10 and MIG, neutralization of MIG and IP-10 led to a relative decrease in those cytokines. Neutralization of MIG also led to a decrease in IFN-γ and IP-10. Results are expressed as pg/mg of total protein. Total protein was determined by the Bradford assay. Results of these experiments are provided in Table 5 below.

TABLE 5

| Treatment groups | IFNγ | MIG | IP10 |
|---|---|---|---|
| Diluent treated | 306 ± 25 | 599 ± 29 | 562 ± 54 |
| Control Ab + SLC | 2,200 ± 57 | 10,350 ± 159 | 10,900 ± 168 |
| Anti IFN + SLC | 800 ± 38 | 730 ± 27 | 5400 ± 14 |
| Anti IP-10 + SLC | 990 ± 102 | 3390 ± 150 | 2001 ± 45 |
| Anti MIG + SLC | 725 ± 33 | 7970 ± 138 | 5760 ± 78 |

Example 8: SLC-Mediated Anti-Tumor Responses in a Murine Model of a Gene Therapy-Based Approach The data provided in the Examples above demonstrate how SLC polypeptide mediates syngeneic T Cell-dependent antitumor responses in vivo. To explore a gene therapy-based anti-tumor approach using a direct injectable vector, we made an adenoviral construct expressing murine SLC cDNA (Ad-SLC). In these constructs the cDNA for murine secondary lymphoid chemokine was cloned downstream of the CMV promoter in the Invitrogen pMH4 plasmid and was used as the shuttle vector.

The pJM17 plasmid that contains the entire E1-deleted Ad-5 genome was used as the recombination vector (for illustrative methods see, e.g., Cancer Gene Ther 1997 January-February; 4(1):17-25). Murine AdSLC was prepared through an in vitro recombination event in 293 cells through a recombination event between the shuttle plasmid pMH4 containing the murine SLC cDNA and the pJM17 plasmid.

Clones of Ad SLC were obtained by limiting dilution analysis of the ability of media to induce cytopathic effect on 293 cells and confirmed by murine SLC specific ELISA that we developed in our laboratory. Viral stocks were obtained by amplification of the 293 cells followed by CsCl purification, dialysis and storage as a glycerol (10% vol/vol) stock at −80° C. (see, e.g., Cancer Gene Ther 1997 January-February; 4(1):17-25).

In vitro transduction of Line 1 alveolar carcinoma cells (L1C2) and the Lewis Lung carcinoma cells (3LL, derived from C57BL/6) led to the production of 10 ng/ml/$10^6$ cells/24 hr SLC by these cell lines at an MOI of 100:1 as determined by SLC specific ELISA. We next determined the in vivo antitumor efficacy of the Ad-SLC construct using the transplantable murine L1C2 lung tumor model. $10^8$ pfu of the viral stock was added to 100 of PBS for intratumoral injection into C57BL/6 mice. $10^5$ cells were injected in the right supra scapular region of the mice and 5 days later, the tumors treated with an intratumoral injection of Ad-SLC or control Ad vector once a week for three weeks at pfu's ranging from $10^7$-$10^9$. The virus was injected into the tumor using an insulin syringe with the injectate was delivered slowly to allow for an even distribution of the virus particles in the tumor.

Figure 4A:
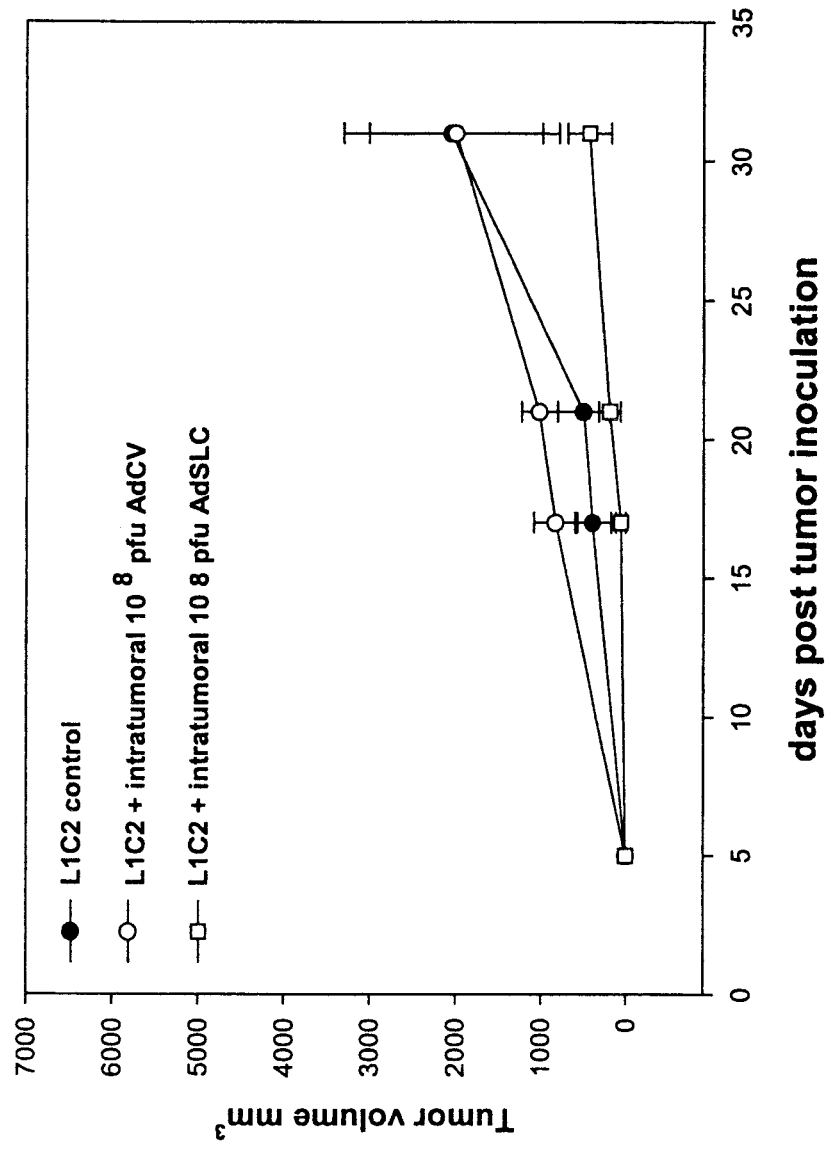

As illustrated in FIG. 4, intratumoral injection of the Ad-SLC vector led to the complete regression of the tumors in 60% of the mice whereas the control Ad vector did not have this effect. We also determined the antitumor efficacy of a single intratumoral dose of Ad-SLC at $10^8$ pfu and found it to be as effective as three doses. Mice rejecting their tumors in response to Ad-SLC therapy were able to reject a secondary challenge of $5\times10^5$ parental tumors. These results indicate that an in vivo SLC gene therapy strategy can lead to significant tumor reduction in syngeneic lung cancer models.

The in vivo gene transfer methods disclosed herein provide clinically relevant models for treating cancers. In particular, these in vivo models are directly relevant cancer models because the cancer arise in a spontaneous manner (and are therefore syngeneic). In addition, the gene therapy methods disclosed herein directly parallel the clinical model, that is the administration of a polynucleotide encoding SLC polypeptide. The fact that the administration of this gene therapy vector is shown to reduce tumor burden provides direct evidence which strongly supports the use of such vectors in clinical methods for treating cancer. Consequently this model provides a particularly useful tool for optimizing and characterizing SLC based gene therapies.

Example 9: SLC-Mediated Anti-Tumor Responses in a Human Gene Therapy-Based Approach A human gene therapy-based anti-tumor approach can be employed using a vector such as an adenoviral construct that expresses human SLC cDNA. In these constructs the cDNA for human secondary lymphoid chemokine can be cloned downstream of a promoter that allows an appropriate degree of expression such as a CMV promoter.

A plasmid such as the pJM17 plasmid that contains the entire E1-deleted Ad-5 genome can be used as the recombination vector (for illustrative methods see, e.g., Cancer Gene Ther 1997 January-February; 4(1):17-25). Human AdSLC can be prepared through an in vitro recombination event in 293 cells through a recombination event between a shuttle plasmid containing the human SLC cDNA and the recombination plasmid.

Clones of Ad SLC can be obtained by limiting dilution analysis of the ability of media to induce cytopathic effect on cells such as 293 cells and confirmed by human SLC specific ELISA that we developed in our laboratory. Viral stocks can be obtained by amplification of the cells followed by CsCl purification, dialysis and storage as a glycerol (10% vol/vol) stock at −80° C. (see, e.g., Cancer Gene Ther 1997 January-February; 4(1):17-25).

In vitro transduction of lines such as Line 1 alveolar carcinoma cells (L1C2) and the Lewis Lung carcinoma cells (3LL) can be used in the production of SLC by these cell lines at an MOI of 100:1 as determined by SLC specific ELISA. One can determine the in vivo antitumor efficacy of the ASLC construct using cells equivalent to the transplantable murine L1C2 lung tumor model. $10^8$ pfu of the viral stock can be added to 100 µl of PBS for intratumoral injection. $10^5$ cells can be injected in a region proximal to the tumor and 5 days later, the tumors can be treated with an intratumoral injection of SLC vector once a week for three weeks at pfu's ranging from $10^7$-$10^9$. In one method, the virus can be injected into the tumor using an insulin syringe with the injectate can be delivered slowly to allow for an even distribution of the virus particles in the tumor.

Example 10: Use of Adenoviral CCL-21/SLC in Typical Intratumoral Dendritic Cell (DC) Based Ex-Vivo Therapies in NSCLC In this example we demonstrate a method for achieving in-situ tumor antigen uptake and presentation utilizing intratumoral administration of ex vivo-generated gene modified DC. In this example, in order to attract mature host DC to the tumor site, the DCs were transduced with an adenoviral vector construct expressing CCL-21 (secondary lymphoid tissue chemokine (SLC)). Because CCL-21 potently attracts mature DC and activated T cells, the intratumoral injection (i.t.) of DC expressing CCL-21 leads to potent antitumor responses in lung cancer models.

In this illustrative model, $10^5$ Line 1 alveolar cell carcinoma (L1C2) cells were utilized to establish subcutaneous tumors in syngeneic BALB/c mice. Established tumors were treated i.t. with $10^6$ DC-Ad-CCL-21 (10 ng/ml/$10^6$ cells/24 hrs of CCL-21) at weekly intervals for 3 weeks. Sixty percent of the mice treated with DC-Ad-CCL-21 i.t. showed complete tumor eradication. In contrast only 12% of the mice treated with unmodified or control vector modified DCs (DC-Ad-CV) responded. Based on these results we constructed and characterized an adenoviral vector that expresses human CCL-21 (Ad-CCL-21). Human monocyte derived DCs were cultured in medium containing GM-CSF and IL-4. Following transduction on day 6, CCL-21 protein production was assessed on day 8 by ELISA. DCs transduced with Ad-CCL-21 at MOIs of 50:1 or 100:1 produced 71±15 ng/ml and 91±5 ng/ml/$10^6$ cells/48 hours. At the MOIs evaluated, DC maintained cell viability as well as their immature phenotype without significantly upregulating CD83 or CCR7R expression. In addition as few as $10^5$ DC-Ad-CCL-21 caused significant chemotaxis of peripheral blood lymphocytes and LPS-stimulated DC.

These studies provide evidence for the successful use of intratumoral DC-Ad-CCL-21 therapy in NSCLC.

Example 11: PD-L1 Expression Correlates with Immune Response in Phase 1 Trial of CCL21 Gene Modified Dendritic Cells

BACKGROUND

In the first trial in which patients received CCL21 (via introduction into the tumor by injection of CCL21 gene modified DC as described in Tech ID: 20538/UC Case 2001-381-0 Chemokine to Induce Anti-Tumor Response by Stimulating Cell-Mediated Immune Response and Inhibiting Angiogenesis) it was found that patients who had up-regulated PDL1 surface expression on their lung cancer cells at the start of therapy had limited or no specific immune responses to CCL21 therapy. Also some patients had more elevated PDL1 following CCL21 therapy. This provides evidence that blocking the PD1/PDL1 pathway by either antibodies or other means would be an effective means to improve either CCL21 or PD1/PDL1 pathway therapies. This indicates that a combination therapy would be very effective.

Anti-tumor immune response in lung cancer patients may be evoked by intratumoral (IT) administration of autologous dendritic cells (DC), transduced with a replication-deficient adenoviral (Ad) vector to express the secondary lymphoid chemokine (SLC/CCL21) gene. Here, tumor specific immune response after CCL21 gene-modified DC (Ad-CCL21-DC) administration in the context of tumor PD-L1 expression was analyzed.

Methods

Phase I, non-randomized, dose escalating, multi-cohort trial was conducted to enroll patients with Stage IIIB/IV NSCLC. Sixteen patients received 2 vaccinations at a dose of Ad-CCL21-DC (A, B, C, or D; $1\times10^6$, $5\times10^6$, $1\times10^7$, or $3\times10^7$ cells/injection) by IT injection (days 0 and 7). Peripheral blood was collected for antigen-specific ELISPOT assays, and CT guided needle biopsies of the primary lung cancer were obtained for PD-L1 expression by real time PCR and evaluation of cellular infiltrates by immunohistochemistry.

Results

Peripheral blood of 16 subjects was evaluated by ELISPOT assays. Positive response was defined as 2-fold increase in number of spots above background with an absolute number of >20 spots/$2\times10^5$ cells (positive responder; PR). A mixed response was defined as a positive response with high IFN-γ. background expression at day 0 compared to post-vaccine time points (mixed responder; MR). There were 19% (3/16) PR and 19% (3/16) MR for a total of 38% (6/16) total responders. The average PD-L1 gene copy number was 1344 (non-responder; NR) compared to 394 (MR), and 684 (PR) on day 7. Tumor CD8 T cell infiltration was induced in 40% (6/15; all subjects), 33% (3/9; NR), and 50% (3/6; MR & PR).

CONCLUSION

Intratumoral administration of autologous dendritic cells expressing the SLC/CCL21 gene demonstrated that 1) anti-tumor specific immune responses are elicited and correlate with lower PD-L1 expression, and 2) CD8 T cell infiltration into the tumor is induced.

Example 12: In Vivo Models of Intratumoral CCL21 and Checkpoint Blockade Therapy Recombinatn murine CCL21 (rmCCL21,SLC) or a relevant control is injected into syngeneic mice (C57/B16 or 129/sv) bearing NSCLC lung tumors (3LL or LKR13, respectively). The SLC is injected intratumorally when the tumor size reaches 8×8 mm (typically around d10), and again 8 days later, to augment any naturally occurring host anti-tumor immune response; based on previous findings, SLC will chemoattract T cells (helper and cytotoxic) and beneficial macrophages. As the host anti-tumor immune response mounts, there is evidence that lung tumors initiate immune evasion signaling events, including up-regulation of PD-L1 and PD-L2 for binding with the PD-1 receptor on T cells to deactivate the T cells and prevent future recruitment of T cells to the tumor. For this reason, anti-PD1 (murine) is injected intraperitoneally two days after the first injection of CCL21, and every 4 days thereafter for the duration of the experiment. On whole, it is anticipated that the host anti-tumor immune response is bolstered with SLC and tumor immune evasion is prevented with well-timed delivery of anti-PD1. The primary endpoint of these murine studies is tumor growth rate. The secondary endpoints are post-treatment (n=4 mice/group) immune cell infiltration relative to pre-treatment infiltration (n=2 mice/group). All post-treatment mice are euthanized when tumors in the untreated control group reach 22×22 mm (typically d28). After completion of these initial combination studies, the efficacy of intratumoral injection of CCL21 gene-modified autologous dendritic cells from litter mate-matched mice when combined with anti-PD1 treatment is evaluated. The results of these preclinical studies are used to guide the Phase I/II clinical trials are currently being designed that test the safety and efficacy of this combination in patients with advanced stage NSCLC.

Figure 8:
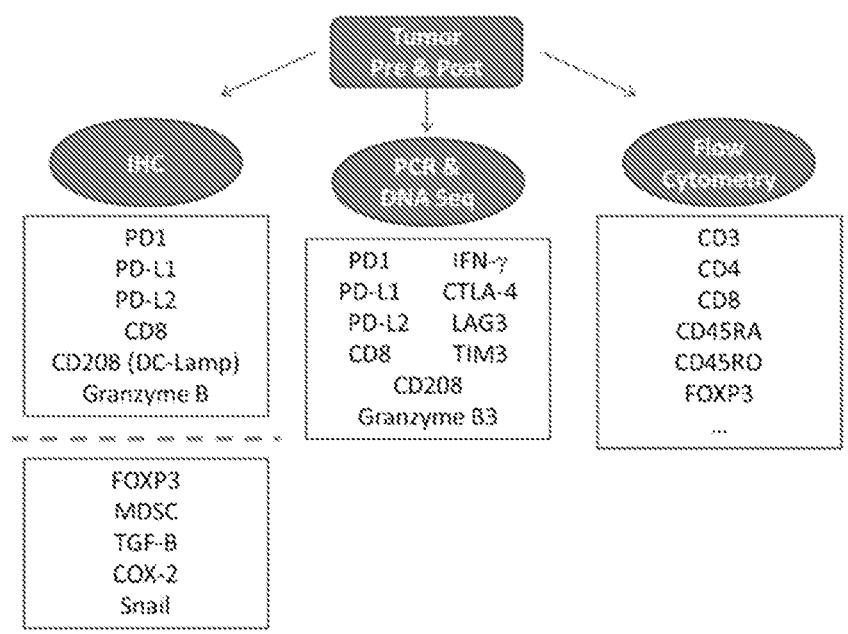
FIG. 8 is a chart of exemplary immune cell markers to be surveyed in subjects before and after treatment with SLC and checkpoint inhibitors.

FIG. 8 is a chart of exemplary immune cells markers to be surveyed in pre- and post-treatment mice from each group. The markers can be measure in tumor infiltrating immune cells by IHC and other means.

Example 13: Intratumoral CCL21 and Checkpoint Blockade Cooperatively Inhibit NSCLC Tumor Growth CCL21-DC were previously evaluated as a monotherapy in the well-characterized syngeneic KRASG12D murine model of lung cancer. In that model, decreased tumor growth, increased tumor-infiltrating lymphocyte (TIL) cytolytic activity against the autologous tumor, and increased IFNγ and TNFα in the tumor, as well as systemically in the spleen was observed. Using the same LKR13 murine model, a combination of CCL21 therapy and checkpoint inhibitor therapy was analyzed. In vitro T cell cytolytic activity against autologous tumor was evaluated in the presence of anti-PD-1 antibody (1 µg/ml) or control antibody (1 µg/ml) n=8 mice/group; the TIL were derived from tumors in the diluent CCL21-DC treatment groups.

Figure 9:
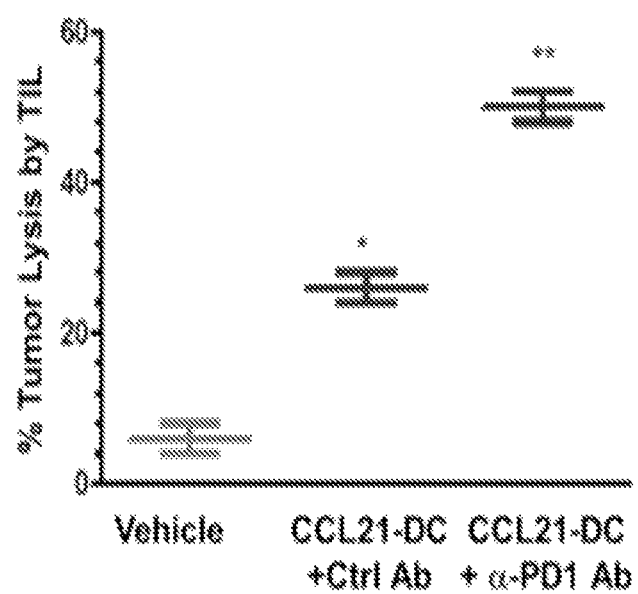
FIG. 9 shows that CCL21-DC treated mice had significantly greater cytolytic activity against the autologous tumor in the presence of PD-1 antibody relative to control antibody.

It was observed that anti-PD-1 monotherapy also inhibited tumor growth, increased TIL cytolytic activity against the autologous tumor, and increased IFNγ and TNFα in the tumor, as well as systemically in the spleen. To determine if TIL activity from the CCL21-DC treatment group could be enhanced by PD-1 blockade, an in vitro cytolytic assay was performed. TIL from the CCL21-DC group had significantly greater cytolytic activity against the autologous tumor in the presence of PD-1 antibody relative to control antibody (FIG. 9, *p<0.05 relative to diluent, **p<0.05 relative to CCL21-DC+control antibody).

Intratumoral (IT) CCL21 and intraperitoneal anti-PD-1 administered in combination was also evaluated in LKR13 tumor-bearing mice. Both monotherapies reduced final tumor volume approximately three-fold, and the combination proved more efficacious than either agent alone. Similar results were obtained utilizing the syngeneic 3LL murine lung cancer model. Both monotherapies significantly reduced tumor growth, such that the final tumor volume at the time of necropsy was approximately half that of the control group, and the combination of checkpoint blockade and CCL21 augmented the antitumor activity nearly two-fold more. Collectively, these data support the hypothesis that intratumoral CCL21 and checkpoint blockade cooperatively inhibit NSCLC tumor growth to a greater extent than either monotherapy alone.

Numerous modifications and variations in the invention as set forth in the above illustrative examples are expected to occur to those skilled in the art. Consequently only such limitations as appear in the appended claims should be placed on the invention.

What is claimed is:

1. A method for inhibiting the growth of a non-small cell lung carcinoma (NSCLC) solid tumor in a human subject comprising
   a. administering to the subject intratumorally or at the tumor site an autologous antigen presenting cell comprising an expression vector comprising a polynucleotide encoding a CCL21 polypeptide comprising the amino acid sequence SEQ ID NO:1, and
   b. administering to the subject an anti-human PD-1 antibody selected from KEYTRUDA (pembrolizumab) and OPDIVO (nivolumab) wherein the combination of said administrations exhibits synergistic anti-tumor effects.

2. The method of claim 1, wherein the expression vector is a CMV, vaccinia virus, sindbis virus, herpesvirus, adenoviral or a replication-deficient adenoviral expression vector.

3. The method of claim 1, wherein the autologous antigen presenting cell comprising the polynucleotide encoding the CCL21 polypeptide is a dendritic cell.

4. The method of claim 1, wherein at least or about $1 \times 10^6$ autologous antigen presenting cells comprising the polynucleotide encoding the CCL21 polypeptide are administered to the subject.

5. The method of claim 4, wherein the autologous antigen presenting cells produce at least or about 0.25 ng of CCL21 per $1 \times 10^6$ cells in a 24-hour period.

6. The method of claim 1, wherein the autologous antigen presenting cell comprising the expression vector comprising the polynucleotide encoding the CCL21 polypeptide is administered to the subject prior to, about 2 weeks prior to, or at the same time the anti-human PD-1 antibody.

7. The method of claim 1, wherein the autologous antigen presenting cell comprising the expression vector comprising the polynucleotide encoding the CCL21 polypeptide is administered to the subject more than once, once every 2 weeks, once every 3 weeks, or once a month.

8. The method of claim 1, wherein the anti-human PD-1 antibody is administered to the subject more than once.

9. The method of claim 8, wherein the anti-human PD-1 antibody is administered to the subject once every 2 weeks or 3 weeks.

\* \* \* \* \*

SEQUENCE LISTING

<160> NUMBER OF SEQ ID NOS: 4

<210> SEQ ID NO 1
<211> LENGTH: 134
<212> TYPE: PRT
<213> ORGANISM: Homo sapiens

<400> SEQUENCE: 1

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 2
<211> LENGTH: 133
<212> TYPE: PRT
<213> ORGANISM: Murine

<400> SEQUENCE: 2

Met Ala Gln Met Met Thr Leu Ser Leu Leu Ser Leu Asp Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Leu Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130

<210> SEQ ID NO 3
<211> LENGTH: 23
<212> TYPE: DNA
<213> ORGANISM: Murine

<400> SEQUENCE: 3

```
tggaccttct aggtcttgaa agg                                          23

<210> SEQ ID NO 4
<211> LENGTH: 24
<212> TYPE: DNA
<213> ORGANISM: Murine

<400> SEQUENCE: 4
aggcattcca ccactgctcc catt                                         24
```